(12) United States Patent
Swanson

(10) Patent No.: US 10,895,525 B2
(45) Date of Patent: Jan. 19, 2021

(54) OPTICAL MEASUREMENT SYSTEM USING MULTICORE OPTICAL FIBER

(71) Applicant: Eric Swanson, Gloucester, MA (US)

(72) Inventor: Eric Swanson, Gloucester, MA (US)

(*) Notice: Subject to any disclaimer, the term of this patent is extended or adjusted under 35 U.S.C. 154(b) by 263 days.

(21) Appl. No.: 15/462,866

(22) Filed: Mar. 19, 2017

(65) Prior Publication Data

US 2017/0268987 A1    Sep. 21, 2017

Related U.S. Application Data

(63) Continuation of application No. 14/312,621, filed on Jun. 23, 2014, now Pat. No. 9,683,928.

(Continued)

(51) Int. Cl.
*G01N 21/17* (2006.01)
*A61B 5/00* (2006.01)
(Continued)

(52) U.S. Cl.
CPC ........... *G01N 21/17* (2013.01); *A61B 5/0066* (2013.01); *G01B 9/02004* (2013.01);
(Continued)

(58) Field of Classification Search
CPC ........... G02B 6/02042; G02B 6/29302; A61B 5/0066; A61B 2562/0233; G01N 21/4795; G01H 9/002; G01S 7/4812
See application file for complete search history.

(56) References Cited

U.S. PATENT DOCUMENTS 5,321,501 A    6/1994 Swanson
5,459,570 A    10/1995 Swanson
(Continued)

FOREIGN PATENT DOCUMENTS

CN    101165471 A  *  4/2008   ............. G01N 21/25
EP    0981733    11/2004
(Continued)

OTHER PUBLICATIONS

G. Roelkens, D. Vermeulen, S. Selvaraja, Student Member, IEEE, R. Halir, W. Bogaerts, Member, IEEE, and D. Van Thourhout, "Grating-Based Optical Fiber Interfaces for Silicon-on-Insulator Photonic Integrated Circuits", IEEE Journal of Selected Topics in Quantum Electronics, vol. 17, No. 3, May/Jun. 2011.

Attila Mekis, Steffen Gloeckner, Gianlorenzo Masini, Adithyaram Narasimha, Member, IEEE, Thierry Pinguet, Subal Sahni, and Peter De Dobbelaere, "A Grating-Coupler-Enabled CMOS Photonics Platform". IEEE Journal of Selected Topics in Quantum Electronics, vol. 17, Issue 3, May/Jun. 2011.

Neil Na, Harel Frish, I-Wei Hsieh, Oshrit Harel, Roshan George, Assia Barkai, and Haisheng Rong, "Efficient broadband silicon-on-insulator grating coupler with low backreflection", Optics Letters, vol. 36, No. 11, Jun. 1, 2011.

(Continued)

*Primary Examiner* — Daniel Petkovsek
(74) *Attorney, Agent, or Firm* — Rauschenbach Patent Law Group, LLC; Kurt Rauschenbach

(57) ABSTRACT

An optical-fiber measurement system includes an optical system that generates light and a spatial optical switch that is coupled to the optical system that processes the light generated by the optical system and generates light at a plurality of spatially distributed optical ports. A respective one of a plurality of optical cores at a first end of a multicore optical fiber is positioned to receive light from a respective one of the plurality of spatially distributed optical ports, where the light generated at the plurality of spatially distributed optical ports propagates through the multicore optical fiber. Distal optics is positioned adjacent to a second end of the multicore optical fiber and is positioned to collect light from a sample of interest so that the collected light from the sample of interest is coupled to the plurality of optical cores in the multicore optical fiber.

24 Claims, 50 Drawing Sheets

Related U.S. Application Data

(60) Provisional application No. 62/004,255, filed on May 29, 2014, provisional application No. 61/838,313, filed on Jun. 23, 2013.

(51) Int. Cl.

| | |
|---|---|
| *G01B 9/02* | (2006.01) |
| *G01N 21/39* | (2006.01) |
| *G01N 21/47* | (2006.01) |
| *G02B 6/02* | (2006.01) |
| *G02B 6/293* | (2006.01) |
| *G01S 7/481* | (2006.01) |
| *G01S 17/89* | (2020.01) |
| *G02F 1/29* | (2006.01) |
| *H04B 10/61* | (2013.01) |

(52) U.S. Cl.
CPC ..... *G01B 9/02051* (2013.01); *G01B 9/02069* (2013.01); *G01B 9/02091* (2013.01); *G01N 21/39* (2013.01); *G01N 21/4795* (2013.01); *G01S 7/4812* (2013.01); *G01S 17/89* (2013.01); *G02B 6/02042* (2013.01); *G02B 6/29302* (2013.01); *G02F 1/292* (2013.01); *A61B 2562/0233* (2013.01); *G01B 2290/70* (2013.01); *G01N 2021/1787* (2013.01); *H04B 10/61* (2013.01)

(56) References Cited

U.S. PATENT DOCUMENTS

| | | | |
|---|---|---|---|
| 5,465,147 A | 11/1995 | Swanson | |
| 5,956,355 A | 9/1999 | Swanson | |
| 6,134,003 A | 10/2000 | Tearney | |
| 6,160,826 A | 12/2000 | Swanson | |
| 6,191,862 B1 | 2/2001 | Swanson | |
| 6,288,784 B1 | 10/2001 | Hitzenberger | |
| 6,445,939 B1 | 9/2002 | Swanson | |
| 6,485,413 B1 | 11/2002 | Boppart | |
| 6,501,551 B1 | 12/2002 | Tearney | |
| 6,564,087 B1 | 5/2003 | Pitris | |
| 6,891,984 B2 | 5/2005 | Petersen | |
| 7,061,618 B2 | 6/2006 | Walid | |
| 7,447,408 B2* | 11/2008 | Bouma | G02B 6/02042 385/123 |
| 7,530,948 B2 | 5/2009 | Seibel | |
| 7,623,907 B2* | 11/2009 | Takaoka | A61B 5/0084 250/222.2 |
| 7,843,572 B2 | 11/2010 | Tearney et al. | |
| 7,864,822 B2 | 1/2011 | Bouma | |
| 7,916,387 B2 | 3/2011 | Schmitt | |
| 8,078,245 B2 | 12/2011 | Daly | |
| 8,384,909 B2 | 2/2013 | Yun | |
| 8,416,818 B2 | 4/2013 | Bouma | |
| 8,437,007 B2 | 5/2013 | Flanders | |
| 8,515,221 B2 | 8/2013 | Flanders | |
| 8,690,330 B2 | 4/2014 | Hacker et al. | |
| 8,711,364 B2 | 4/2014 | Brennan | |
| 8,854,629 B2 | 10/2014 | Frisken | |
| 8,947,648 B2 | 2/2015 | Swanson | |
| 8,994,954 B2 | 3/2015 | Minneman | |
| 9,008,142 B2 | 4/2015 | Minneman | |
| 9,044,164 B2 | 6/2015 | Hacker et al. | |
| 9,122,016 B2* | 9/2015 | Takaoka | A61B 1/00096 |
| 9,162,404 B2 | 10/2015 | Doerr | |
| 9,464,883 B2 | 10/2016 | Swanson et al. | |
| 9,683,928 B2 | 6/2017 | Swanson | |
| 10,107,616 B2 | 10/2018 | Zhou | |
| 10,132,610 B2 | 11/2018 | Swanson et al. | |
| 10,401,883 B2 | 9/2019 | Swanson et al. | |
| 10,416,288 B2 | 9/2019 | Swanson | |
| 2006/0187537 A1 | 8/2006 | Huber et al. | |
| 2008/0304074 A1* | 12/2008 | Brennan, III | A61B 5/0066 356/451 |
| 2011/0109898 A1* | 5/2011 | Froggatt | G01M 11/31 356/73.1 |
| 2011/0128532 A1* | 6/2011 | Taira | G01J 9/04 356/218 |
| 2011/0218404 A1* | 9/2011 | Hirakawa | A61B 1/00165 600/178 |
| 2012/0099112 A1* | 4/2012 | Alphonse | G01B 9/02044 356/479 |
| 2012/0226118 A1 | 9/2012 | Delbeke et al. | |
| 2013/0209022 A1 | 8/2013 | Doerr | |
| 2014/0126902 A1 | 5/2014 | Swanson | |
| 2014/0126990 A1 | 5/2014 | Swanson | |
| 2014/0147079 A1 | 5/2014 | Doerr | |
| 2014/0160488 A1 | 6/2014 | Zhou | |
| 2014/0376000 A1 | 9/2014 | Swanson | |
| 2016/0357007 A1* | 12/2016 | Swanson | G02B 23/26 |
| 2017/0143196 A1 | 5/2017 | Liang et al. | |
| 2017/0205253 A1 | 7/2017 | Handerek | |

FOREIGN PATENT DOCUMENTS

| | | |
|---|---|---|
| EP | 0883793 | 11/2007 |
| EP | 1839375 | 4/2014 |
| WO | 2012088361 | 6/2012 |

OTHER PUBLICATIONS

Wissem Sfar Zaoui, María Félix Rosa, Wolfgang Vogel, Manfred Berroth Jörg Butschke, and Florian Letzkus, "Cost-effective CMOS-compatible grating couplers with backside metal mirror and 69% coupling efficiency", Optics Express, vol. 20, No. 26, Dec. 10, 2012.

Vilson R. Almeida, Roberto R. Panepucci, and Michal Lipson, "Nanotaper for compact mode conversion", Optics Letters, vol. 28, No. 15, Aug. 1, 2003.

Anatol Khilo, Miloš A. Popović, Mohammad Araghchini, and Franz X. Kärtner, "Efficient planar fiber-to-chip coupler based on two-stage adiabatic evolution", Optics Express, vol. 18, No. 15, Jul. 19, 2010.

Long Chen, Christopher R. Doerr, Young-Kai Chen, and Tsung-Yang Liow, "Low-Loss and Broadband Cantilever Couplers Between Standard Cleaved Fibers and High-Index-Contrast Si3N4 or Si Waveguides", IEEE Photonics Technology Letters, vol. 22, No. 23, Dec. 1, 2010.

Alan Y. Liu, Chong Zhang, Justin Norman, Andrew Snyder, Dmitri Lubyshev,Joel M. Fastenau, Amy W. K. Liu, Arthur C. Gossard, and John E. Bowers, "High performance continuous wave 1.3 Im quantum dot lasers on silicon", Applied Physics Letters,104, 041104 (2014.

Jie Sun, Erman Timurdogan, Ami Yaacobi, Zhan Su, Ehsan Shah Hosseini, David B. Cole, and Michael R. Watts, "Large-Scale Silicon Photonic Circuits for Optical Phased Arrays", IEEE Journal of Selected Topics in Quantum Electronics, vol. 20, No. 4, Jul./Aug. 2014.

Jie Sun, Ehsan Shah Hosseini, Ami Yaacobi, David B. Cole, Gerald Leake, Douglas Coolbaugh, and Micheael R. Watts, "Two-dimensional apodized silicon photonic phased arrays", Optics Letters, vol. 39, No. 2, Jan. 15, 2014.

C. T. DeRose, R. D. Kekatpure, D. C. Trotter, A. Starbuck. J. R. Wendt, A. Yaacobi, M. R. Watts, U. Chettiar, N. Engheta, and P. S. Davids, "Electronically controlled optical beam-steering by an active phased array of metallic nanoantennas", Optics Express, vol. 21, No. 4, Feb. 25, 2013.

Jie Sun, Erman Timurdogan, Ami Yaacobi, Ehsan Shah Hosseini, and Michel R. Watts, "Large-scale nanophotonic phased array", Nature, vol. 493, Jan. 10, 2013.

Ami Yaacobi Erman Timurdogan, and Michael R. Watts, "Vertical emitting aperture nanoantennas", Optics Letters, vol. 37, No. 9, May 1, 2012.

J. K. Doylend, M. J. R. Heck, J. T. Bovington, J. D. Peters, L. A. Coldre, and J. E. Bowers, "Two-dimensional free-space beam steering with an optical phased array of silicon-on-insulator", Optics Express, vol. 19, No. 22, Oct. 24, 2011.

(56) References Cited

OTHER PUBLICATIONS

Karel Van Acoleyen, Hendrick Rogier, and Roel Baets, "Two-dimensional optical phased array antenna on silicon-on-insulator", Optics Express, vol. 18, No. 13, Jun. 21, 2010.
James A. Burns, Brian F. Aull, Chenson K. Chen, Chang-Lee Chen, Craig L. Keast, Jeffrey M. Knecht, Vyshanavi Suntharalingam, Keith Warner, Peter W. Wyatt, and Donna-Ruth W. Yost, "A Wafer-Scale 3-D Circuit Integration Technology", IEEE Transactions on Electronic Devices, vol. 53, No. 10, Oct. 2006.
Dirk Lorenser, C. Christian Singe, Andrea Curatolo, and David D. Sampson, "Energy-efficient low-Fresnel-number Bessel beams and their application in optical coherence tomography", Optics Letters, vol. 39, No. 3, Feb. 1, 2014.
Niklas Weber, Dominik Spether, Andreas Seifert, and Hans Zappe, "Highly compact imaging using Bessel beams generated by ultraminiaturized multi-micro-axicon systems", Journal of Optical Society of America A. vol. 29, No. 5, May 2012.
Z. Xie, B. Armbruster, and T. Grosjean, "Axicon on a gradient index lens (AXIGRIN)): integrated otial bench for Bessel beam generation from a point-like source", Applied Optics, vol. 53, Issue 26, (2014).
G.S. Sokolovskii, V.V. Dudelev, S.N. Losev, K.K. Soboleva, A.G. Deryagin, K.A. Fedorovac, V.I. Kuchinskii, W. Sibbett, E.U. Rafailov, "Bessel beams from semiconductor light sources", Progress in Quantum Electronics, vol. 38, No. 4, Jul. 2014.
F. Merola ; S. Coppola ; V. Vespini ; S. Grilli ; P. Ferraro ; D. Balduzzi ; A. Galli ; R. Puglisi, "Fabrication and test of polymeric microaxicons", Proceedings of the SPIE, doi:10.1117/12.922572, Jun. 1, 1012.
Paul Steinvurzel, Khwanchai Tantiwanichapan, Masao Goto, and Siddharth Ramachandran, "Fiber-based Bessel beams with controllable diffraction-resistant distance", Optics Letters, vol. 36, No. 23, 2011.
Cedric Blatter ; Branislav Grajciar ; Christoph M. Eigenwillig; Wolfgang Wieser; Benjamin R. Biedermann; Robert Huber; Rainer A. Leitgeb, "High-speed functional OCT with self-reconstructive Bessel illumination at 1300 nm", Proceedings of the SPIE, doi:10.1117/12.889669, Jun. 1, 2011.
S. Yun, G. Tearney, J. de Boer, and B. E. Bouma, "Removing the depth-degeneracy in optical frequency domain imaging with frequency shifting," Opt. Express 12(20), 4822-4828 (2004).
B. J. Vakoc, S. H. Yun, G. J. Tearney, and B. E. Bouma, "Elimination of depth degeneracy in optical frequency-domain imaging through polarization-based optical demodulation," Opt. Lett. 31(3), 362-364 (2006).
M. Siddiqui, S. Tozburun, E. Z. Zhang, and B. J. Vakoc, "Compensation of spectral and RF errors in swept-source OCT for high extinction complex demodulation," Opt. Express 23, 5508-5520 (2015).
K.-S. Lee, P. Meemon, W. Dallas, K. Hsu, and J. P. Rolland, "Dual detection full range frequency domain optical coherence tomography," Opt. Lett. 35(7), 1058-1060 (2010).
B. Hofer, B. Považay, B. Hermann, A. Unterhuber, G. Matz, and W. Drexler, "Dispersion encoded full range frequency domain optical coherence tomography," Opt. Express 17(1), 7-24 (2009).
T.-H. Tsai, B. Potsaid, Y. K. Tao, V. Jayaraman, J. Jiang, P. J. S. Heim, M. F. Kraus, C. Zhou, J. Hornegger, H. Mashimo, A. E. Cable, and J. G. Fujimoto, "Ultrahigh speed endoscopic optical coherence tomography using micromotor imaging catheter and VCSEL technology," Biomed. Opt. Express 4(7), 1119-1132 (2013).
B. Baumann, W. Choi, B. Potsaid, D. Huang, J. S. Duker, and J. G. Fujimoto, "Swept source Fourier domain polarization sensitive optical coherence tomography with a passive polarization delay unit," Opt. Express 20(9), 10229-10241 (2012).
Z. Wang, H.-C. Lee, O. O. Ahsen, B. Lee, W. Choi, B. Potsaid, J. Liu, V. Jayaraman, A. Cable, M. F. Kraus, K. Liang, J. Hornegger, and J. G. Fujimoto, "Depth-encoded all-fiber swept source polarization sensitive OCT," Biomed. Opt. Express 5(9), 2931-2949 (2014).
B. H. Park, M. C. Pierce, B. Cense, and J. F. de Boer, "Jones matrix analysis for a polarization-sensitive optical coherencetomography system using fiber-optic components," Opt. Lett. 29(21), 2512-2514 (2004).
H. Pahlevaninezhad, A. Lee, L. Cahill, S. Lam, C. MacAulay, and P. Lane, "Fiber-Based Polarization Diversity Detection for Polarization-Sensitive Optical Coherence Tomography," Photonics 1(4), 283-295 (2014).
T. S. Ralston, D. L. Marks, P. S. Carney, and S. A. Boppart, "Interferometric synthetic aperture microscopy," Nat. Phys. 3(2), 129-134 (2007).
U. Morgner, W. Drexler, F. Kärtner, X. Li, C. Pitris, E. Ippen, and J. G. Fujimoto, "Spectroscopic optical coherence tomography," Opt. Lett. 25(2), 111-113 (2000).
R. Huber, M. Wojtkowski, J. G. Fujimoto, J. Y. Jiang, and A. E. Cable, "Three-dimensional and C-mode OCT imaging with a compact, frequency swept laser source at 1300 nm," Optics Express 13(26), 10523-10538 (2005).
R. Huber, M. Wojtkowski, K. Taira, J. G. Fujimoto, and K. Hsu, "Amplified, frequency swept lasers for frequency domain reflectometry and OCT imaging: design and scaling principles," Optics Express 13(9), 3513-3528 (2005).
B. Potsaid, I. Gorczynska, V. J. Srinivasan, Y. L. Chen, J. Jiang, A. Cable, and J. G. Fujimoto, "Ultrahigh speed spectral / Fourier domain OCT ophthalmic imaging at 70,000 to 312,500 axial scans per second," Optics Express 16 (19), 15149-15169 (2008).
Marinko V. Sarunic, Brian E. Applegate, and Joseph A. Izatt, "Real-time quadrature projection complex conjugate resolved Fourier domain optical coherence Tomography", Optics Letters, vol. 31, No. 16, Aug. 15, 2006.
Jiefeng Xi, Li Huo, Jiasong Li and Xingde Li, "Generic real-time uniform K-space sampling method for high-speed swept-Source optical coherence tomography", Optics Express, vol. 18, No. 9, Apr. 26, 2010.
V. Jayaraman, G.D. Cole, M. Robertson, C. Burgner, D. John, A. Uddin and A. Cable, "Rapidly swept, ultra-widely-tunable 1060 nm MEMS-VCSELs", Electronics Letters, Oct. 11, 2012 vol. 48 No. 21.
G. J. Tearney, R. H. Webb, and B. E. Bouma, "Spectrally Encoded Confocal Microscopy", Optics Letters, vol. 23, No. 15, Aug. 1, 1998.
Chen D. Lu, Martin F. Kraus, Benjamin Potsaid, Jonathan J. Liu, WooJhon Choi, Vijaysekhar Jayaraman, Alex E. Cable, Joachim Hornegger, Jay S. Duker and James G. Fujimoto, "Handheld ultrahigh speed swept source optical coherence tomography instrument using a MEMs scanning mirror", Biomedical Optics Express, vol. 5, No. 1, Jan. 1, 2014.
V. D. Nguyen, N. Weiss, W. Beeker, M. Hoekman, A. Leinse, R. G. Heideman, T. G. van Leeuwen, and J. Kalkman, "Integrated-optics-based swept-source optical coherence tomography," Opt. Lett. 37(23), 4820-4822 (2012).
B. I. Akca, V. Nguyen, J. Kalkman, N. Ismail, G. Sengo, S. Fei, A. Driessen, T. G. van Leeuwen, M. Pollnau, K. Worhoff, and R. M. de Ridder, "Toward Spectral-Domain Optical Coherence Tomography on a Chip," IEEE J. Sel. Top. Quantum Electron. 18(3), 1223-1233 (2012).
V. D. Nguyen, B. I. Akca, K. Wörhoff, R. M. De Ridder, M. Pollnau, T. G. van Leeuwen, and J. Kalkman, "Spectral domain optical coherence tomography imaging with an integrated optics spectrometer," Opt. Lett. 36, 1293-1295 (2011).
G. Yurtsever, B. Považay, A. Alex, B. Zabihian, W. Drexler, and R. Baets, "Photonic integrated Mach-Zehnder interferometer with an on-chip reference arm for optical coherence tomography," Biomed. Opt. Express 5(4), 1050-1061 (2014).
G. Yurtsever, N. Weiss, J. Kalkman, T. G. van Leeuwen, and R. Baets, "Ultra-compact silicon photonic integrated interferometer for swept-source optical coherence tomography," Opt. Lett. 39(17), 5228-5231 (2014).
B. I. Akca, B. Povazay, A. Alex, K. Worhoff, R. M. de Ridder, W. Drexler, and M. Pallnau, "Miniature spectrometer and beam splitter for an optical coherence tomography on a silicon chip", Optics Express, vol. 31, No. 14, Jul. 3, 2014.

(56) References Cited

OTHER PUBLICATIONS

Kyle Preston, Arthur Nitkowski, Nicolás Sherwood-Droz, Andrew Berkeley, Bradley S. Schmid, and Arsen R. Hajian, OCTANE: Optical Coherence Tomography Advanced Nanophotonic Engine, CLEO 2013 Technical Digest, Paper AW31.5, Jun. 9-14, 2013.
Daniel Neill, Luke Stewart, Huiping Li, Tom Killin, Fan Chen, Steve Frisken, Glenn Baxter, Simon Poole, "Compact polarization diverse receiver for biomedical imaging Applications", SPIE Proceedings, vol. 7891, Jan. 22, 2011.
Arthur Nitkowski, Kyle Preston, Nicolás Sherwood-Droz, Andrew Berkeley, Bradford B. Behr, Bradley S. Schmidt, and Arsen R. Hajian, "Nano Spectrometer for Optical Coherence Tomography", Imaging and Applied Optics Conference, Paper AM1B.3, (2013).
B. Imran Akca, "Spectral-Domain Optical Coherence Tomography on a Silicon Chip", PhD Thesis. University of Twente, (2012).
D. Culemann, A. Knuettel, and E. Voges, "Integrated optical sensor in glass for optical coherence tomography," IEEE J. Sel. Topics Quantum Electron., vol. 6, No. 5, pp. 730-734, Oct. 2000.
E. Margallo-Balbas,M. Geljon, G. Pandraud, and P. J. French, "Miniature 10 kHz thermo-optic delay line in silicon," Opt. Lett., vol. 35, No. 23, pp. 4027-4029, Dec. 2010.
B. Imran Akca, Markus Pollnau, Kerstin Worhoff, Rene M. De Ridder, "Silicon Oxynitride Technology for Integrated Optical Solutions in Biomedical Applications", In: 13th International Conference on Transparent Optical Networks 2011, Jun. 26-30, 2011, Stockholm, Sweden.
G. Yurtsever, P. Dumon, W. Bogaerts, and R. Baets, "Integrated photonic circuit in silicon on insulator for Fourier domain optical coherence tomography," in Proc. SPIE, Opt. Coherence Tomography Coherence Domain Opt. Methods Biomed. XIV, vol. 7554, San Francisco, CA, 2010, pp. 1-5.
V. D. Nguyen, N. Ismail, F. Sun, K. Worhoff, T. G. van Leeuwen, and J. Kalkman, "SiON integrated optics elliptic couplers for Fizeau-based optical coherence tomography," IEEE J. Lightw. Technol., vol. 28, No. 19, pp. 2836-2842, Sep. 2010.
Haitham Omran, Yasser M. Sabry, Mohamed Sadek, Khaled Hassan, Mohamed Y. Shalaby and Diaa Khalil, "Deeply-Etched Optical MEMS Tunable Filter for Swept Laser Source Applications", IEEE Photonics Technology Letters. vol. 26, No. 1, Jan. 2014.
Firooz Aflatouni, Behrooz Abiri, Angad Rekhi, and Ali Hajimiri, "Nanophotonic coherent imager", Optics Express, vol. 23, No. 4, doi: 10.1364/OE.23.005117, 2015.
Gyeong Cheol Park, Weiqi Xue, Elizaveta Semenova, Kresten Yvind, Jesper Mørk, and Il-Sug Chung, "III-V/SOI Vertical Cavity Laser with In-plane Output into a Si Waveguide", Paper W2A.17, Proceedings of the Optical Fiber Communication Conference, 2015.
K. Worhoff, C. G. H. Roeloffzen, R. M. de Ridder, A. Driessen, and P. V. Lambeck, "Design and application of compact and highly tolerant polarization-independent waveguides," IEEE J. Lightw. Technol., vol. 25, No. 5, pp. 1276-1282, May 2007.
S. K. Selvaraja, W. Bogaerts, P. Absil, D. Van Thourhout, and R. Baets, "Record low-loss hybrid rib/wire waveguides for silicon photonic circuits," Group IV Photonics (2010).
D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon-on-insulator platform," Opt. Express 18(17), 18278-18283 (2010).
D. Vermeulen, S. Selvaraja, P. Verheyen, P. Absil, W. Bogaerts, D. Van Thourhout, and G. Roelkens, "Silicon-on-insulator polarization rotator based on a symmetry breaking silicon overlay," IEEE Photonics Technol. Lett. 24(5), 482 (2012).
A. Mekis, A. Dodabalapur, R. Slusher, and J. D. Joannopoulos, "Two-dimensional photonic crystal couplers for unidirectional light output," Opt. Lett. 25(13), 942-944 (2000).
L. Chen, C. R. Doerr, L. Buhl, Y. Baeyens, and R. A. Aroca, "Monolithically integrated 40-wavelength demultiplexer and photodetector array on silicon," IEEE Photonics Technol. Lett. 23(13), 869-871 (2011).
C. R. Doerr, L. Chen, D. Vermeulen, T. Nielsen, S. Azemati, S. Stulz, G. McBrien, X.-M. Xu, B. Mikkelsen, M. Givehchi, C. Rasmussen, and S. Y. Park, "Single-chip silicon photonics 100-Gb/s coherent transceiver," in Optical Fiber Communication Conference, (Optical Society of America, 2014), Th5C. 1.
M. Izutsu, S. Shikama, and T. Sueta, "Integrated optical SSB modulator/frequency shifter," IEEE J. Quant. Electron., vol. 2, No. 11, pp. 2225-2227, 1981.
D. Talliert, H. Chong, P. I. Borel, L. H. Frandsen, R. M. D. L. Rue, and R. Baets, "A compact two-dimensional grating coupler used as a polarization splitter", IEEE Photon. Tech. Lett., vol. 15, pp. 1249-1251, 2003.
R. Nagarajan and Others, "10 Channel, 100Gbit/s per Channel, Dual Polarization, Coherent QPSK, Monolithic InP Receiver Photonic Integrated Circuit", Optical Fiber Communication Conference Proceedings, p. OML7, 2011.
N. Dupuis, C. R. Doerr, L. Zhang, L. Chen, N. J. Sauer, P. Dong, L. L. Buhl, and D. Ahn, "InP-based comb generator for optical OFDM," J. Lightw. Technol., 2011.
S. Chandrasekhar and Xiang Liu, "Enabling Components for Future High-Speed Coherent Communication Systems", Optical Fiber Communication Conference Tutorial, 2011.
"Office Action" for U.S. Appl. No. 15/147,775, dated Jun. 4, 2018, 7 pages, The USPTO.
"Response to Office Action" for U.S. Appl. No. 15/147,775, filed Jan. 27, 2019, 13 pages.
"Supplemental Response to Office Action" for U.S. Appl. No. 15/147,775, filed Feb. 7, 2019, 14 pages.
Hitzenberger, Christoph K., et at., In Vivo Intraocular Ranging by Wavelength Tuning Interferometry, SPIE, pp. 47-51, vol. 3251, retrieved from: http://proceedings.spiedigitallibrary.org/on Sep. 24, 2013.
Warren L. Stutzman and Gary A. Thiele, "Antena Theory and Design", John Wiley & Sons, ISBN 0-471-04458-X, 1981. Textbook.
Y. Zhao, Z. Chen, C. Saxer, S. Xiang, J.F. de Beor, and J.S. Nelson, "Phase-resolved optical coherence tomography and optical Doppler tomography for imaging blood flow in human skin with fast scanning speed and high velocity sensitivity," Opt. Lett. 25(2), 114-116 (2000).
W. Choi, B. Potsaid, V. Jayaraman, B. Baumann, I. Grulkowski, J. J. Liu, C. D. Lu, A. E. Cable, D. Huang, J. S. Duker, and J. G. Fujimoto, "Phase sensitive swept-source optical coherence tomography imaging of the human retina with a vertical cavity surface-emiting laser light source," Opt. Lett. 38(3), 338-340 (2013).
Youxin Mao, Costel Flueraru, Shoude Chang, Dan P. Popescu, Michael G. Sowa, "Performance analysis of a swept-source optical coherence tomography system with a quadrature interferometer and optical amplification", Optics Communications, vol. 284, Issues 10-11, May 15, 2011.
C.M. Eigenwillig, B. R. Biedermann, G. Palte, and R. Huber, "K-space linear Fourier domain mode locked laser and applications for optical coherence tomography," Optics Express 16(12), 8916-8937 (2008).
"Scanning fiber angle-resolved low coherence interferometry", Yizheng Zhu, Neil G. Terry, and Adam Wax, Optics Letters, vol. 34, No. 20, 2009.
"Size and shape determination of spheroidal scatters using two-dimensional angle resolved scattering", Michael Giacomelli, Yizheng, Zhu, John Lee, Adam Wax, Optics Express, vol. 18, No. 14, 2010.
Humle, J.C. et al., "Fully integrated hybrid silicon free-space beam steering source with 32 channel phased array" International Society for Optics and Photonics (SPIE PW), San Francisco, CA Feb. 1-6, 2014, pp. 898907-1-898907-15.
Kevin Gourley, Ilya Golu, Brahim Chebbi, "First experimental demonstration of a Fresnel Axicon", Proceedings of the SPIE, doi:10.1117/12.807162, Jun. 18, 2008.
Oto Brzobohatý, TomášČižmár, and Pavel Zemánek, "High quality quasi-Bessel beam generated by round-tip axicon", Optics Express, vol. 16, No. 17, 2008.

(56) References Cited

OTHER PUBLICATIONS

"Tapered Mode Multiplexers for Single Mode to Multi Mode Fibre Mode Transitions", S. Yerolatsitis, I. Gris-Sánchez, T. A. Birks, Proceedings of the Optical Fiber Communications Conference, Paper w3B.4, 2015.

"Six mode selective fiber optic spatial multiplexer", A. M. Velazquez-Benitez, J. C. Alvarado, G. Lopez-Galmiche, J. E. Antonio-Lopez, J. Hernández-Cordero, J. Sanchez-Mondragon, P. Sillard, C. M. Okonkwo, and R. Amezcua-Correa, Optics Letters, vol. 40, No. 8, Apr. 15, 2015.

"Selective Excitation of High Order Modes in Few Mode Fibres Using Optical Microfibres", Bernard Oduro, Rand Ismaeel, Timothy Lee and Gilberto Brambilla, Proceedings of the Optical Fiber Communications Conference, Paper M3D.5, 2015.

"Recent Progress in the Development of Few Mode Fiber Amplifiers", S. U. Alam*, Y. Jung, Q. Kang, F. Poletti, J.K. Sahu and D. J. Richardson, Proceedings of the Optical Fiber Communications Conference, Paper Tu3C.1, 2015.

"Photonic-Lantern-Based Mode Multiplexers for Few-Mode-Fiber Transmission", R. Ryf1, N. K. Fontaine1, M. Montoliu, S. Randel1, B. Ercan, H. Chen, S. Chandrasekhar, A. H. Gnauck, S. G. Leon-Saval, J. Bland-Hawthorn, J. R. Salazar-Gil, Y. Sun, R. Lingle, Jr., Proceedings of the Optical Fiber Communications Conference, Paper W4J.2., 2015.

"Mode-selective photonic lanterns for space division multiplexing", Sergio G. Leon-Saval, Nicolas K. Fontaine, Joel R. Salazar-Gil, Burcu Ercan, Roland Ryf, and Joss Bland-Hawthorn, Optics Express, vol. 22, No. 1 Jan. 13, 2014.

"Design Constraints of Photonic-Lantern Spatial Multiplexer Based on Laser-Inscribed 3-D Waveguide Technology", Haoshuo Chen, Nicolas K. Fontaine, Roland Ryf, Binbin Guan, S. J. Ben Yoo, and Ton (A. M. J.) Koonen, Journal of Lightwave Technology, vol. 33, No. 6, Mar. 15, 2015.

"Compact spatial multiplexers for mode division multiplexing", Haoshuo Chen, Roy van Uden, Chigo Okonkwo, and Ton Koonen, Optics Express, vol. 22, No. 26, Dec. 26, 2014.

"Optical coherence tomography system mass producible on a silicon photonic chip", Simon Schneider, Matthias Lauermann, Philipp-Immanuel Dietrich, Claudius Weimann, Wolfgang Freude, and Christian Koos, Optics Express, vol. 24, No. 2, Jan. 2016.

"Miniature Optical Coherence Tomography System Based on Silicon Photonics", Eduardo Margallo-Balb'as, Gregory Pandraud and Patrick J. French, SPIE 2Proceedings, vol. 6847 (2008).

Christopher R. Doerr and Lawrence L. Buhl, "Circular Grating Coupler for Creating Focused Azimuthally and Radially Polarized Beams", Optics Letters, vol. 36, No. 7, Apr. 1, 2011.

"Terabit-Scale Orbital Angular Momentum Mode Division Multiplexing in Fibers", Nenad Bozinovic, Yang Yue, Yongxiong Ren, Moshe Tur, Poul Kristensen, Hao Huang, Alan E. Willner, Siddharth Ramachandran, Science Magazine, vol. 340 Jun. 28, 2013.

D. Huang. E. A. Swanson, C. P. Lin, J. S. Schuman, W. G. Stinson, W. Chang, M. R. Hee, t. Flotte, K. Gregory, C. A. Puliafito and J. G. Fujimoto, "Optical coherence tomography," Science 254(5035), 1178-1181 (1991).

R. Leitgeb, C. Hitzenberger, and A. Fercher, "Performance of fourier domain vs. time domain optical coherence tomography," OPt. Express 11(8), 889-894 (2003).

J. F. de Boer, B. Cense, B. H, Park, M. C. Pierce, G. J. Tearney, and B. E. Bouma, "Improved signal-to-noise ratio in spectral-domain compared with time-domain optical coherence tomography," Opt. Lett. 28(21), 2067-2069 (2003).

M. Choma, M. Sarunic, C. Yang, and J. Izatt, "Sensitvity advantage of swept source and fourier domain optical coherence tomography," Opt. Express 11(18), 2183-2189 (2003).

M. Wojtkowski, A, Kowalczyk, R. Leitgeb, and A. F. Fercher, "Full range complex spectral optical coherence tomography technique in eye imaging," Opt. lett. 27(16), 1415-1417 (2002).

A. F. Fercher, C. K. Hitzenberger, G. Kamp, and S. Y. El-Zaiat, "Measurement of intraocular distances by backsattering spectral interferometry," Opt. Commun. 117(1), 43-48 (1995).

S. R. Chinn, E. A. Swanson, and J. G. Fujimoto, "Optical cohoerence tomography using a frequency-tunable optical source," Opt. Lett. 22(5), 340-342 (1997).

S. Yun, G. Tearney, J. de Boer, N. Iftima, and B. Bouma, "High-speed optical frequency-domain imaging," Opt. Express 11(22), 2953-2963 (2003).

R. Huber, M. Wojtkowski, and J.G. Fujimoto, "Fourier Domain Mode Locking (FDML): A new laser operating regime and applications for optical coherence tomography," Opt. Express 14(8), 3225-3237 (2006).

R. Huber, D. C. Adler, and J. G, Fujimoto, "Buffered Fourier domain mode locking: unidirectional swept laser sources for optical coherence tomography imaging at 370,000 lines/s," Opt. Lett.31(20), 2975-2977 (2006).

B. Potsaid, V. Jayaraman, J. G. Fujimoto, J. Jiang, P. J. Heim, and A. E. Cable, "MEMS tunable VCSEL light source for ultrahigh speed 60kHz-1MHz axial scan rate and long range centimeter class OCT imaging," in SPIE BiOS, (International Society for Optics and Photonics), (2012).

V. Jayaraman, G. D. Cole, M. Robertson, A. Uddin, and A. Cable, "High-sweep-rate 1310 nm MEMS-VCSEL with 150 nm continuous tuning range," Electron. Lett. 48(14), 867-869 (2012).

W. Wieser, W. Draxinger, T. Klein, S. Karpf, T. Pfeiffer, and R. Huber, "High definition live 3D-OCT in vivo: design and evaluation of a 4D OCT engine with 1 GVoxel/s," Biomed. Opt. Express 5(9), 2963-2977 (2014).

M.V. Sarunic, B.E. Applegate, and J.Izatt, "Real-Time Quadrature Projection Complex Conjugate Resolved Fourier Domain Optical Coherence Tomography," Optics Letters, vol. 31, No. 16, Aug. 15, 2006.

R. K. Wang, S. L. Jacques, Z. Ma, S. Hurst, S. R. Hanson, and A. Gruber, "Three dimensional optical angiography," Opt. Express 15(7), 4083-4097 (2007).

Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt. Express 20 (4), 4710-4725 (2012).

S. Makita, Y. Hong, M. Yamanari, T. Yatagai, and Y. Yasuno, "Optical coherence angiography," Opt. Express 14(17), 7821-7840 (2006).

S. Yazdanfar, M. Kulkarni, and J. Izatt, "High resolution imaging of in vivo cardiac dynamics using color Doppler optical coherence tomography," Opt. Express 1(13), 424-431 (1997).

B. Vakoc, S. Yun, J. de Boer, G. Tearney, and B. Bouma, "Phase-resolved optical frequency domain imaging," Opt. Express 13(14), 5483-5493 (2005).

M. R. Hee, E. A. Swanson, J. G. Fujimoto, and D. Huang, "Polarization-sensitive low-coherence reflectometer for birefringence characterization and ranging," J. Opt. Soc. Am. B 9(6), 903-908 (1992).

J. F. de Boer and T. E. Milner, "Review of polarization sensitive optical coherence tomography and Stokes vector determination," J. Biomed. Opt. 7(3), 359-371 (2002).

M. Pircher, C. K. Hitzenberger, and U. Schmidt-Erfurth, "Polarization sensitive optical coherence tomography in the human eye," Prog. Retin. Eye. Res. 30(6), 431-451 (2011).

S. K. Nadkarni, M. C. Pierce, B. H. Park, J. F. de Boer, P. Whittaker, B. E. Bouma, J. E. Bressner, E. Halpern, S. L. Houser, and G. J. Tearney, "Measurement of Collagen and Smooth Muscle Cell Content in Atherosclerotic Plaques Using Polarization-Sensitive Optical Coherence Tomography," J. Am. Coll. Cardiol. 49(13), 1474-1481 (2007).

B. R. Biedermann, W. Wieser, C. M. Eigenwillig, T. Klein, and R. Huber, "Dispersion, coherence and noise of Fourier domain mode locked lasers," Opt. Express 17(12), 9947-9961 (2009).

M. Sarunic, M. A. Choma, C. Yang, and J. A. Izatt, "Instantaneous complex conjugate resolved spectral domain and swept-source OCT using 3×3 fiber couplers," Opt. Express 13(3), 957-967 (2005).

R. K. Wang, "In vivo full range complex Fourier domain optical coherence tomography," Appl. Phys. Lett. 90(5), 054103 (2007).

M. Yamanari, S. Makita, Y. Lim, and Y. Yasuno, "Full-range polarization-sensitive swept-source optical coherence tomography by simultaneous transversal and spectral modulation," Opt. Express 18(13), 13964-13980 (2010).

(56) References Cited

OTHER PUBLICATIONS

James G. Fujimoto, Eric Swanson, Robert Huber, European Inventor Award 2017, Jun. 15, 2017, 3 pages. PRWeb.

C. Boudoux, et al., Rapid wavelength-swept spectrally encoded confocal microscopy, Optics Express, Oct. 3, 2005, pp. 8214-8221, vol. 13, No. 20, OSA.

Dongyao Cui, et al., Multifiber angular compounding optical coherence tomography for speckle reduction, Optics Letter, Jan. 1, 2017, pp. 125-128, vol. 42, No. 1, Optical Society of America.

Daniel J. Fechtig, et al., Line-field parallel swept source MHz OCT for structural and functional retinal imaging, Biomedical Optics Express, Mar. 1, 2015, pp. 716-735, vol. 6, No. 3, OSA.

Simon Lemire-Renaud, et al., Double-clad fiber coupler for endoscopy, Optics Express, May 10, 2020, 9755-9764, vol. 18, No. 10, OSA.

Florence Rossant, et al., Highlighting directional reflectance properties of retinal substructures from D-OCT images, IEE Transactions on Biomedical Engineering, Nov. 2019, pp. 3105-3118, vol. 66, No. 11, EMB.

Seon Young Ryu, et al., Combined system of optical coherence tomography and fluorescence spectroscopy based on double-cladding fiber, Optics Letters, pp. 2347-2349, Oct. 15, 2008, vol. 33, No. 20.

Juan Sancho-Dura, et al., Handheld multi-modal imaging for point-of-care skin diagnosis based on akinetic integrated optics optical coherence tomography, Biophotonics Journal, 2018, pp. 1-6, 2018, Wiley-VCH Verlag, GmbH & Co. KGaA Weinheim.

Tuqiang Xie, et al., Fiber-optic-bundle-based optical coherence tomography, Optics Letters, Jul. 15, 2005, pp. 1803-1805, vol. 30, No. 14.

Gunay Yurtsever, et al., Photonic integrated Mach-Zehnder interferometer with an on-chip reference arm for optical coherence tomography, Biomedical Optics Express, Apr. 1, 2014, pp. 1050-1060, vol. 5, No. 4, OSA.

Chao Zhou, et al., Space-division multiplexing optical coherence tomography, Optics Express, Aug. 12, 2013, pp. 19219-19227, vol. 21, No. 16, OSA.

* cited by examiner

Example Specifications
- Center Wavelength ~ 1310 nm
- Scan Range > 100 nm
- Coherence Length > 20 mm
- Sweep Speed > 100 kHz
- Laser Output Power > 25 mW
- Ideal sweep 100% duty cycle sawtooth

FIG. 1B

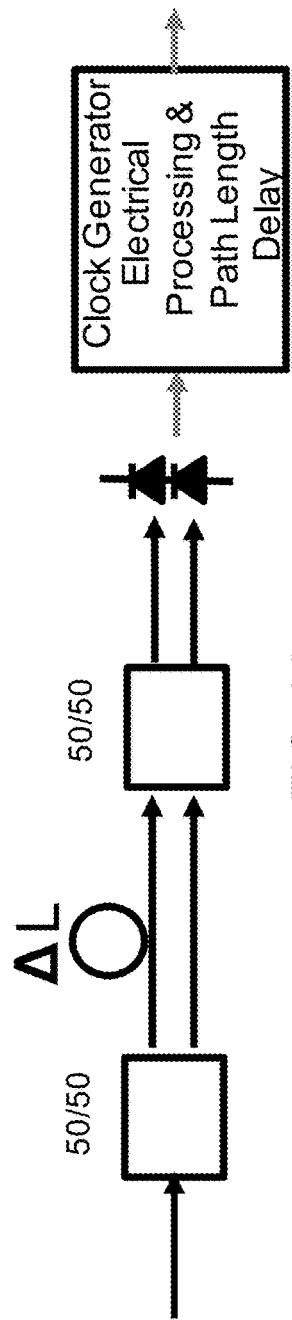
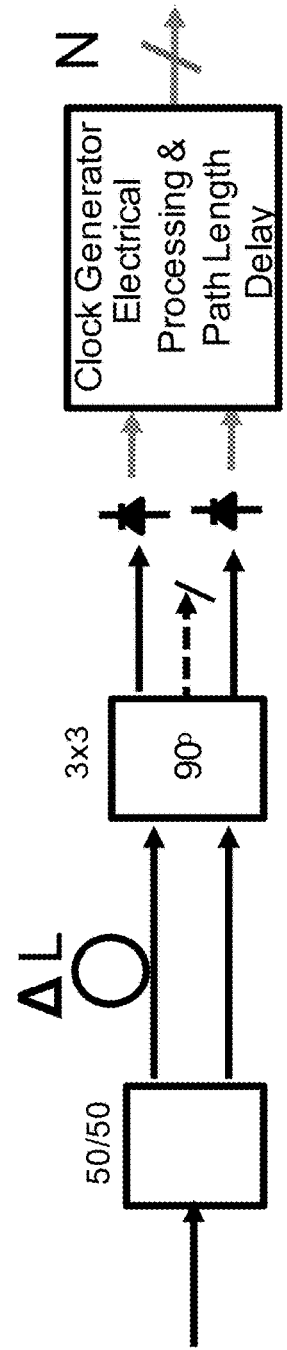
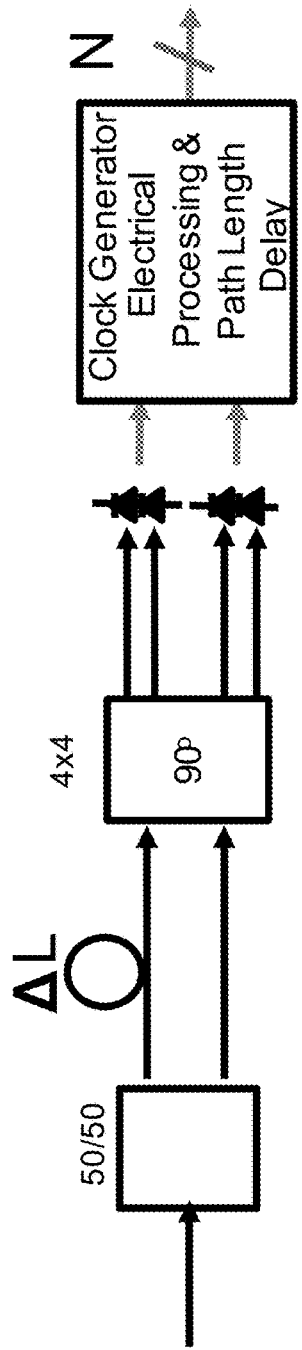
FIG. 8A
FIG. 8B
FIG. 8C

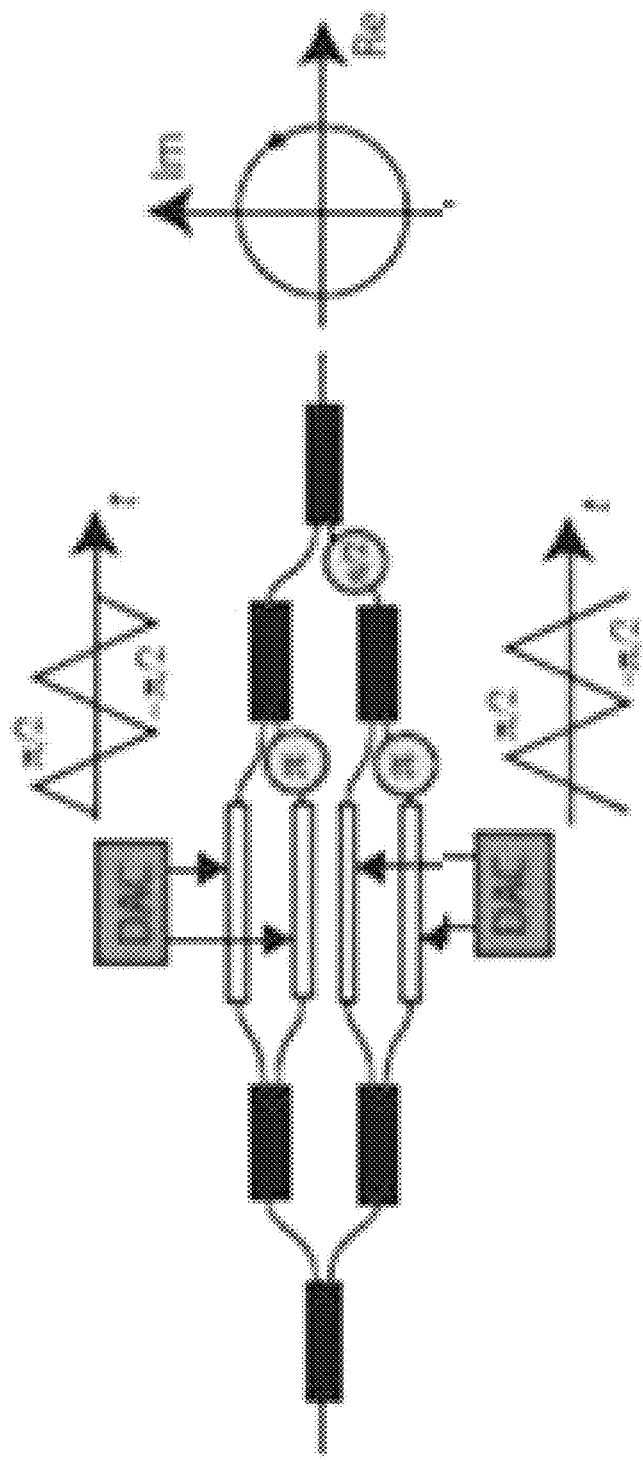

$\Delta f_2 \sim \Delta f_1(1+\Delta L/Lc)$, where $\Delta L \sim$ MZI path length difference and $Lc \sim$ cavity length

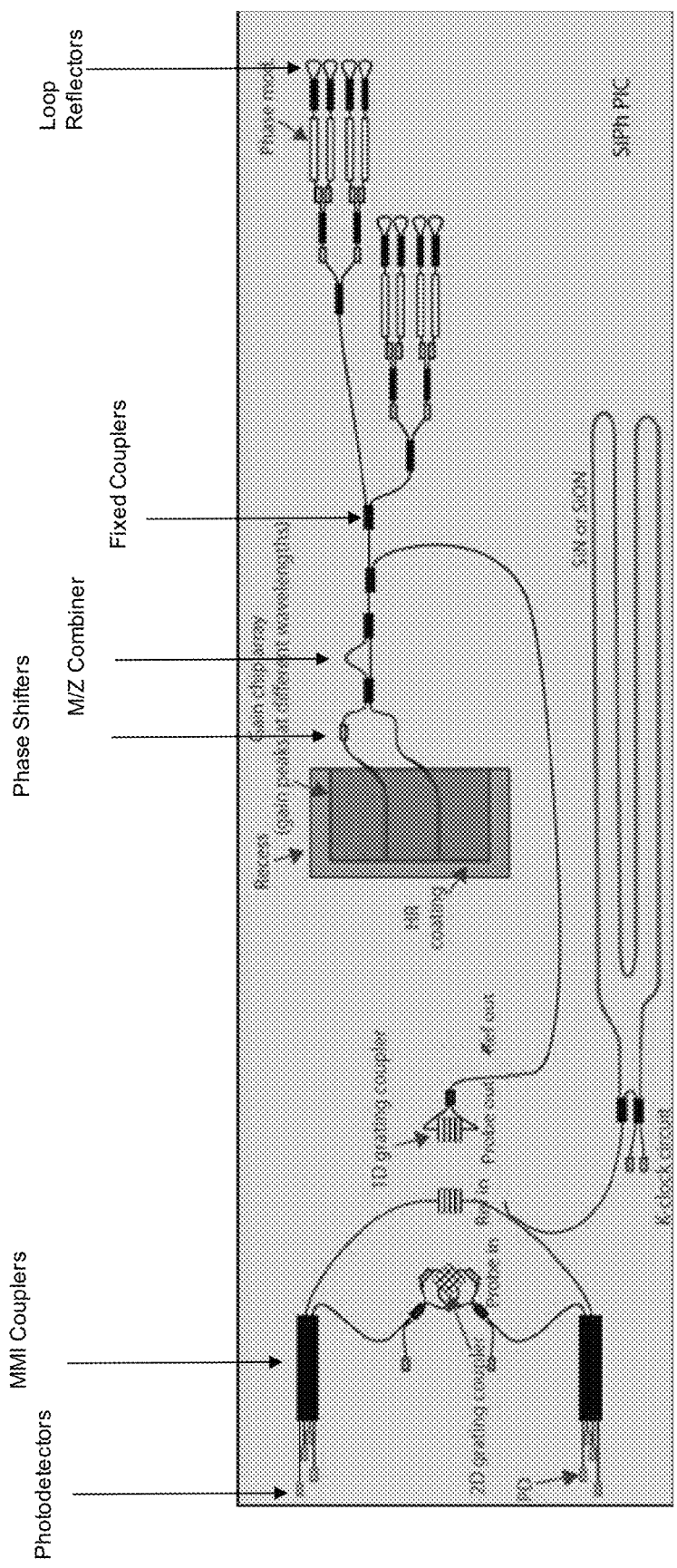
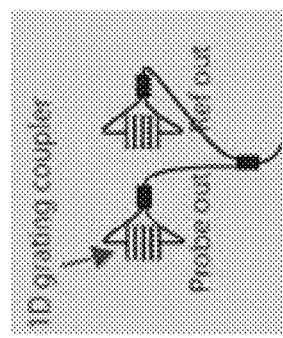
FIG. 18A
FIG. 18B

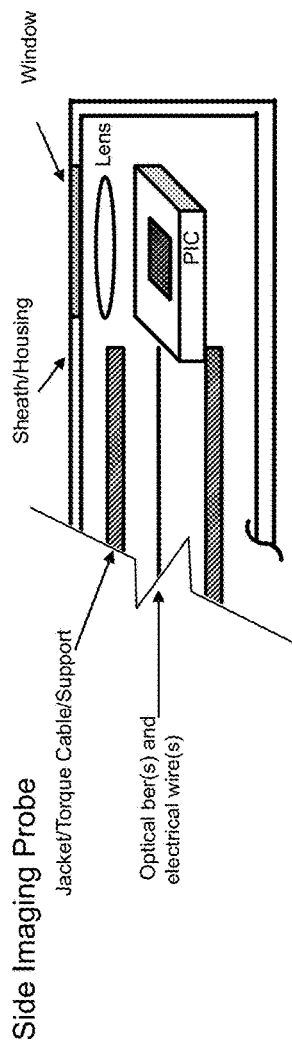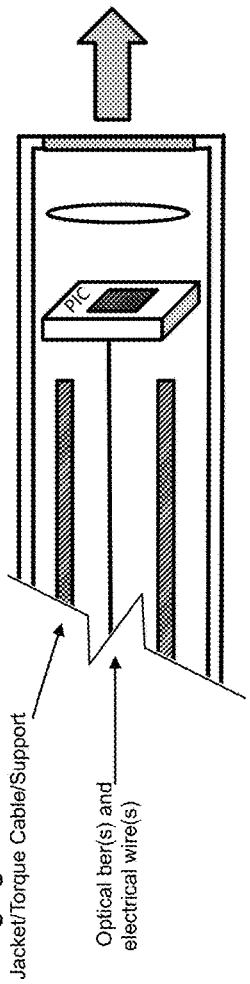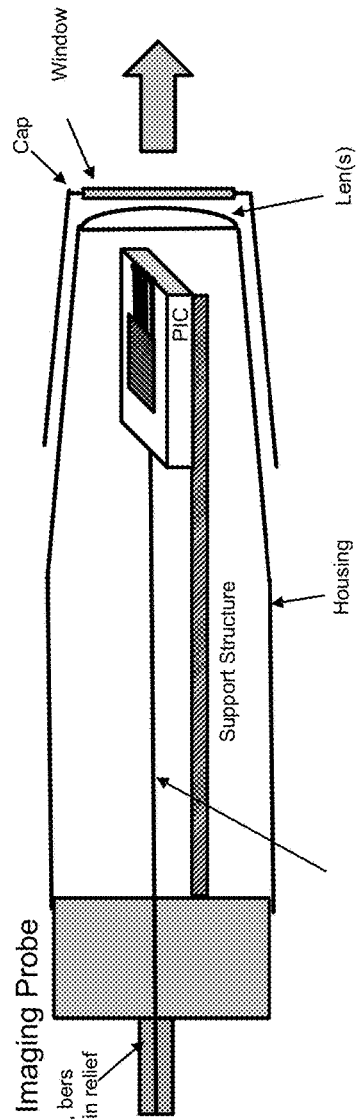

OPTICAL MEASUREMENT SYSTEM USING MULTICORE OPTICAL FIBER

CROSS REFERENCE TO RELATED APPLICATIONS

The present application is a continuation application of U.S. patent application Ser. No. 14/312,621, entitled "Integrated Optical System and Components Utilizing Tunable Optical Sources and Coherent Detection and Phased Array for Imaging, Ranging, Sensing, Communications and Other Applications" filed on Jun. 23, 2014, which claims priority to U.S. Provisional Patent Application No. 62/004,255, entitled "Integrated Optical System and Components Utilizing Tunable Optical Sources and Coherent Detection" filed on May 29, 2014 and also claims priority to U.S. Provisional Patent Application No. 61/838,313, entitled "Integrated Optical System and Components Utilizing Tunable Optical Sources and Coherent Detection", filed on Jun. 23, 2013. The entire contents of U.S. patent application Ser. No. 14/312,621 and U.S. Provisional Patent Application Nos. 62/004,255 and 61/838,313 are herein incorporated by reference.

TECHNICAL FIELD

This disclosure relates generally to technology, designs, and methods applicable to optical imaging, ranging, sensor and communication technology including swept-source optical coherence tomography systems including optional photonic phased arrays.

BACKGROUND

Optical coherence tomography (OCT) is now known to be a minimally invasive optical imaging technique that provides high-resolution, cross-sectional images of tissues and turbid media and which can seamlessly integrates into other diagnostic procedures. OCT can provide real-time images of tissues in situ and can advantageously be used where conventional excisional biopsy is hazardous or impossible, to reduce sampling errors associated with conventional excisional biopsy, or to guide further interventional procedures. Given its exceptional promise, systems and methods for improved OCT, as well as ranging and imaging represent a welcome addition to the art.

Unfortunately prior art OCT systems oftentimes require complex probe module(s) that is used to guide light to/from a sample of interest. Such prior-art systems may employ rotating fibers, or galvanometric or MEMS-driven mirror assemblies or other actuators along with complex optical lens arrangements.

SUMMARY

An advance in the art is made according to an aspect of the present disclosure directed to integrated optical systems, methods and related structures employing tunable optical sources and coherent detection useful—for example—in OCT, ranging and imaging systems that employ integrated photonic phased arrays to overcome a number of limitations of prior-art systems and thereby advance the art.

In contrast to contemporary, prior-art OCT systems and structures that employ simple, fiber optic or miniature optical bench technology using small optical components positioned on a substrate, systems and methods according to the present disclosure employ one or more photonic integrated circuits (PICs), use swept-source techniques, and employ a widely tunable optical source(s) and include multiple functions and in some embodiments all the critical complex optical functions are contained on one or a few photonic integrated circuit(s).

An illustrative structure according to the present disclosure includes an interferometer that divides a tunable optical signal between a reference path and a sample path and combines optical signals returning from the reference path and the sample path to generate an interference signal, said interferometer including a dual polarization, dual-balanced, in-phase and quadrature (I/Q) detection outputs and integrated photodetectors and a detection system that detects the interference signal from which information about a longitudinal reflectivity profile of optical properties of a sample positioned in the sample path may be generated wherein the interferometer and the detection system are all integrated onto a single photonic integrated circuit (PIC). The optical information can eventually be represented in the form of a 1D, 2D, or 3D image. The detection system can be simple (e.g. a transimpedance amplifier (TIA)) or can include more complex electrical signal processing.

Further aspects of this illustrative structure according to an aspect of the present disclosure further includes a tunable optical source system that generates the tunable optical signal and/or a k-clock module for generating a k-clock signal for triggering the detector system wherein the k-clock, the interferometer, the tunable optical source system and the detection system are all integrated onto the PIC.

Finally, additional illustrative structures according to the present disclosure employ an integrated electro-optic phased array. The phased array may be static and used to guide light to/from a probe module and sample. Advantageously, the phase(s) and amplitude(s) of antenna elements may be such that desired focusing is achieved. Another aspect of the present disclosure—includes compensating for any aberrations in the optical path. As may be readily appreciated, such aberrations may arise from a catheter or endoscope or other material.

The phased array according to one aspect of the present disclosure may be advantageously used to achieve an extended depth of field over that normally encountered in a Gaussian Axial/longitudinal field profile. The phase array according to the present disclosure may also be active and enable scanning in 1 or 2 angular or lateral dimensions and may also be used to adjust a focal depth. Finally, the phased array according to the present disclosure may be integrated with one or more of the following structures including a tunable laser, k-clock, electro-optical receiver, delay line and can also be a standalone element.

BRIEF DESCRIPTION OF THE DRAWING

A more complete understanding of the present disclosure may be realized by reference to the accompanying drawings in which:

FIG. 1B illustrates example system specifications;

FIG. 8A shows a schematic block diagram of an embodiment of a k-clock system according to an aspect of the present disclosure;

FIG. 8B shows a schematic block diagram of an embodiment of a k-clock system according to an aspect of the present disclosure;

FIG. 8C shows a schematic block diagram of an embodiment of a k-clock system according to an aspect of the present disclosure;

FIG. 11A show a schematic block diagrams illustrating a methods for achieving a frequency shift as compared with that shown in FIG. 9C and according to an aspect of the present disclosure;

FIG. 18A shows a schematic block diagram illustrating a silicon PIC having an embedded gain chip and surface grating couplers and multiple phase modulators that can act as separate frequency shifters or impart other optical modulation within the laser cavity including one output surface grating coupler according to an aspect of the present disclosure;

FIG. 18B shows a schematic block diagram illustrating a silicon PIC having an embedded gain chip and surface grating couplers and multiple phase modulators that can act as separate frequency shifters or impart other optical modulation within the laser cavity including two output surface grating couplers according to an aspect of the present disclosure;

FIG. 33A shows an illustrative example of the photonic phased array inside an optical probe showing facet input coupling and phased array operation so as to direct light away from the plane of the photonic chip in a side imaging probe;

FIG. 33B shows an illustrative example of the photonic phased array inside an optical probe showing surface input coupling from a backside thinning and phased array operation so as to direct light away from the plane of the photonic chip in a forward imaging probe;

FIG. 33C shows an illustrative example of the photonic phased array inside an optical probe showing facet input coupling and 1D phased array facet output coupling in a hand-held imaging probe;

DETAILED DESCRIPTION

Figure 1A:
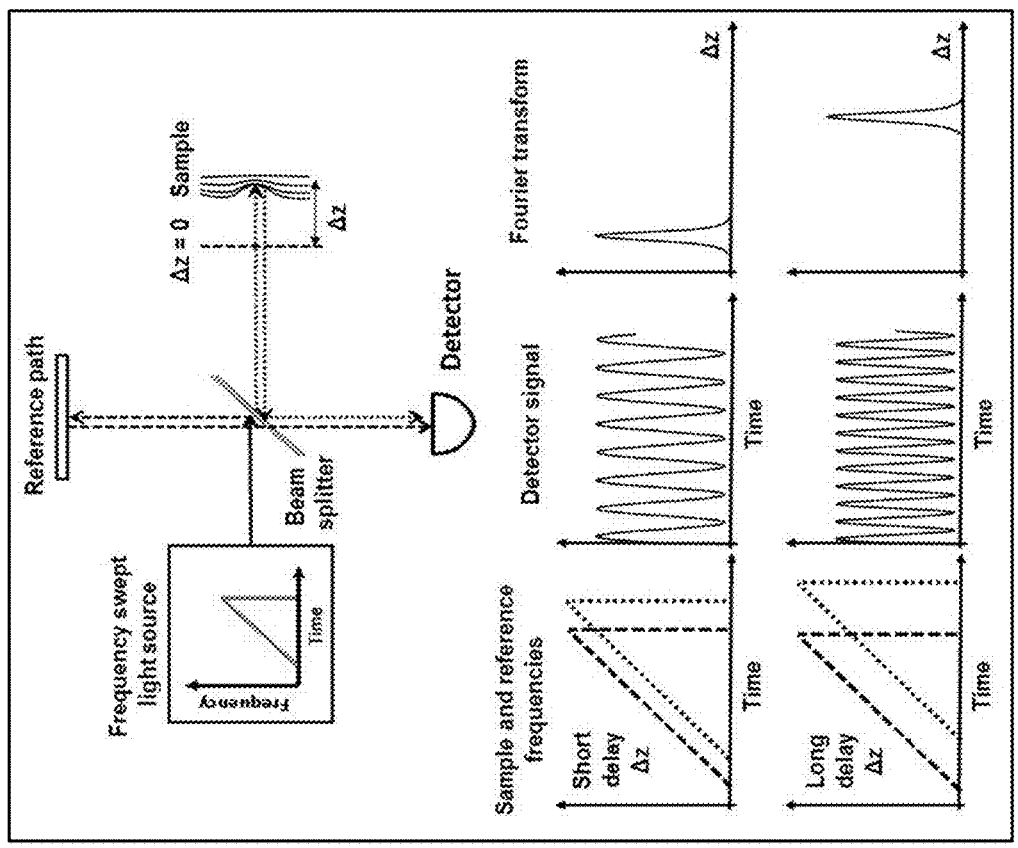
FIG. 1A shows a schematic diagram illustrating a swept-source OCT concept.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not be shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, state transition diagrams, pseudocode, and the like represent various processes which may be substantially represented in computer readable medium and so executed by a computer or processor, whether or not such computer or processor is explicitly shown.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

More specifically, much of the discussion that follows is presented with respect to a swept-source optical coherence tomography system. However, those skilled in the art will readily appreciate that this discussion is broadly applicable to a wide range of applications that employ on a swept laser (or other optical sources that may be rapidly swept over a wide frequency range) and interferometric electro-optical detection, for example, ranging, medical imaging, non-destructive evaluation and testing, laser radar, spectroscopy, and communications—among others.

Turning now to FIGS. 1(a)-1(d), and in particular FIG. 1(a), there is shown a schematic of the axial imaging component of an optical coherence tomography arrangement including a swept-source according to an aspect of the present disclosure. More particularly in that FIG. 1(a), a frequency swept light source is coupled to a Michelson interferometer which comprises two optical paths or "arms". Those skilled in the art will appreciate that while a Michelson interferometer is shown in the illustrative examples described herein other types of interferometers are also possible and are contemplated by this disclosure.

One arm of the Michelson interferometer comprises a reference optical path having a mirror which reflects light and the other arm comprises a sample optical path into which is positioned a sample whose axial/longitudinal reflectivity profile is to be measured. Operationally, light collected from both the reference and sample paths are interferometrically combined and directed to a photodetector (including subsequent signal processing not specifically shown). Due to a delay between reference and sample reflections, interferometric detection and frequency sweep of a laser light source, the photodetector output includes information about the axial/longitudinal reflectivity profile of the sample that may be advantageously extracted by Fourier Transform (FT) techniques or other techniques as known in the art. As may be readily appreciated, a number of architectures and arrangements applying these broad techniques are possible. Exemplary and/or illustrative architectures and arrangements are contemplated and presented by this disclosure.

More particularly, other types of swept-source, optical coherence tomography (SS-OCT) system topologies that are known in the art are contemplated by this disclosure. With reference to FIG. 1(b), there are shown exemplary, illustrative specifications for systems constructed according to aspects of the present disclosure. In particular, center wavelength(s)~1310 nm; Scan Range(s)>100 nm; Coherence Length(s)>20 mm; Sweep Speed(s)>100 kHz; Laser Output Power(s)>25 mW; and Ideal Sweep(s) exhibiting 100% duty cycle sawtooth—are all (as well as others) are contemplated by this disclosure. Note that these exemplary, illustrative specifications are in no way limiting. It is understood and those skilled in the art will readily appreciate that there are a wide variety of other specifications contemplated such as different center wavelength(s), sweep speed(s), etc., contemplated by this disclosure as well.

Figure 1C:
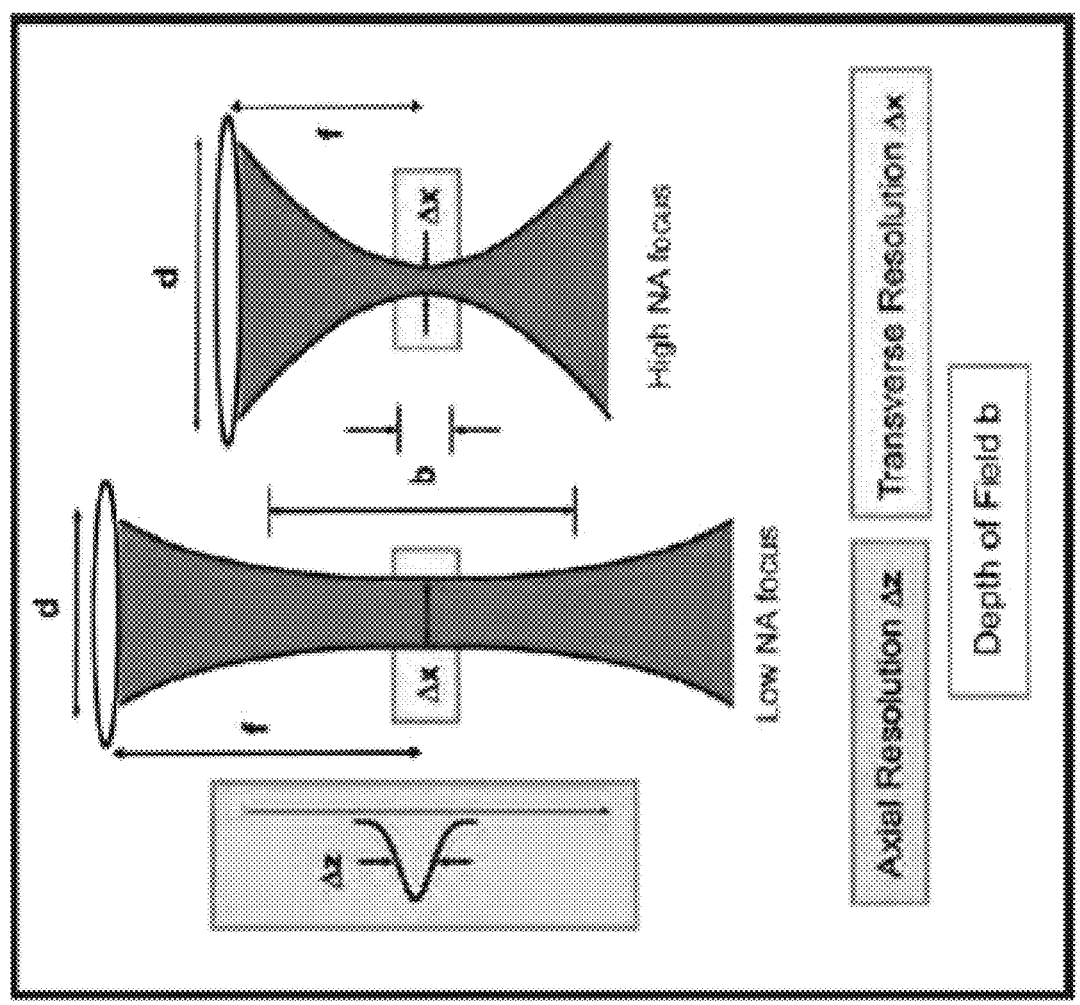
FIG. 1C illustrates axial and lateral resolution.

With reference to FIG. 1(c), there it depicts in schematic form an aspect of contemporary SS-OCT systems namely, that the longitudinal resolution of such systems is substantially dictated by properties of the optical source (i.e., its spectral bandwidth) and the focusing properties of light onto/into the sample. More particularly, the schematic diagram of FIG. 1(c) shows interrelationships between axial resolution, transverse resolution, depth of field as they relate to systems exhibiting low numerical aperture focus (NA) and high NA focus. As may be appreciated, for many contemporary OCT systems, it is the optical spectral bandwidth of the source that is the limiting factor of its longitudinal resolution.

Figure 1D:
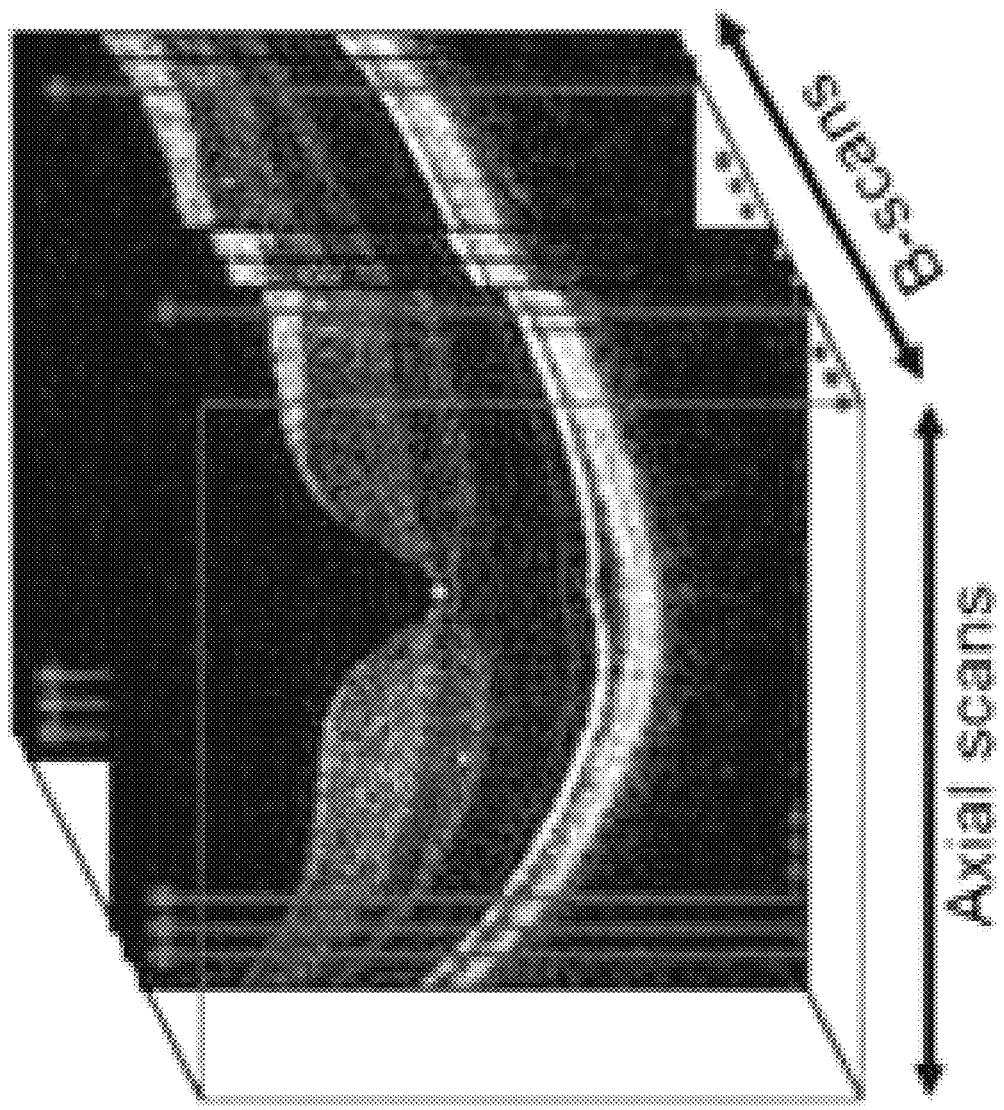
FIG. 1D illustrates 1D, 2D, and 3D imaging from a series of axial scans according to an aspect of the present disclosure.

FIG. 1(d) shows one example in schematic form of how 1D, 2D, 3D images may be constructed by combining axial/longitudinal scanning from a laser source frequency sweep and Fourier transform processing along with lateral or rotational scanning of light onto a sample via a probe module (not specifically shown) as performed by contemporary systems. One can then implement lateral, rotational, or transverse scanning to product 2D and 3D images. Other configurations of SS-OCT systems employing parallel acquisition systems are variations to these contemporary systems.

As previously noted—and in sharp contrast to contemporary, prior-art SS-OCT systems and structures—systems and structures according to the present disclosure employ one or more photonic integrated circuits (PICs) that are advantageously constructed using combinations of optically compatible material such as Silicon (Si), Indium Phosphide (InP), Gallium Arsenide (GaAs), Indium arsenide (InAs) quantum dots, Germanium (Ge), or other suitable, optically compatible material. Of further contrast, prior art OCT systems, such as those that do describe photonic integrated circuits, often times do not utilize swept-source techniques, but instead use a very different OCT technology namely, spectral domain optical coherence tomography. And for those prior art systems that do describe the use of PICs for SS-OCT they do not address the integration of many optical functions such as interferometers, dual polarization, dual balanced, FQ receivers with integrated photo-detectors and electro-optical integration which is key to making this systems robust, manufacturable, small, and low-cost. Finally, prior art OCT systems generally employ simple, miniature optical bench technology using small optical components placed on a substrate, and do not include a widely tunable optical source or integrated k-clocks and detectors.

Figure 2:
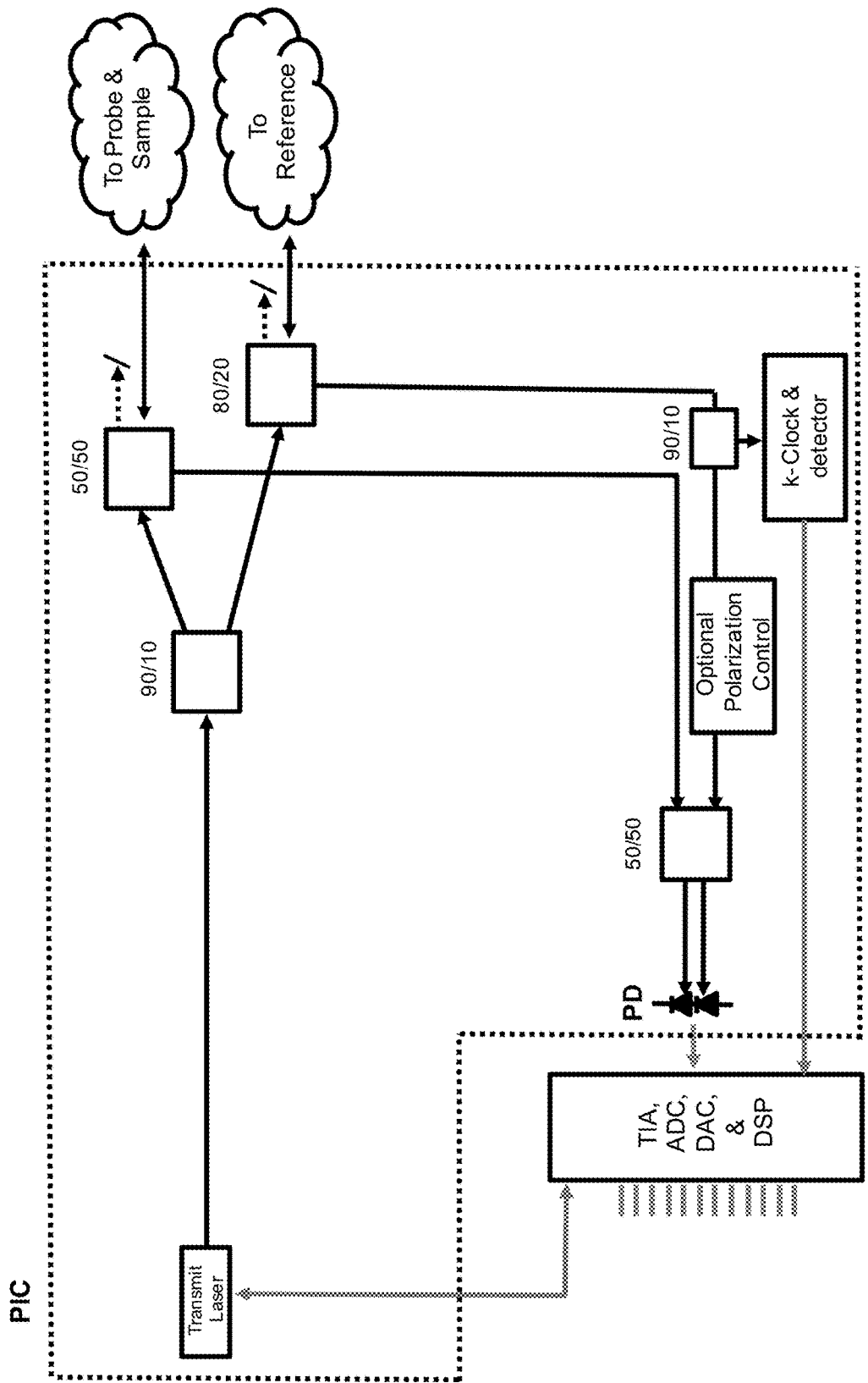
FIG. 2 shows a schematic block diagram of a system having a single dual-balanced receiver according to an aspect of the present disclosure.

With these principles in place, we may now examine more particular exemplary configurations and systems according to aspects of the present disclosure. Turning now to FIG. 2, there it shows a schematic block diagram of an illustrative system having a single, dual-balanced receiver according to an aspect of the present disclosure. As depicted therein, a dotted line outlines those components that may be advantageously incorporated (integrated) into/onto a single PIC as one exemplary configuration according to the present disclosure. Importantly, and as may be readily appreciated by those skilled in the art, a greater or lesser number of the components shown may be integrated into the PIC as system design dictates or further benefit(s) arise from such integration. For example in some illustrative embodiments the transmit laser can be located outside the PIC.

As shown in that FIG. 2, a tunable (transmit) laser is optically coupled to a 90/10 coupler. The 90% output of that coupler is directed to a 50/50 coupler, the output of which is directed to a probe module that couples light to/from a sample while—in a preferred embodiment—performing a lateral or a rotational scanning of light across the sample. Note that in this schematic FIG. 2, the lateral scanning is not specifically shown.

Returning to FIG. 2, the 10% output of the 90/10 coupler is directed to an 80/20 coupler that further couples light to and from a reference module. As may be readily appreciated, such a reference module may include an fixed or adjustable path length device that sets measurement range of interest and include other devices (e.g., polarization rotators, attenuators, lenses, mirrors, etc.) and perform other functions as well. Unused ports of the 50/50 sample path and the 80/20 reference path may be terminated or may alternatively be used to supply light to a k-clock input port.

As shown further in FIG. 2, light reflected back from the 80/20 coupler is shown coupled to a second 90/10 coupler. The 10% output of that second 90/10 coupler is shown coupled to an optional k-clock and detector—which will be discussed later—and the 90% output of that second 90/10 coupler is shown coupled to an optional polarization controller that may be automatically or manually adjusted. Notably, it may be advantageous to include another polarization controller and 90/10 coupler in the sample path to balance dispersion and birefringence.

As may be appreciated, the polarization controller so used may be an active controller that is controlled by the electronics module (connections not specifically shown) or alternatively, be manually set. Reference and sample light are coupled to a 50/50 receiver coupler and directed to a balanced photo-detector configuration to enhance receiver sensitivity and minimize laser intensity noise as well as other noise sources.

Output from the photo-detector is directed into an electrical processing module that may advantageously include one or more transimpedance amplifiers (TIAs), Analog-to-Digital Converter, (ADCs), Digital to Analog Converter(s), DACs, and Digital Signal Processing (DSP) electronic modules. Advantageously, such electronic modules may be included in one or more integrated electronic chips including Application Specific Integrated Circuits (ASICs) and/or Field Programmable Gate Arrays (FGPAs) as well as other discrete or monolithic electronic devices. This electrical processing in some embodiments can be housed in the same electro-mechanical package (co-packaged) or can be located in a separate electromechanical package.

As shown, the electrical module depicted in FIG. 2 also receives the k-clock output and is further connected to the transmit laser such that it may control its operational characteristics. Some exemplary embodiments do not require the use of a k-clock but it is advantageous if the frequency sweep is not linear or highly repeatable as discussed later. As may be appreciated and understood, sections of the PIC shown in FIG. 2 and external to the dotted line may be optical fibers or free-space optical links or a combination thereof.

It is worth noting at this point in the discussion that a wide variety of other coupling ratios and configurations other than those shown are contemplated and consistent with this disclosure. For example, an alternative embodiment may replace the 50/50 and 80/20 output couplers (connecting the sample and references) with circulators such that an increase in useful signal power and an increase in the isolation of reflected light with respect to the laser cavity is achieved. In configurations where bulk circulators are used, four external connections to the PIC instead of the two shown in FIG. 2 are employed.

Figure 3:
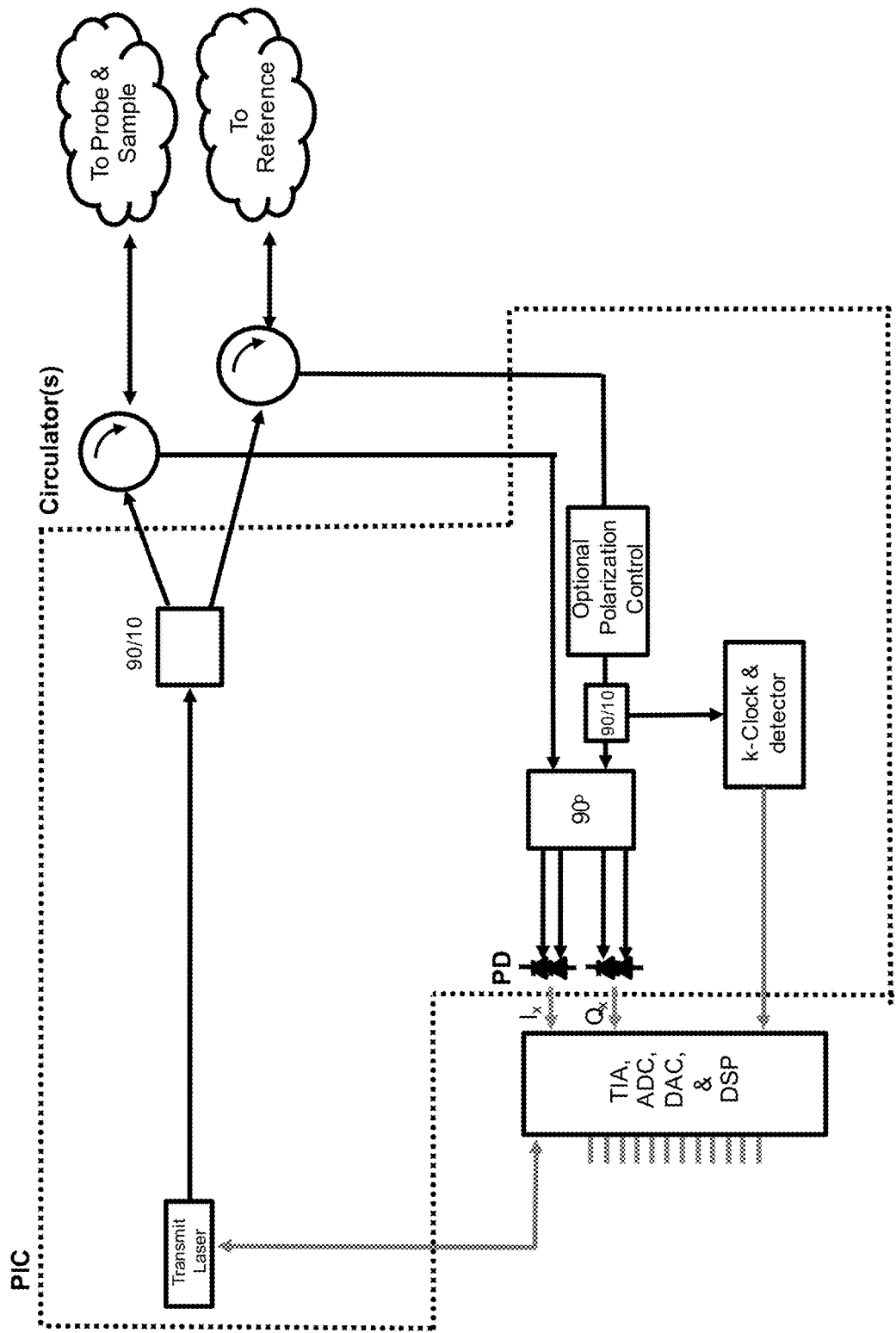
FIG. 3 shows a schematic block diagram of a system having circulators and a 90 degree hybrid exhibiting dual-balanced I and Q channels according to an aspect of the present disclosure.

Turning now to FIG. 3, there it shows a schematic block diagram of an illustrative system having circulators in place of the 50/50 and 80/20 splitters of FIG. 2, and a 90 degree hybrid exhibiting dual-balanced I and Q channels according to an aspect of the present disclosure. More specifically, and as shown in FIG. 3, received optical signals are routed to a 90 degree hybrid processor that includes four output signals that represent two dual-balanced in phase ($I_x$) and quadrature ($Q_x$) optical signals. The 90-degree hybrids may be—for example—multimode interference couplers, star couplers, or a network of 1×2 and 2×2 couplers.

The I ($I_x$) and Q ($Q_x$) signals depicted in FIG. 3 allow phase-sensitive detection of light from the sample and extraction of additional optical information on the sample and other signal processing improvements. Of further advantage, the photodetectors may be monolithically integrated into the PIC using a suitable optical detector material (e.g., Ge).

In one illustrative embodiment—and as may be readily appreciated by those skilled in the art—the photodetectors may be butt coupled or otherwise optically coupled to the PIC or located on a separate device. In the illustrative embodiment depicted in FIG. 3, the entire region shown within dotted lines is advantageously included in/on one single PIC. In other contemplated embodiments according to the present disclosure, the tunable laser may be external to the PIC. Alternatively, only the receiver portion may be included within the PIC, or the circulators may be replaced with couplers and located within the PIC as well. As may be appreciated, a great number of configurations are contemplated by the present disclosure.

Figure 4:
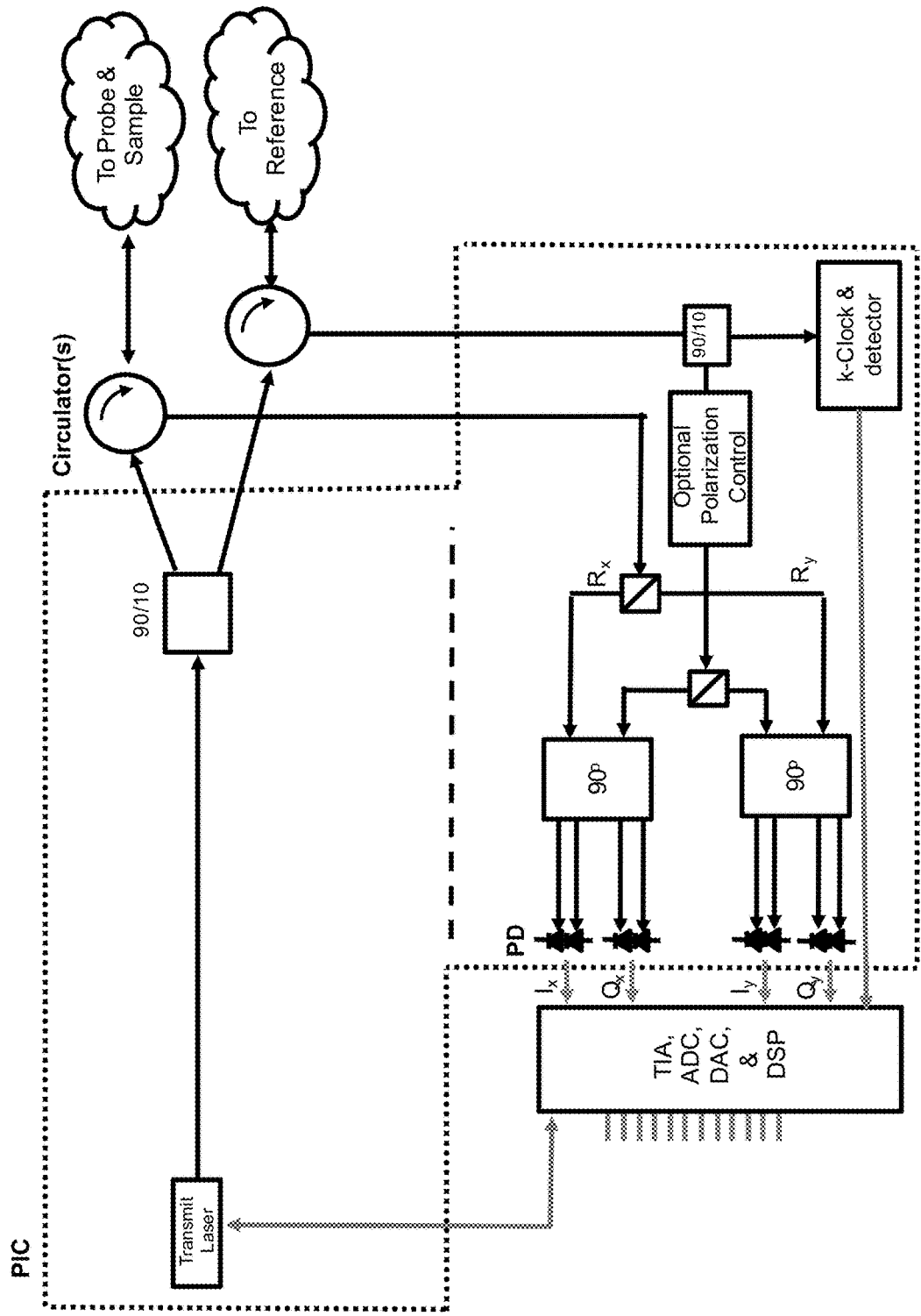
FIG. 4 shows a schematic block diagram of a system having circulators and dual polarization receiver with a polarization splitter and 90 degree hybrids exhibiting I and Q channels in two polarizations according to an aspect of the present disclosure.
Figure 5:
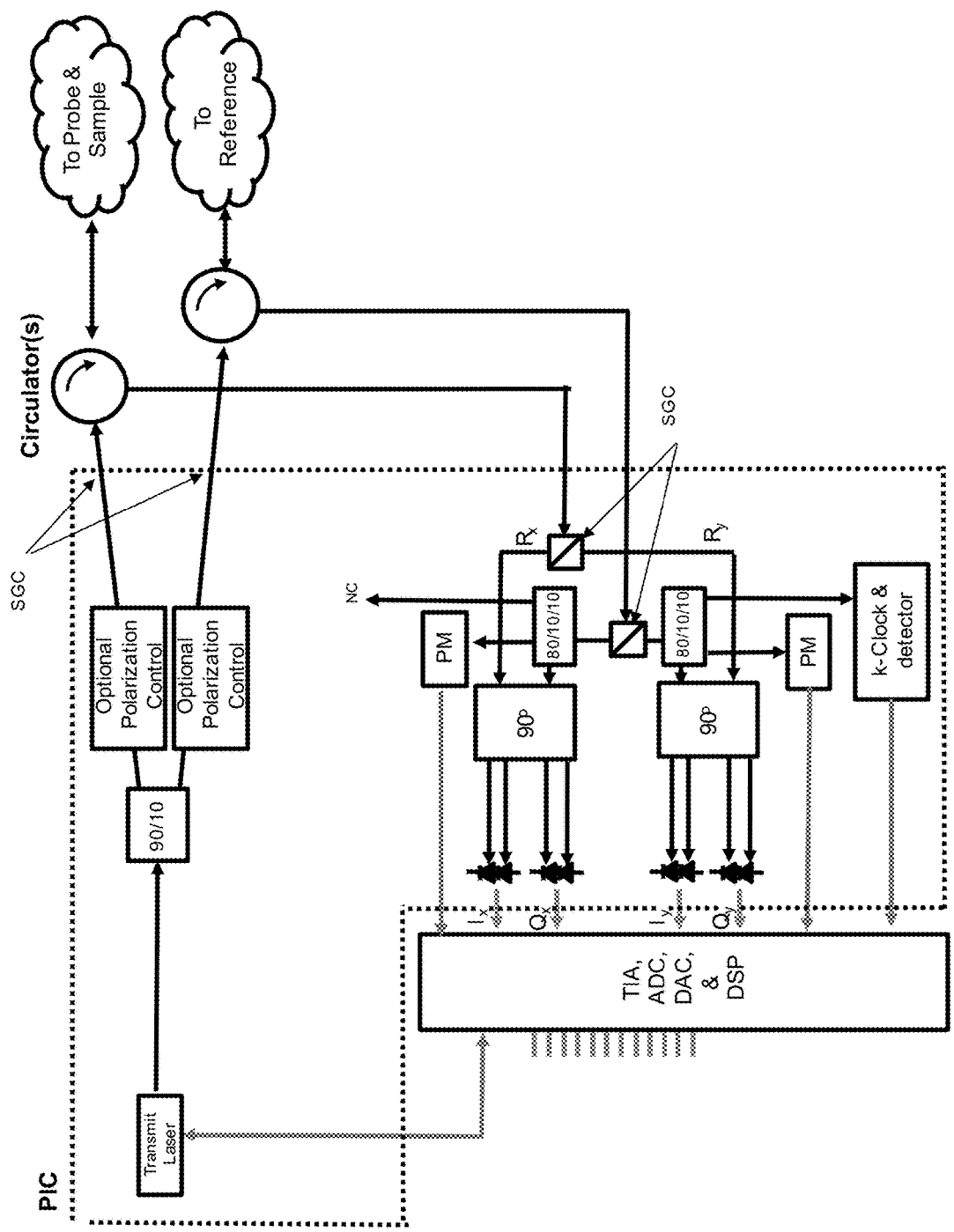
FIG. 5 shows a schematic block diagram of a system having circulators and dual polarization receiver with a polarization splitter and 90 degree hybrids exhibiting I and Q channels in two polarizations and surface grating couplers used to couple light on and off a photonic integrated circuit (PIC) according to an aspect of the present disclosure.
Figure 6:
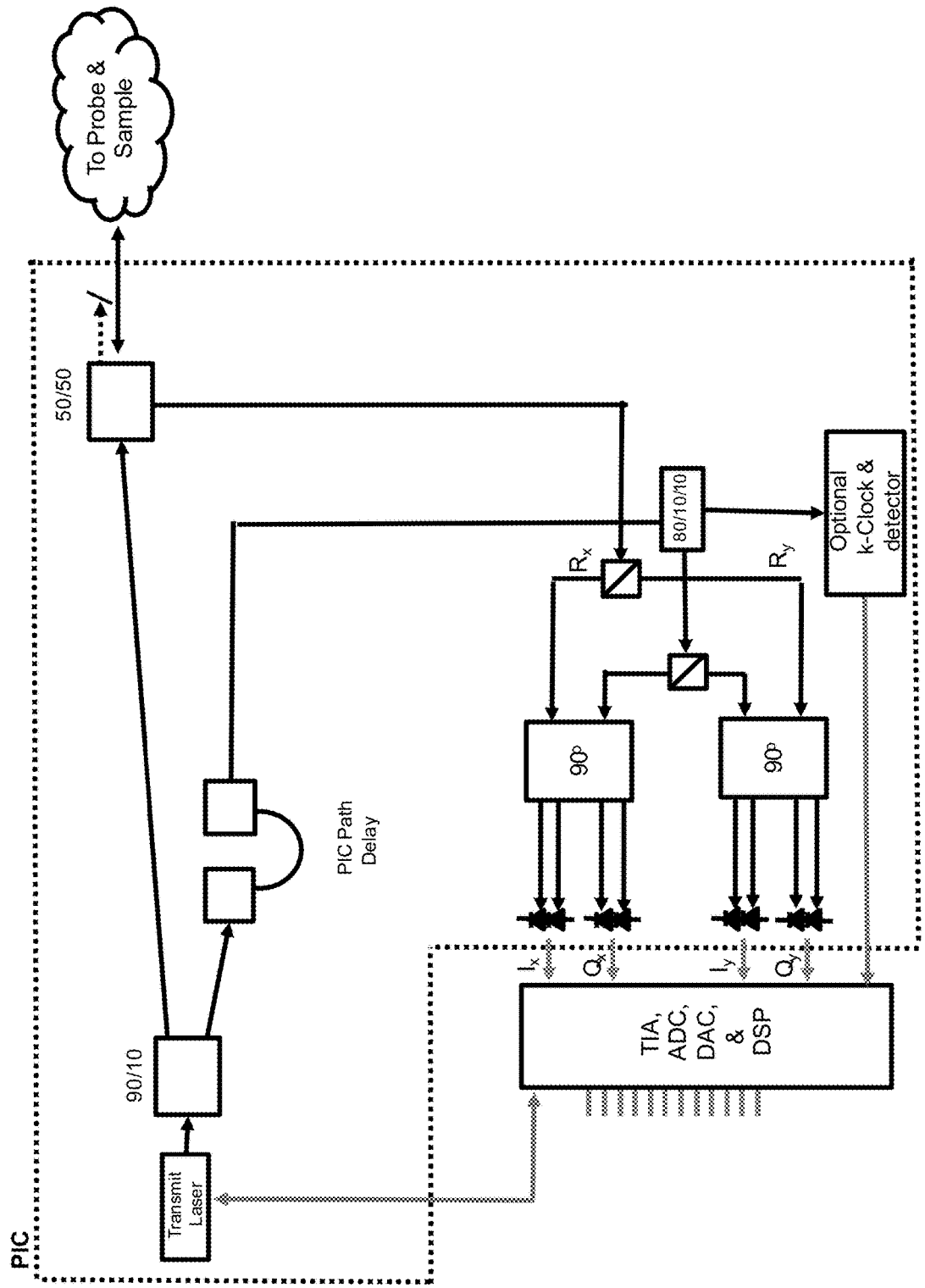
FIG. 6 shows a schematic block diagram of a system having a single PIC input/output port and a dual polarization receiver with a polarization splitter and 90 degree hybrids exhibiting I and Q channels in two polarizations where the system has a laser with long coherence length and a delay for the reference arm contained within the single PIC according to an aspect of the present disclosure.

FIG. 4, FIG. 5, and FIG. 6 show further illustrative extensions to these configurations shown and described. More particularly, they depict illustrative configurations wherein a received optical signal is routed to a polarization diversity receiver that includes two 90-degree hybrid processors. Such embodiments advantageously exhibit improved capabilities with respect to polarization-diversity and polarization-sensitivity along with an improved ability to measure both the sample birefringence and other characteristics along with phase sensitive detection within each polarization. Such phase and polarization sensitive detection permits functional imaging via Doppler, increased sensitivity and improvements in signal processing and sample imaging information possibilities such as polarization independent imaging or polarization sensitive imaging.

FIG. 4 shows a schematic block diagram of an illustrative system including circulators and a dual polarization receiver including polarization splitters and 90 degree hybrids exhibiting I and Q channels in two polarizations according to an aspect of the present disclosure. As may be appreciated, such a system may be integrated onto a single PIC including source(s), k-clock, polarization controller, and dual polarization receiver.

FIG. 5 shows a schematic block diagram of an illustrative system having circulators and dual polarization receiver with a polarization splitter and 90 degree hybrids exhibiting I and Q channels in two polarizations and surface grating couplers used to couple light on and off a photonic integrated circuit (PIC) according to an aspect of the present disclosure. As depicted therein, the polarization controller is integrated, however this device is optional and may be included external to the PIC in the reference arm—or not at all. Alternatively—in those environments in which the bandwidth is very large—it may be beneficial to have a polarization controller positioned in both the sample and reference paths such as that shown thereby balancing particular optical properties such as birefringence, dispersion, and/or other optical characteristics.

With continued reference to FIG. 5, it is noted that phase and polarization sensitive detection advantageously allows functional imaging via Doppler, increased sensitivity, and improvements in signal processing and sample imaging information capability such as polarization sensitive detection and imaging.

With continued reference to FIG. 5, it is noted that the illustrative embodiment shown therein is compatible with surface grating couplers (SGC). As may be appreciated, one dimensional (1D) surface grating couplers may be used to direct (couple) light off of the PIC and into circulator(s) while two dimensional (2D) surface grating couplers may be used to receive reflected light from the circulators and simultaneously split them into nearly orthogonal polarizations. As depicted in FIG. 5, power monitors (PM) are used to monitor polarization alignment and other conditions of the reference path. Advantageously, wide-band grating couplers can be made by using a core material with a lower index than silicon, such as silicon nitride, and/or by using a smaller spot size on the grating, for example from a small core fiber. Of further advantage, different combinations of couplers or combinations of 1D and 2D couplers may be used simultaneously in alternative embodiments.

With reference now to FIG. 6, there it shows an alternative embodiment according to an aspect of the present disclosure that particularly useful when used with a laser source having sufficiently long coherence length for the sample measurement distances. As depicted in FIG. 6, the entire reference path length may be located on the PIC. Consequently, only one PIC external connection is employed—the one to the sample. With a configuration such as that depicted in FIG. 6, an on-chip path delay unit constructed from a tightly wound spiral or other waveguide structure may be included. To impart low loss and low temperature dependence such a waveguide structure may be fabricated from Silicon Nitride (SiN) or Silicon Oxynitride (SiON) materials.

At this point we note that for improved axial/longitudinal resolution, it is important that each arm exhibit substantially matching total dispersion and birefringence characteristics. In certain configurations it is convenient to position/place similar devices in both arms so as to keep the optical characteristics balanced. For configurations in which such placement of similar structures is impossible or impractical, then one can—for example—introduce (additional) dispersion into the PIC structure by using—for example—ring resonators (as all-pass filters) coupled to waveguides. Advantageously as an alternative, if the path characteristics are not matched then it is also possible—if the coherence length of the laser is long and the optical properties are stable—to electronically post process this dispersion or birefringence imbalance out electronically in the DSP in cases where both I and Q phase sensitive detection is utilized.

Figure 7:
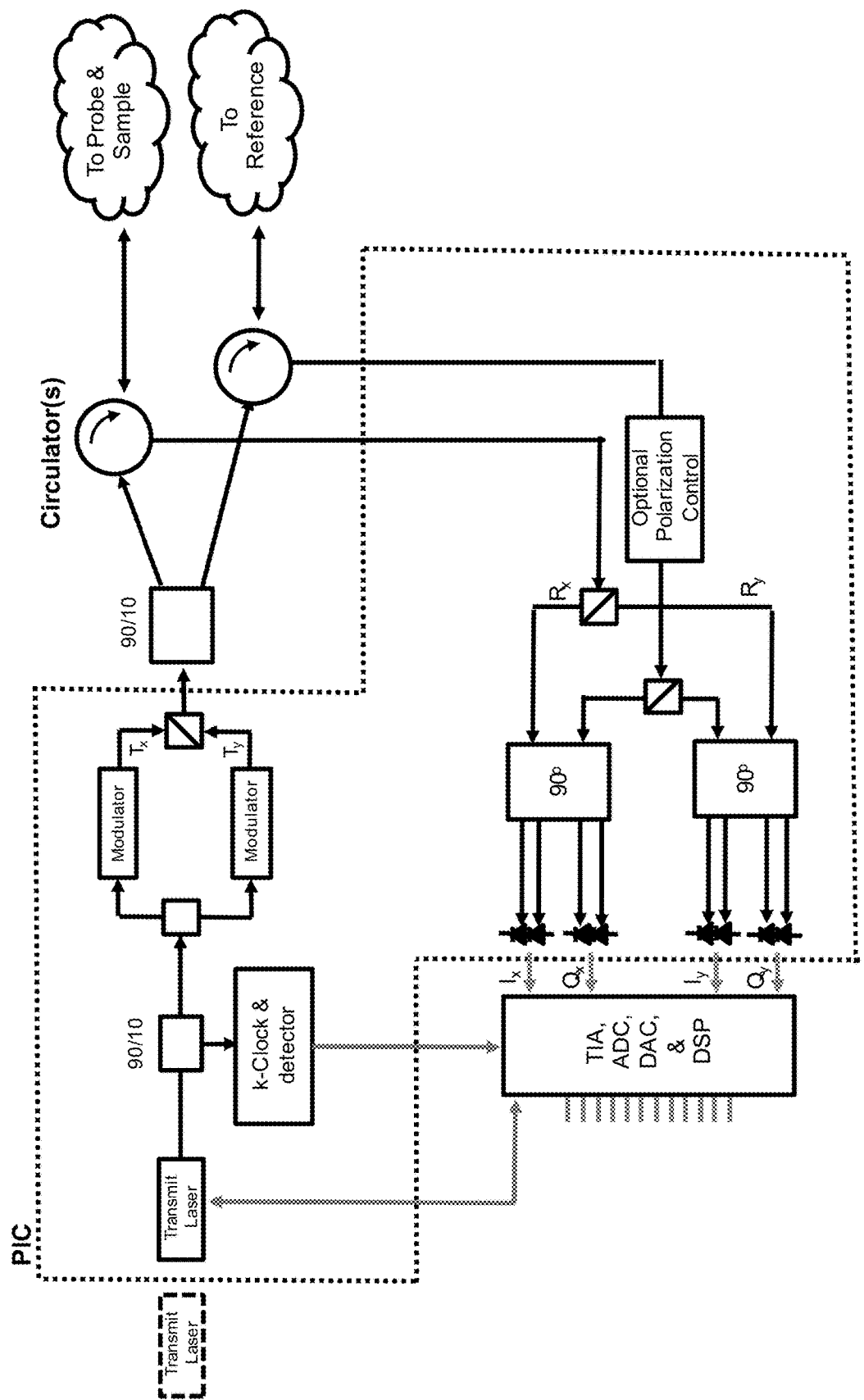
FIG. 7 shows a schematic block diagram of a system having couplers and dual polarization receiver including a polarization splitter and 90 degree hybrids exhibiting I and Q channels in two polarizations and a dual polarization modulator according to an aspect of the present disclosure.

Turning now to FIG. 7, there it shows an alternative illustrative embodiment according to the present disclosure in which a transmitter path (the output laser light before the probe/sample) includes a dual polarization modulator and only one output light path from the PIC (the sample and probe module are split external to the PIC). As may be appreciated, the modulator in this embodiment may provide alternating on/off or other modulation (e.g. within an axial scan or sending alternate polarizations on adjacent axial scans) into the sample such that birefringence information along the axial profile of the sample is extracted. That is to say the modulation may be performed rapidly—relative to a laser frequency sweep time—or may be performed more slowly, alternatively on each laser sweep or other combinations.

In addition to the functionality described above, the modulator may also be used to set arbitrary intensity and phase information on each polarization such that the receiver module can perform processing on this modulation to extract additional features. For example a Hamming or other window can be applied to the laser output amplitude. As discussed earlier it is possible to locate the tunable optical transmit laser (or an equivalently functioning tunable optical source (e.g. and ASE source and a tunable filter)) external to the PIC. The polarization combiner after the two modulators may be either a 2D grating coupler or a polarization rotator and polarization beam combiner connected to a facet coupler.

At this point we note that polarization splitters, combiners, and rotators shown in the various figures are preferably fabricated onto the PIC and exhibit a broad bandwidth, low loss and high extinction characteristics. As those skilled in the art will readily appreciate, there are known a variety of ways to build such individual structures and devices.

With respect to surface grating couplers, there exist a variety of designs of surface grating couplers—including 1D and 2D grating couplers as well as designs exhibiting various fiber incidence (i.e., normal, slight, extreme)—such that output light is primarily coupled into two output waveguides instead of four, for example. As may be appreciated, one advantage of surface grating couplers is they are easy to fabricate and easy to couple light into/out of them. Also surface grating couplers eliminate the need to rotate polarization on the PIC, because both polarization (states) signals in the fiber maintain the same polarization in the PIC. Conversely, one disadvantage of using surface grating couplers is that it is difficult to make them such that they exhibit both a very broad bandwidth a very low loss.

With respect to polarization controller(s) shown in various figures, they too can be implemented in a variety of ways and exhibit a number of particular characteristics. By way of non-limiting example(s), it is noted that a polarization controller needs to exhibit a broad bandwidth and low loss. Also, the polarization controller should not introduce significant dispersion or birefringence over the laser tuning band. If such dispersion or birefringence exists then a second matching polarizer can be added—for example—to the sample arm of the system.

Advantageously, "endless" polarization controllers or resettable polarization controllers may be fabricated within the PIC, using, for example, a cascade of Mach-Zehnder interferometers. Alternatively, such polarization controllers may be located outside or off of the PIC. While in some configurations a polarization controller is not needed, in other configurations where it is included it can be set manually, or be electronically adjustable and advantageously not requiring resets to achieve an arbitrary polarization state (endless polarization controller).

Turning now to FIGS. 8(a)-8(c), there it shows three examples of k-clock processing modules according to aspects of the present disclosure. And while three illustrative examples are depicted in FIGS. 8(a)-8(c), those skilled in the art will appreciate that additional configurations are possible and contemplated. Generally, with respect to k-clocks, it is noted that in some embodiments—such as when a frequency sweep is very linear in time and repeatable—a k-clock is not needed. In other embodiments, a k-clock allows one to compensate for non-ideal frequency sweep parameters in the tunable laser. For example if the tunable laser is swept in a sinusoidal (or other waveform) sweep over time, then a k-clock will allow an output clock to be triggered at substantially regular frequency increment intervals and such signals will trigger the ADC (or be used in alternative digital signal processing if fixed time ADC sampling is used) such that a proper Fourier transform takes place. As discussed previously, structures according to the present disclosure advantageously integrate k-clock(s) into/onto the PIC along with a number of other optical and electrical functions.

With initial reference to FIG. 8(a), there it shows a simple dual balanced embodiment where two 50/50 couplers and a differential path delay are used in combination with dual balanced photo detectors. Turning now to FIG. 8(b), there it shows a non-differential embodiment where there are two (I and Q) electrical optical and electrical outputs phase shifted by 90 degrees. Finally, FIG. 8(c) shows an illustrative embodiment where there are two (I and Q) electrical optical and electrical outputs and each one of them contains a differential detection to eliminate common-mode noise. As noted previously, while these three illustrative embodiments are shown, those skilled in the art will understand that other embodiments are contemplated according to the present disclosure.

As may be appreciated, it is sometimes beneficial for the optical path length—such as that shown previously in FIGS. 1-7—from the laser source to the sample and further to the photodetector(s) to have approximately the same total delay as the path from the laser source to the triggering of the ADCs via the k-clock processing module. One way to achieve this is to have an optical delay between the laser output and the k-clock input that matches both delay and dispersive properties of the two path lengths. If the delay is small enough (~1 cm) then it can be contained within the PIC. If the delay is much longer, then a fiber optical patch cord can be designed into the path between the 90/10 coupler and the k-clock input (not shown). Another alternative method to achieve the same total optical delay is to introduce an electronic delay buffer after the photo-detection. In particular configurations such as when the laser souse tuning characteristics permit, such an arrangement may be a preferred one. Finally with reference to FIG. 8(a)-8(c), it is noted that clock generator and electrical processing elements may advantageously comprise TIAs, filters to reduce out of band noise, zero-crossing detectors, AGC elements, digital logic (e.g. OR, XOR) phase shifters, and dummy clocks and other processing functions. In still another alternate embodiment, the k-clock may comprise a ring resonator filter instead of a Mach-Zehnder interferometer.

As may be appreciated, one critical component of an SS-OCT system—as well as other optical systems—is the laser source. More particularly, a desirable laser source exhibits the following characteristics namely, rapidly tunable, widely tunable, stable, long-coherence length, desirable optical signal to noise ratio (OSNR), minimal excess intensity noise, compact, reliable, and inexpensive. It is also advantageous for such a laser source to exhibit a near sawtooth waveform in terms of wavelength (or frequency) vs. time.

Figure 9A:
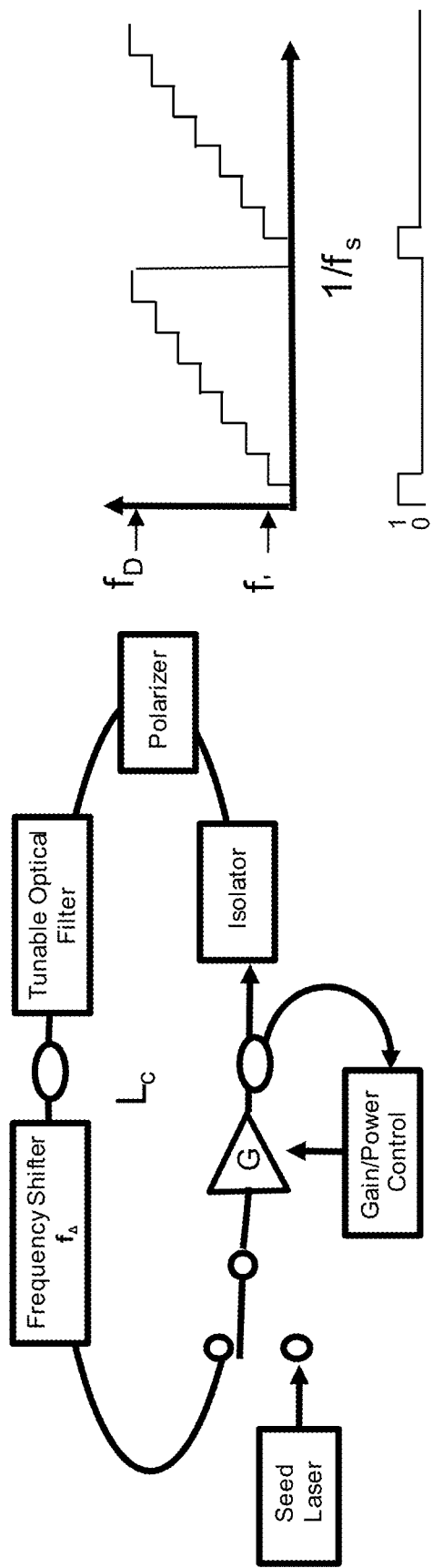
FIG. 9A shows a schematic block diagrams illustrating a frequency tunable optical source including a ring configuration and optical frequency shifter.

FIG. 9(a) shows one illustrative embodiment of a frequency tunable source according to an aspect of the present disclosure. As shown, the tunable source includes a seed laser, an optical switch, an amplifier, a frequency shifter, a tunable optical filter, an isolator and a polarizer—all configured in a common ring arrangement. Operationally, at the start of each laser sweep the optical switch is connected to the seed laser. This seed laser provides the necessary output power and coherence length sufficient to start the frequency sweep while preferably saturating the optical amplifier to minimize ASE noise. The seed laser can be integrated into the PIC or externally located and fiber coupled onto/into the PIC. The light from the seed laser is optically amplified and sent to the frequency shifter and is maintained long enough in the ring to stabilize the light and amplifier.

We note that there exist alternatives to the seed laser such as using a single frequency reflector in combination with the ring gain element to produce a laser starting frequency. Also in one embodiment the 2:1 switch and seed laser can be eliminated and the tunable optical filter is set to the starting frequency and the frequency shifter is turned off for a period sufficient for the ring laser to begin lasing on a ring cavity within the tunable optical filter bandwidth.

Notably, the illustrative embodiment depicted in FIG. 9(a) is arranged as a unidirectional ring. Those skilled in the art will appreciate that other arrangements using linear cavities or alternative configurations are contemplated by this disclosure as well. More specifically, the ring arrangement may be fabricated within a single integrated optical component or particular part(s) of the ring arrangement may be external to the PIC (e.g. in optical fiber or free space).

Continuing with our operational discussion of the frequency tunable source depicted in FIG. 9(a), at a particular time (preferably the round trip time), the switch is enabled and the light begins to circulate around the ring as depicted in the line chart. For each circulation around the ring, the light is shifted in frequency by $f_A$ and this shift continues until the desired total sweep range is completed $f_D$. The total sweep time is completed in $1/f_s$.

Figure 9B:
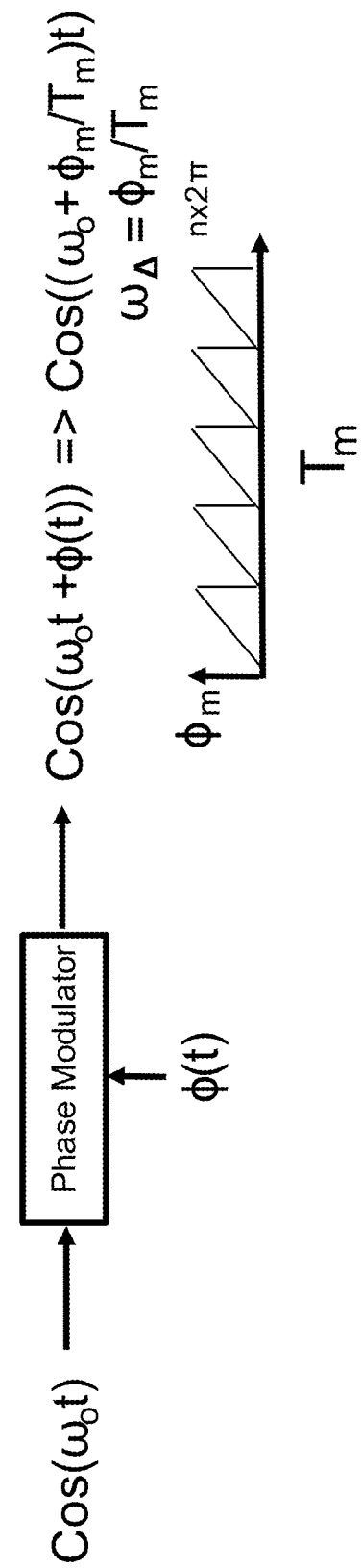
FIG. 9B shows a frequency shift including a phase modulator and serrodyne modulation.
Figure 9C:
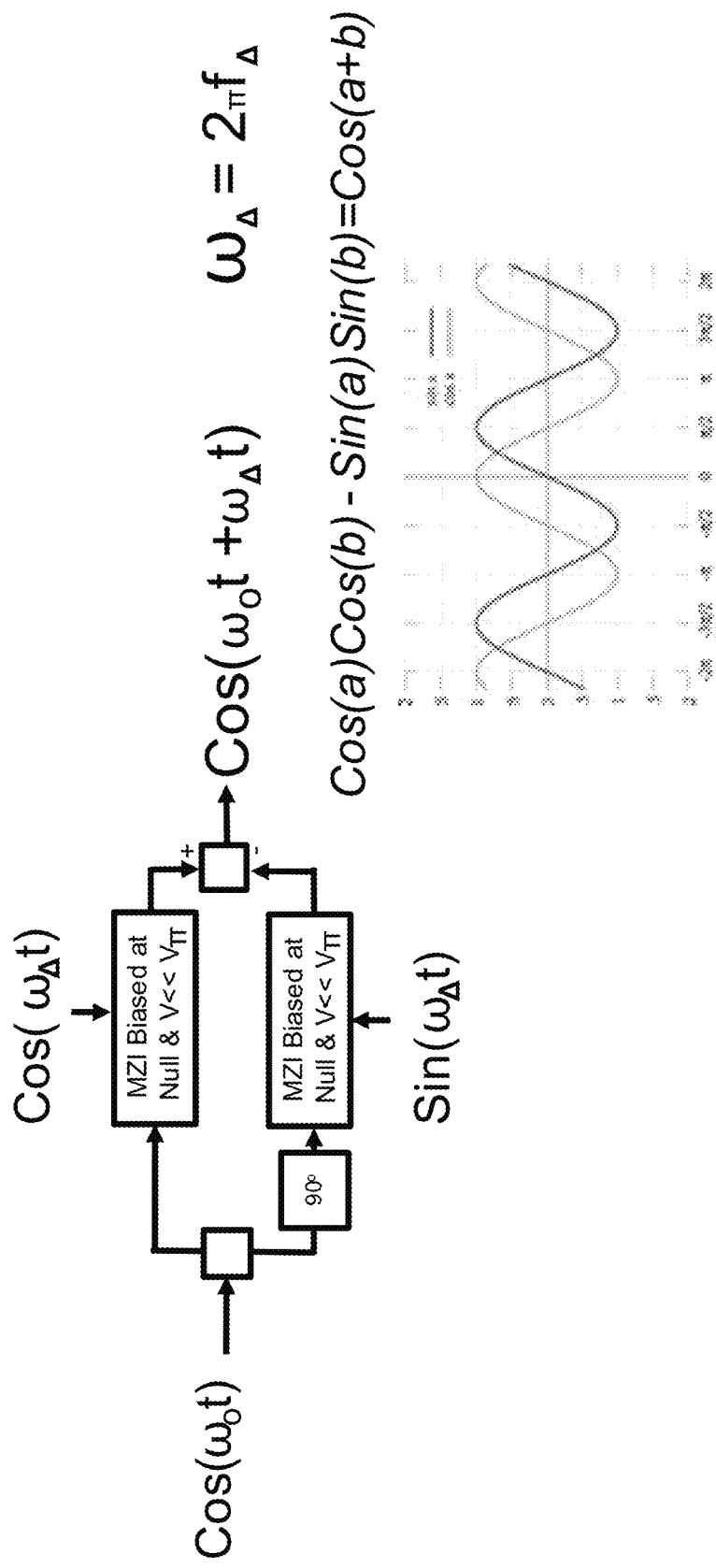
FIG. 9C shows a frequency shifter having two Mach Zehnder modulators.

As may be readily appreciated, there are several ways to generate a constant frequency shift. With reference to FIG. 9(b), there it shows an illustrative example using a simple phase modulator that is reset at integer multiples of $2\pi$. FIG. 9(c) shows another illustrative example to generate a constant frequency shift which employs two Mach-Zehnder modulators biased at their null point and driven in their linear range. The two modulators are similar but one input includes a 90 degree optical phase shifter. If the Mach-Zehnder modulators are operated in their linear regime, then the drive signals are sinusoids. If the Mach-Zehnders are driven to their full extent of +/−pi, then the drive signals are triangle waves.

Note that it is important to maintain stable operation of the frequency shifter and in particular to extinguish any unshifted, spurious harmonics of the input light. To maintain such conditions, automatic bias control circuits for biasing each modulator at its null position and adjusting the RF drive amplitude and phase can be implemented similar to those used for optical telecommunication systems such as DP-QPSK and other systems that use Mach-Zehnder modulators.

As noted previously, when the frequency tunable source is configured as a ring such as that shown, the ring may optionally include a polarizer to extinguish unwanted light as normally the ring runs in a single polarization. The optical gain may be provided by rare-earth (e.g. Yb/Er) doped waveguides; from monolithically integrated optical gain elements like InP, GaAs, Germanium, or III-V quantum dot material such as InAs; or using a wafer bonded or butt coupled optical gain elements such as InP or GaAs, or other semiconductor material either integrated with the PIC or external to a PIC that can be optically or electrically pumped. Similarly, frequency shifters may be fabricated in any of a number of optical compatible materials. Notably, if they are fabricated in Si, they may be either carrier injection or carrier depletion type modulators—or even both if they are modulators having an oxide in the junction.

Note that ring structure depicted in FIG. 9(a) includes an optical isolator and a tunable optical filter. In an alternate embodiment(s) the isolator and/or tunable optical filter is/are not needed. This is particularly appropriate in those situations wherein the frequency shifter produces minimal carrier leak through and spurious harmonics and the number of circulations of the ring over a scan period is sufficiently small such that only modest amplified spontaneous emission (ASE) and harmonic noise builds up in the ring.

With further reference to FIG. 9(a), it is noted that a tunable optical filter is employed. This tunable optical filter is not always needed but for certain configurations, such as a large number of light circulations, it can be beneficial. Advantageously, it may be fabricated using a narrow filter with fine tracking or relatively coarse bandwidth filter with corresponding coarse tracking. One advantage of the tunable filter is that it can suppress any residual ASE noise and spurious signals (such as unshifted light leaking through the frequency shifter) from building up in the laser cavity.

With this additional suppression of the tunable optical filter, the number of cycles of the loop can be increased and the cavity length decreased to the point where the entire laser is housed in a PIC. Additionally, a polarizer can be employed to eliminate unwanted ASE and light scattered into the orthogonal polarization (as indicated in FIG. 9(a)). Notwithstanding, it is possible to use a gain element that supports one polarization and thus there is no need for an additional polarizer. Furthermore, an optical isolator may be incorporated to ensure unidirectional operation if needed. This isolator can be off the PIC or can be contained on the PIC. Also as mentioned above and shown in FIG. 9(a), an alternative to the use of the optical switch is to use a fiber optic coupler and two on/off switches. Such an approach can be easier to control and implement at the expense of increased throughput loss.

Shown further in FIG. 9(a) is a circuit for controlling the optical gain or output power of the optical amplifier (OA). For example, in constant-power mode, a small optical tap at the output of the OA is used to estimate the output power and this signal is fed back to internal parts of the OA (e.g. pump or VOA) to keep the output power constant. Other methods for power and gain control are known and contemplated as well.

Finally with reference to FIG. 9(a), note that a constant frequency shift is illustrated in this figure. Notwithstanding, it is possible to adjust the frequency shift over time to account for slight variations in propagation delay around the loop with wavelength if desired.

Figure 10:
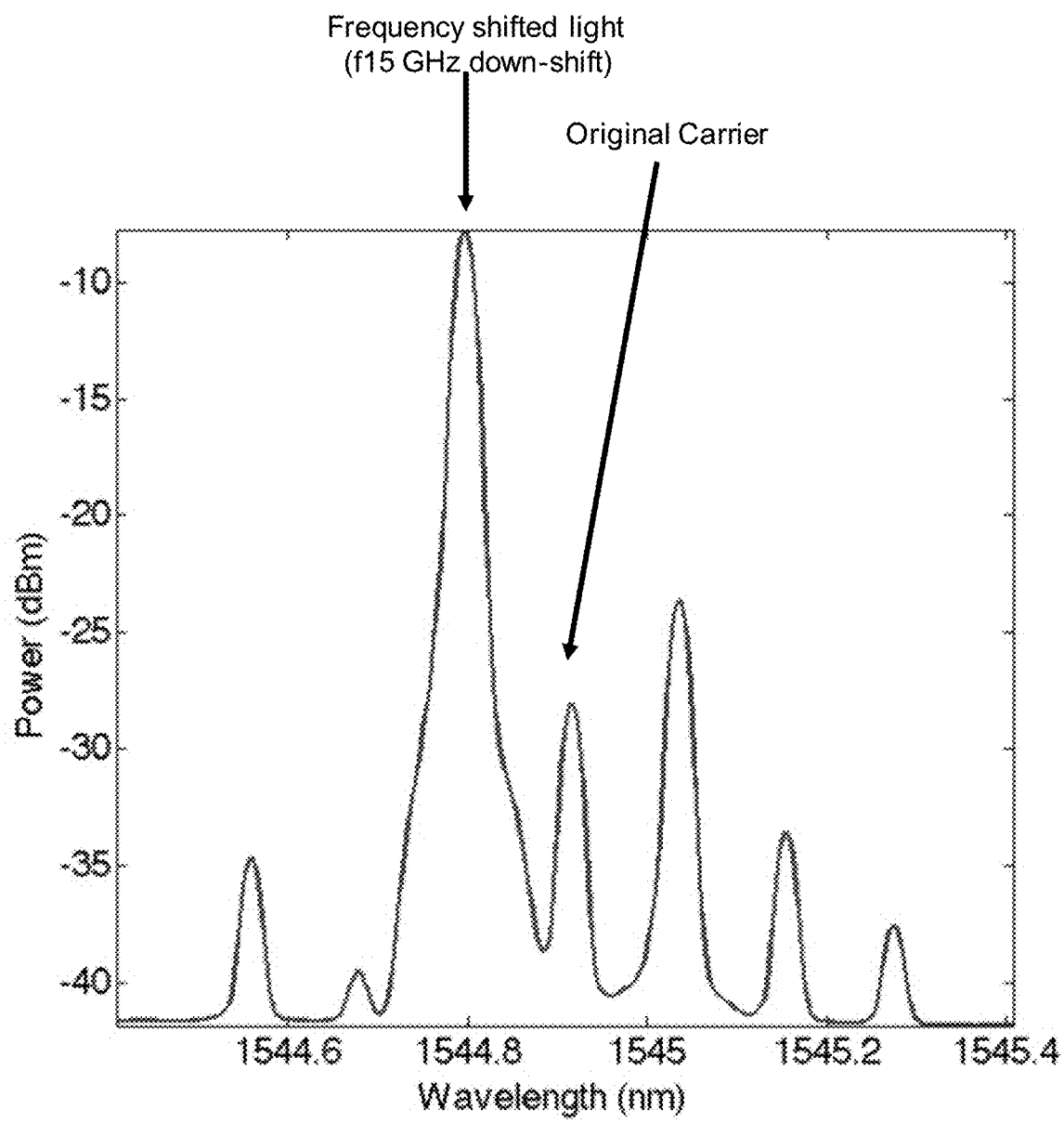
FIG. 10 shows an exemplary output of the frequency shifter of FIG. 9C constructed in a PIC according to an aspect of the present disclosure.

FIG. 10 shows a graph of our measured example of the frequency shifter shown in FIG. 9(c) in operation using a Si photonic I-Q modulator. This frequency shifter was created in a silicon photonic integrated circuit. The line shown in the center of the graph is some of the carrier leak through. The frequency shift is −15 GHz and the side mode suppression ratio (SMSR) is 15 dB. As may be appreciated, the performance of this frequency shifter may be improved with better electrical tuning however the figure clearly shows the functionality of the device.

Figure 11B:
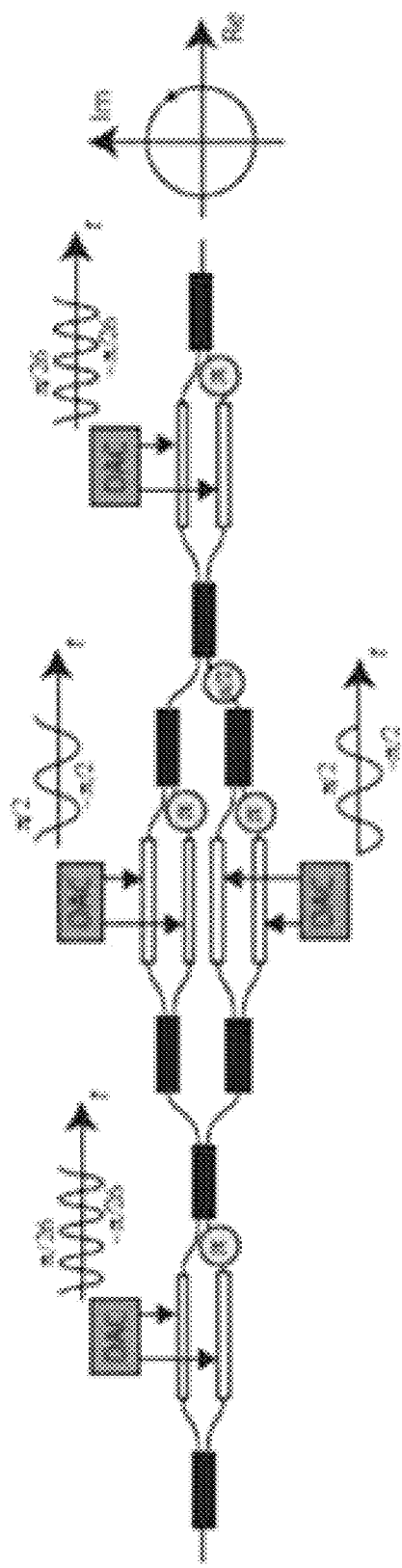
FIG. 11B show a schematic block diagrams illustrating a methods for achieving a frequency shift as compared with that shown in FIG. 9C and according to an aspect of the present disclosure.

With reference now to FIGS. 11(a) and 11(b), there it shows two additional embodiments of frequency shifter topologies for homodyne frequency tracking in telecommunication systems. With reference to FIG. 11(a), the embodiment shown is a single side band (SSB) modulator. It comprises an I-Q modulator driven by two triangular waves having peak-to-peak amplitude of π and a 90° relative phase shift. Operationally, the output rotates endlessly around the origin of the complex plane with a linear change in phase with time.

As is known, SSB modulation is traditionally performed at a fixed frequency. One advantage of the embodiment of FIG. 11(a) is the modulator is driven from a digital-to-analog converter (DAC) with a look-up table, and the driving frequency constantly varies as the table is read out at a speed proportional to the required phase shift rate. Notably, SSB modulators are traditionally made in LiNbO3 and designed to run at high speeds. In this application however, we wish to operate the SSB modulators at low speeds (<1 GHz) and in a silicon PIC. Advantageously, this allows us to use current injection rather than carrier depletion modulation, resulting in low optical loss and low drive voltages. Finally, an SSB modulator such as that depicted in FIG. 11(a), exhibits a 6-dB excess loss.

FIG. 11(b) on the other hand, shows a schematic SSB modulator design exhibiting only 3-dB excess loss. This design has the additional advantage of requiring only sinusoidal drive signals rather than triangular wave signals, which may be easier to generate. The design of FIG. 11(b) exhibits lower loss because rather than using just 3-dB couplers on the input and output it uses Mach-Zehnder switches that redirect the distribution of light between the I and Q modulators as the phase progresses around its circle. These are driven with twice the frequency as the I and Q modulators but only ~1/13 of the amplitude.

Figure 12:
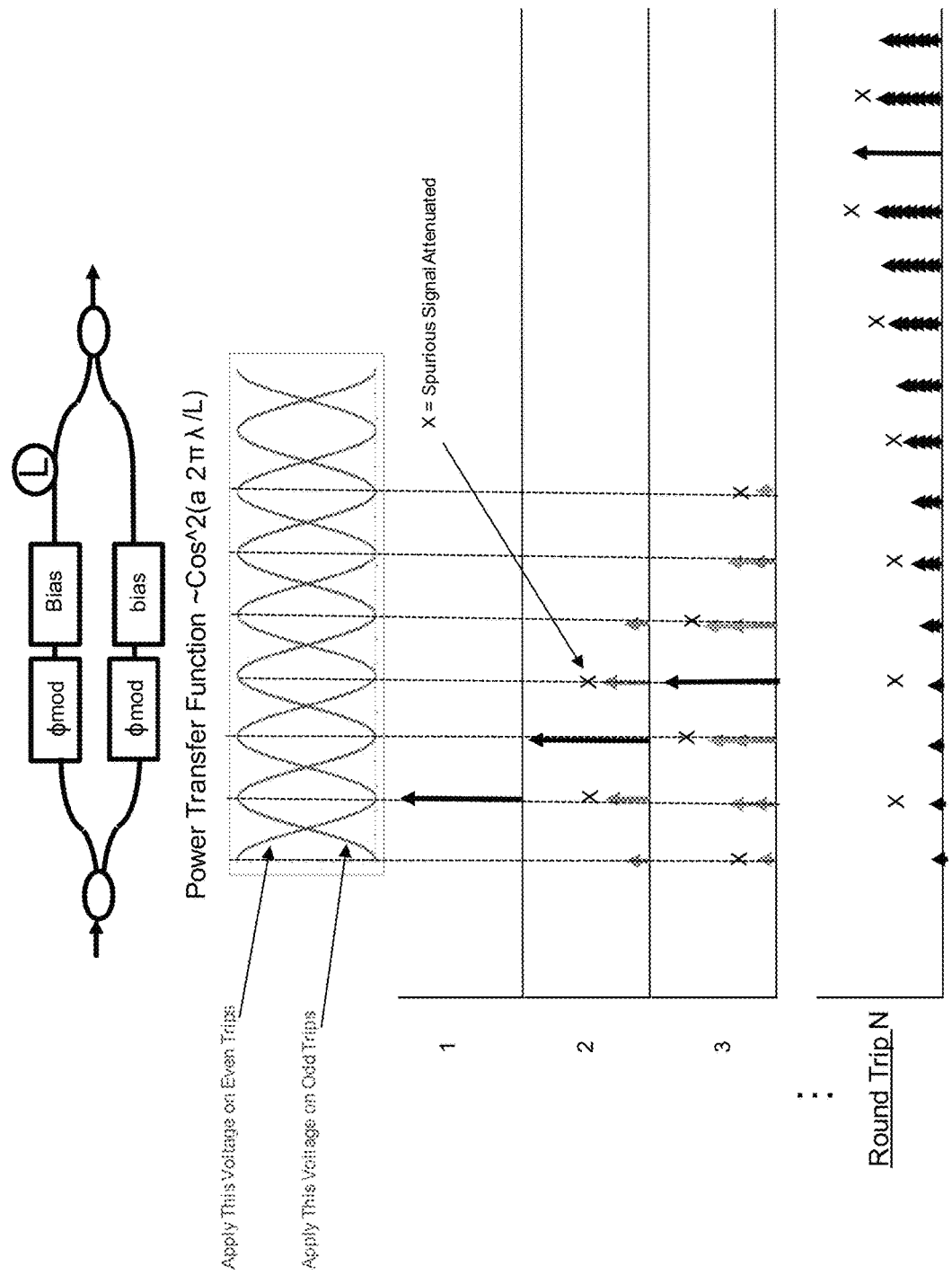
FIG. 12 shows a schematic block diagram illustrating an exemplary Mach-Zehnder modulator employed as a filter in a tunable laser according to an aspect of the present disclosure.

FIG. 12 shows one of many possible examples of a tunable filter that can be driven in a sinusoidal or preferably a digital fashion to minimize degradation in the output laser quality due to build up of ASE and/or spurious harmonics in the laser loop. (Note that in this disclosure we may refer to this loop as a laser loop even though in some embodiments there is not laser action and the cavity operates more like a long transmission line). The basic concept is that of a Mach-Zehnder modulator with unequal path lengths. The path length difference is chosen to be such that the transfer function has a transmission null at one $f_\Delta$ above and below the desired frequency shifted carrier and at all the subsequent periodic nature of the transfer function. These are qualitatively illustrated by the "X's" on FIG. 12. On the even trips one (blue) transfer function is applied. On the odd cavity trips the other (red) transfer function is applied. It is important that the modulator be driven rapidly so as to avoid collapsing the signal amplitude due to repeatedly passing through the modulator (similar to "eye closure" in digital communication signals). This modulator can have automatic bias circuitry that control the bias point (at null) and controls the relative amplitude and phase of the RF square wave or sine wave drive signal. Note the filter of FIG. 12 works well when driven in a wide bandwidth square wave fashion. And while it is also possible to drive the modulator with a sine wave which need not have a broad bandwidth, this can result in more distortion of the ideally constant amplitude signal but has the advantage of easier RF drive requirements.

To address the fact that the periodic power transfer function of the Mach-Zehnder filter may not ideally follow the constant frequency increment of the laser over a 100 nm or more sweep it is possible to utilize a more intelligent waveform than a simple sine or square wave to account for keeping the carrier at the center of one of the periodic peaks of the Mach-Zehnder transfer function at all times. Advantageously, it is also possible to alter the frequency of the frequency shifter.

Advantageously, it is possible to use more than one stage of Mach-Zehnder filtering. There are a variety of modulator delay configurations that can be used and the basic concept is to place nulls of each stage to eliminate spurious leak though of the carrier and unwanted harmonics. In many applications it suffices to have one stage. In other applications where a large number of cavity sweeps is desired two or more stages can be used. In order to drive the Mach-Zehnder modulator properly one approach is to provide a high-speed multi-channel DACs closely coupled to the Mach-Zehnder modulators. To keep the Mach-Zehnder path lengths short and within a single PIC it is beneficial to include a high frequency shift in the ring (e.g. 10 GHz).

Note that gain sections for tunable optical sources according to the present disclosure may comprise semiconductor optical amplifiers (SOAs), doped waveguide amplifiers, wafer bonded gain elements on silicon wafers, InP regrowth, germanium doped silicon lasers, or doped fiber amplifiers. It is also possible to configure multiple gain sections in parallel using WDM or other splitting/combining techniques to broaden the bandwidth. That is to say one could use multiple SOAs (or other gain mediums) in parallel connected in phase and with equal path lengths but different gain spectrum peaks.

Figure 13:
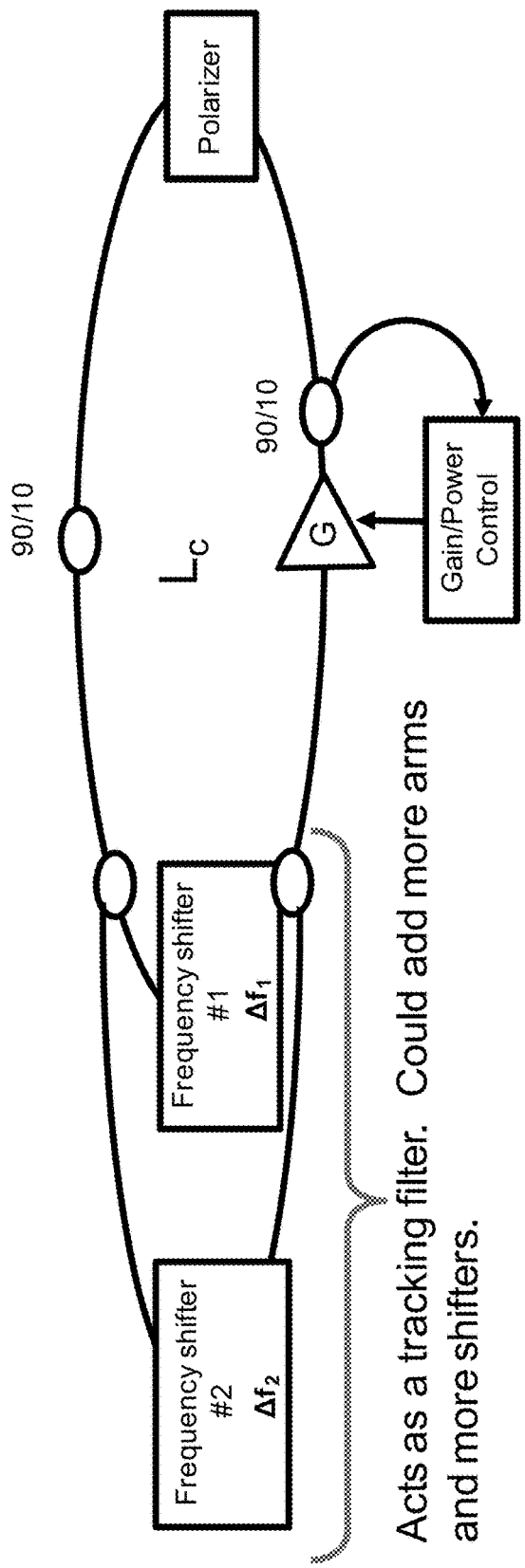
FIG. 13 shows a schematic block diagram illustrating a ring laser configuration employing two frequency shifters according to an aspect of the present disclosure.

In another alternative tunable laser embodiment according to the present disclosure are one(s) in which there are two or more frequency shifters in the laser cavity as, for example, shown in FIG. 13. Such an embodiment operates analogous to a Vernier laser cavity in which the light is split between two resonant cavities with different free-spectral ranges. Only certain cavity modes line up in both cavities simultaneously acting like an intracavity filter.

In one embodiment of this the rate of change of the frequency shifter is less than the cavity round trip time. In this structure is a laser undergoing laser oscillation and so the frequency sweep could be as slow or fast (the sweeping in one preferred embodiment is slow compared to the round-trip time) and there is much less concern about degradation in the buildup of amplified spontaneous emission (ASE) noise and subsequent reduction in optical signal to noise ratio (OSNR) of this approach due to its laser cavity characteristics than other approaches. The sweep in this embodiment could be continuous or it could be stepped. DACs (not specifically shown) can be used to directly drive the frequency shifters.

One interesting aspect of this embodiment is that these I-Q modulator types of frequency shifters are fundamentally different than acousto-optic frequency shifters in that the laser light adiabatically jumps back cavity modes as the laser is swept in frequency. Advantageously, seed lasers, tunable optical filters, isolators and other elements can be added to this cavity to improve operation at the expense of complexity. FIG. 13 shows two frequency shifters in parallel however, more or less could be used. More frequency shifters configured in parallel can produce a better rejection of unwanted cavity modes and the expense of increased complexity and wafer yield issues.

Figure 14:
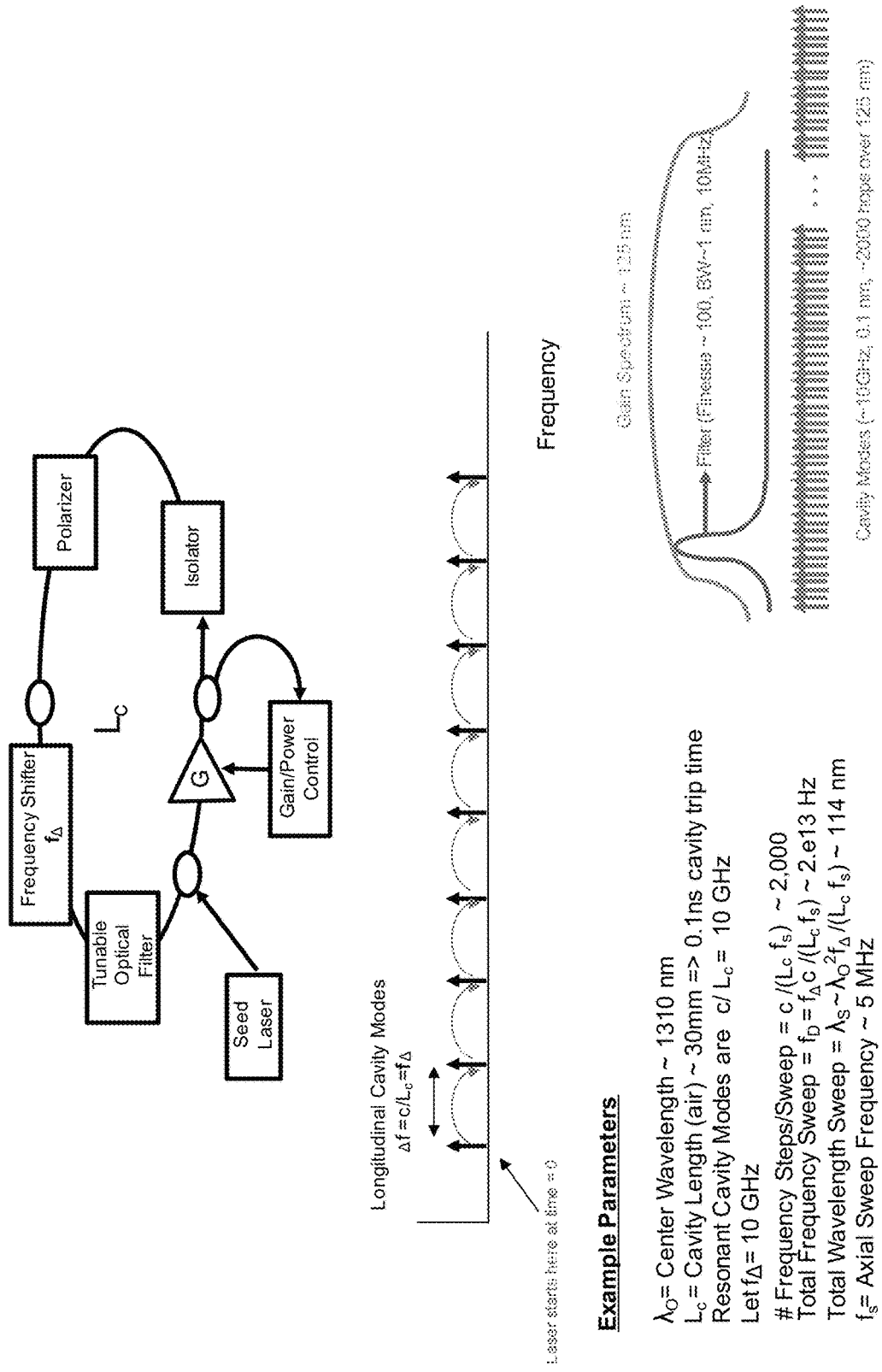
FIG. 14 shows a schematic block diagram illustrating a ring laser configuration having a frequency shifter and an optional tracking filter wherein the frequency shifter is configured to shift light entering into it to a new frequency that is closely aligned with a ring cavity mode according to an aspect of the present disclosure.

FIG. 14 shows yet another embodiment of a tunable optical source according to an aspect of the present disclosure. More particularly, FIG. 14 shows a schematic block diagrams illustrating a ring laser configuration having a frequency shifter and an optional tracking filter wherein the frequency shifter is configured to shift light entering into it to a new frequency that is closely aligned with a ring cavity mode. In this embodiment the frequency shifter is driven at a rate approximately equal to the round trip frequency (1/(round-trip-time)) or a multiple of the round trip frequency. In this fashion the light remains more coherent as it propagates around the cavity, and thereby suppresses ASE noise buildup and at each circulation the frequency is incremented and this results in a step wise sawtooth frequency sweep. An optional isolator can be included in the cavity but in a number of embodiments it is not needed.

The laser depicted in FIG. 14 may benefit from a tunable tracking filter to extend the tuning range and to keep unwanted cavity modes from building up in power. In other embodiments—particularly where smaller optical frequency sweep is needed—no tracking filter is needed.

Shown as an illustrative example, in the lower right hand corner of FIG. 14 there is the optical amplifier gain spectrum, the ring cavity modes, and the tracking filter. In one embodiment the tracking filter has a finesse of ~100, a bandwidth of ~1 nm, and a tuning speed of 10 MHz. There are a variety of other embodiments that are possible. Note that it may be highly beneficial that the tracking filter be synchronous with the cavity mode hoping from mode to mode.

As is known, chromatic dispersion and non-linear tuning of the filter can cause it to become slightly misaligned. It is possible to adjust the frequency shifter drive frequency and/or the tuning rate of the filter so they remain properly aligned. The seed laser can be connected by an on/off switch and a coupler, a 2:1 optical switch, or the seed laser itself can be turned on or off directly. Such a laser can be aligned to one of the lower cavity modes and have the proper power and coherent length characteristics suitable for the imaging application. The laser can be directly turn on/off at the start of the sweep or the laser can be left on to achieve stable operation and a separate on/off modulator can be use.

As noted above, to account for slight changes in the round-trip-time as the laser is scanned in frequency the frequency shifter frequency can be slightly adjusted in time to ensure that the shift of the light remains at or near a cavity resonance mode.

If the frequency shifter depicted in FIG. 14 is constructed using the approach described previously with respect to the configuration of FIG. 9(c), then it is possible to alter the function of the device "on the fly". That is, the device of FIG. 9(c)—with the addition of the normal electrically adjustable phase trims (not specifically shown)—can advantageously implement a variety of intensity and phase modulation waveforms.

For example it is possible to slowly or rapidly change the modulation format from "pass through mode" (e.g. no intensity or phase modulation) to frequency shifting mode. One advantage of this type of operation is it is possible to let the laser light circulate more than one round-trip-time within the laser cavity. This has the further advantage of allowing the sweep rate to be decreased (for more SNR during data collection) and allows the laser light to increase its coherence and settle for a longer time into the proper laser cavity mode. One additional benefit of this approach is that the laser sweep rate can be reconfigured on the fly to integer multiples of the fundamental sweep rate.

A basic idea behind this operation is that the laser operates at a cavity mode for one or more round-trip times. Then it is desired to move to a new cavity mode. Instead of just tuning a filter and restarting the laser at the new cavity mode and waiting for light in the laser cavity to build up from ASE and other noise sources, the new laser cavity mode is seeded with a strong light signal from the previous cavity mode. This has the benefit of improving both the coherence of the light and the rate at which the laser cavity can be tuned.

Note that with configurations such as those depicted in FIG. 14 there are various types of tracking filter that can be used including a single or multiple set of coupled ring resonators, Mach-Zehnder, Fabry Perot, and grating filters. As noted, it is possible to use no tracking filter at all specially for relatively short sweep ranges.

Figure 15A:
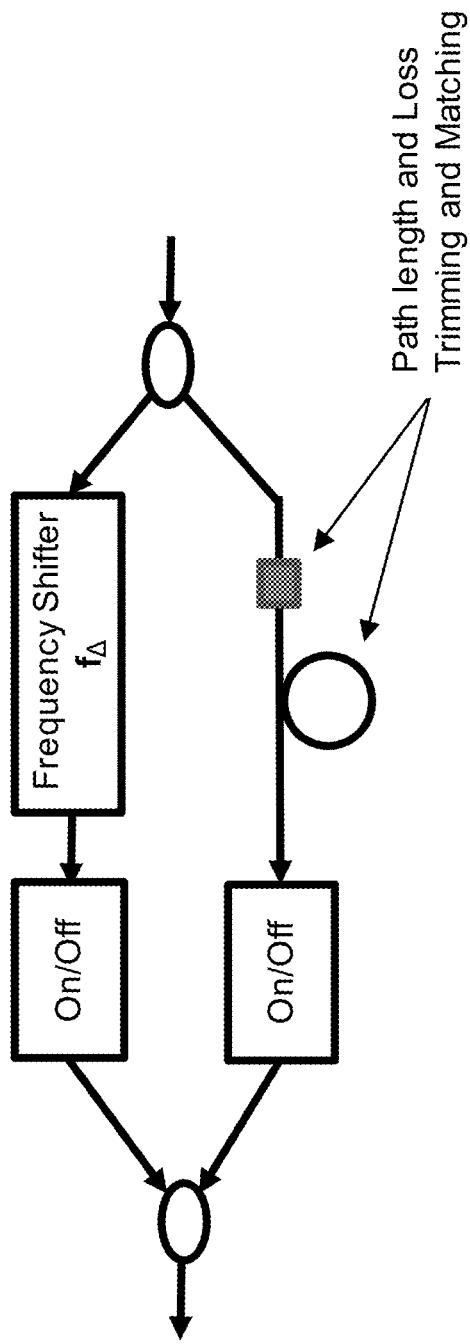
FIG. 15A shows a schematic block diagram illustrating an embodiment of a frequency shifter wherein a reconfigurable light modulator is employed.
Figure 15B:
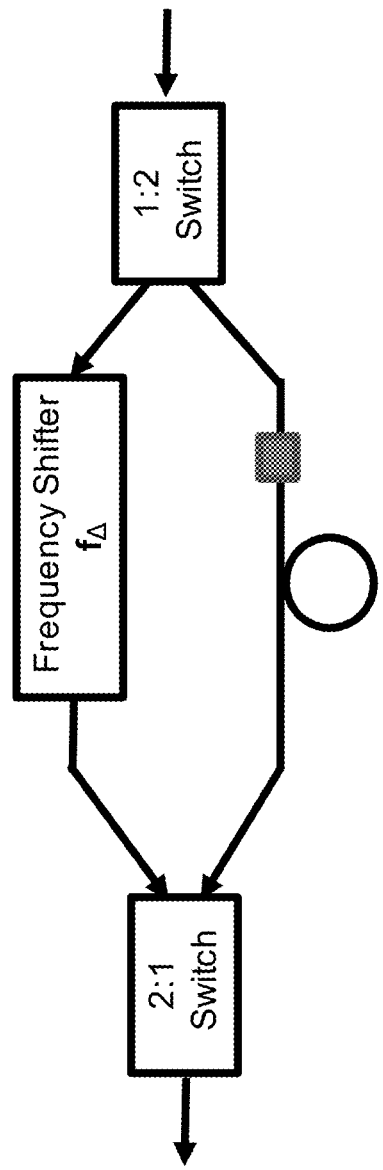
FIG. 15B shows a schematic block diagram illustrating an embodiment of a frequency shifter exhibiting either frequency shift or pass-through according to an aspect of the present disclosure.

With reference now to FIGS. 15(a) and 15(b), there they show alternate embodiments of a reconfigurable laser modulator that exhibits a state of either frequency shift or pass-through. The top path in each FIGS. 15(a) and 15(b) includes a frequency shifter. The bottom path includes a path length and loss trimming and matching fiber and other electro-optical characteristics that can be matched to the upper path. FIG. 15(a) shows an example configuration wherein on/off modulators are used along with passive couplers. FIG. 15(b) shows an example wherein 1:2 and 2:1 optical switches are used. Such switches can be Mach Zehnder or other types of integrated optical switches.

At this point it is notable that it may be beneficial to use silicon photonics for much of the PIC fabrication and couple another type of electrically or optical pumped optical gain medium that is configured to work in a double pass geometry through a gain medium. A double pass gain geometry can be beneficial in embodiments where the majority of the PIC is a single silicon photonic integrated circuit and that PIC is butt coupled (or otherwise coupled) to an InP or other material optical gain medium. It is possible to use a beam splitter and a double pass amplifier (where one facet of the amplifier is HR coated) instead of a unidirectional amplifier. Another approach is to use a combination of half wave plate and quarter wave plates and a polarization beam splitter to allow for more efficient operation. However such polarization isolation approaches require the gain medium be able to support both polarizations.

Figure 16:
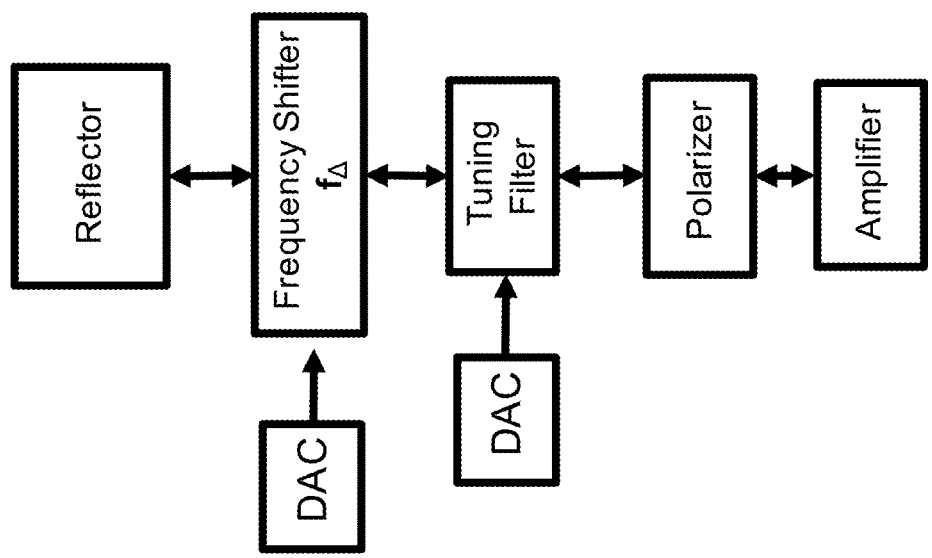
FIG. 16 shows a schematic block diagram illustrating alternate laser embodiments that employ a linear cavity configuration in close electrical communication with one or more DACs to achieve high speed according to an aspect of the present disclosure.

FIG. 16 shows an example of an embodiment of a tunable laser wherein the frequency shifter operates in a linear cavity (not a ring configuration) and a gain medium operates in a double pass geometry. High speed DACs can be directly coupled with the tuning elements to ensure rapid, high-speed agile tuning.

Figures 17A, 17B, 17C:
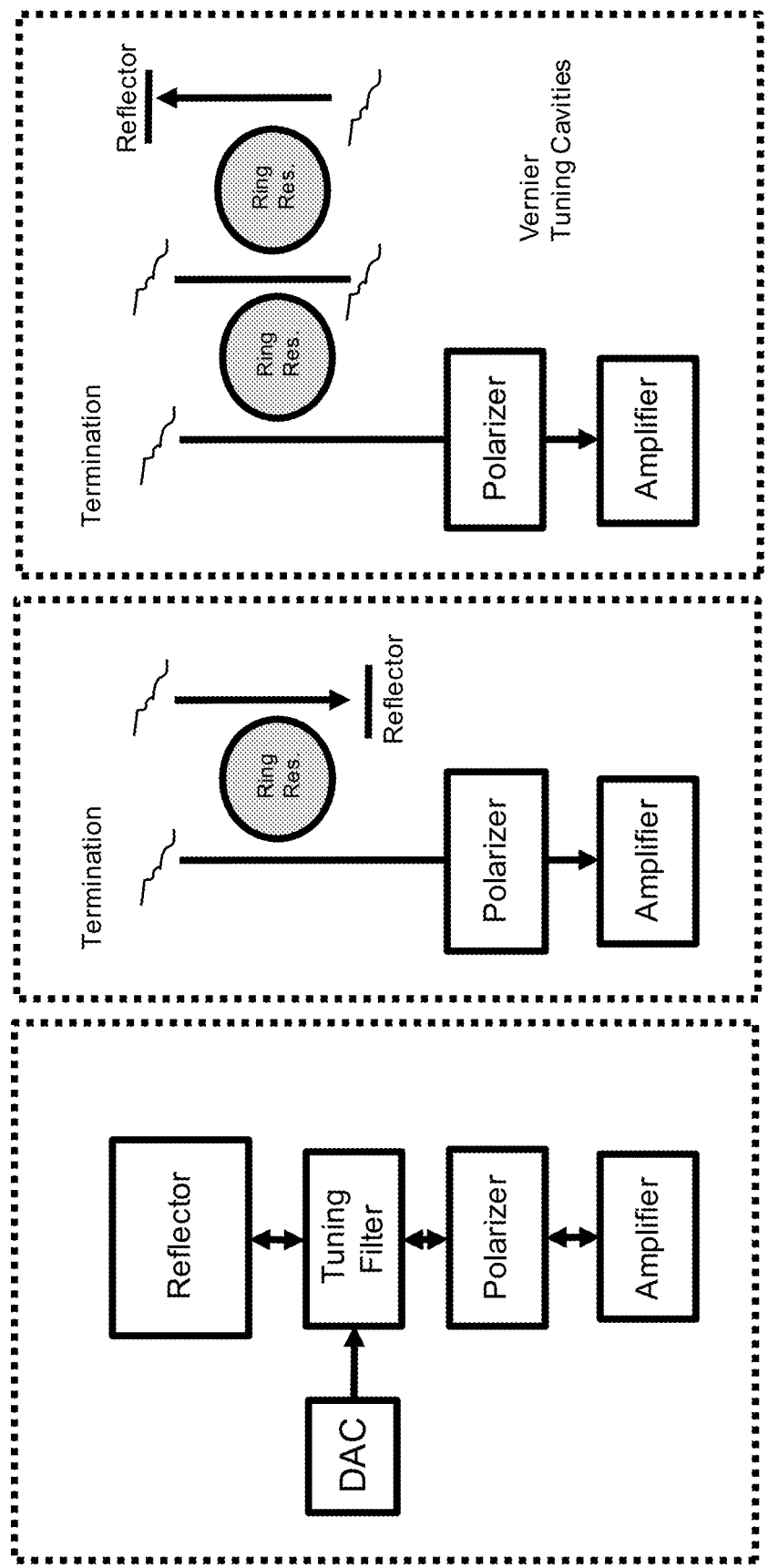
FIG. 17A shows a schematic block diagram illustrating a laser embodiment that does not include a frequency shifter in a cavity.
FIG. 17B shows a schematic block diagram illustrating a laser embodiment that does not include a frequency shifter in a cavity including a one ring resonator configuration.
FIG. 17C shows a schematic block diagram illustrating a laser embodiment that does not include a frequency shifter in a cavity including a two ring resonator configuration.

With reference now to FIG. 17(a), there it shows linear cavity examples of tunable lasers that do not employ a frequency shifter modulator. When there is no frequency shifter, in one exemplary embodiment the laser mode hops as it tunes. In other alternative exemplary embodiments cavity length adjustments may be made along with other approaches to minimize mode-hopes. It yet another exemplary embodiment the laser operates in several laser modes at once (e.g. multi-mode) and the groups of different modes are active as the nominal laser frequency is tuned.

FIG. 17(b) shows an exemplary embodiment employing one ring resonator and FIG. 17(c) shows another exemplary embodiment where two ring resonators are employed. In a preferred embodiment of the embodiment of FIG. 17(c), the ring resonators have different free spectral ranges and the two rings operate in a vernier tuning mode to extend the tuning range of the laser beyond that possible with just one ring resonator.

FIGS. 18(a)-18(b) shows an example of a complete photonic integrated circuit similar to some of the systems shown in previously. The receiver portion is a dual polarization FQ dual balanced configuration similar to those shown in FIGS. 4, 5, and 6. This particular illustrative embodiment uses a silicon photonic PIC with a recessed region that contains an InP two-channel optical gain element. One side of the InP gain element contains HR coatings and the other side (which interfaces with the SiPh PIC) contains angled facets to minimize any unwanted reflections. As described earlier an alternative to this butt coupled InP gain element approach shown in FIGS. 18, other types of but coupled gain elements other than InP can be used and furthermore it is possible to monolithically integrated the gain on the PIC substrate (and not use butt coupling) by using known approaches such as growth of III-V quantum dots (e.g. InAs), Germanium, or InP or by using wafer bonding approaches and evanescent or other optical coupling of the light from the silicon photonic circuit into the bonded optical gain element. The optical gain elements can be optically or electrically pumped.

In this embodiment there are two separate gain elements in the InP chip that contain gain peaks at different wavelengths. In this manner it is possible to have an optical frequency sweep that is broader than one gain element can provide. In another embodiment (not shown) one element is used instead of two for simplicity. In other embodiments there could be more than two gain elements for even broader frequency sweeping. At the output of the upper gain element there is a phase shifter. This phase shifter can be thermal or electro-optically tuned.

One purpose of this phase shifter is to match the nominal optical path lengths such that in spectral areas where the laser light has significant components from both gain elements the light from each gain element constructively combines in the coupler. One purpose of the Mach Zehnder combiner (M/Z Combiner) is to optimize coupling of light to the upper gain element or the lower gain element. For example when the laser is operating at a wavelength aligned with the peak of the lower gain element this M/Z would have a null at the upper gain element gain peak. At a laser wavelength aligned with the peak of the upper gain element the M/Z would have a null in transmission at the lower gain peak. This M/Z could also contain adjustable phase shifter elements (not shown) to allow for active alignment. There are other combinations of M/Z filtering functions and gain peak arrangements that are possible.

Operationally, the laser depicted in FIGS. 18(a)-18(b) operates in a manner similar to that shown in FIG. 13 in that two frequency shifters are utilized and driven at different rates but the laser is in a Michelson interferometer embodiment instead of a ring cavity laser configuration. There are two frequency shifters and the outputs of the frequency shifters are connected to loop mirrors and thus the frequency shifters operate in a double pass configuration. Note that this laser embodiment could be replaced with the other laser embodiments as described elsewhere in this document. This includes a single frequency shifter approach, a single frequency shifter with a tunable tracking filter, and a tunable laser with no frequency shifter at all. One could employ more or less frequency shifters than shown in FIGS. 18(a)-18(b).

Note that while FIGS. 18(a)-18(b) do not explicitly illustrate a seed laser, those skilled in the art will recognize that an integrated or external seed laser with appropriate interconnect may be incorporated into the structure(s) shown therein according to aspects of the present disclosure. Alternatively, and as discussed previously, there are ways to eliminate the need for a seed laser by incorporating wavelength selective optical elements.

The PIC output couplers and PIC input couplers are surface grating couplers and may be similar to those shown previously in FIG. 5 except that in FIG. 18(a), only one PIC output surface grating coupler (SGC) port is used and the reference and sample probe light splitting is done external to the PIC. FIG. 18(b) shows an alternate embodiment for the Probe out and the Ref out that has a 90/10 splitter and two 1D output grating couplers on the PIC.

The reference input coupler is a 1D surface grating coupler and leads to two multi-mode interference (MMI) couplers to provide for X and Y polarization. The probe input coincides of a 2D surface grating coupler with normal fiber incidence. Each of the two common polarization arms are couple via a phase shifter and nearly 50/50 coupler into a common optical path and then coupled to the MMI couplers. The output of each MIMI coupler consists of two differential outputs that form a dual-balanced I/Q receiver. The unused ports of the near 50/50 couplers can be used for power monitoring. An alternative to using a 2D normal incidence surface grating coupler is to use a 2D non-normal incidence coupler.

Figure 19:
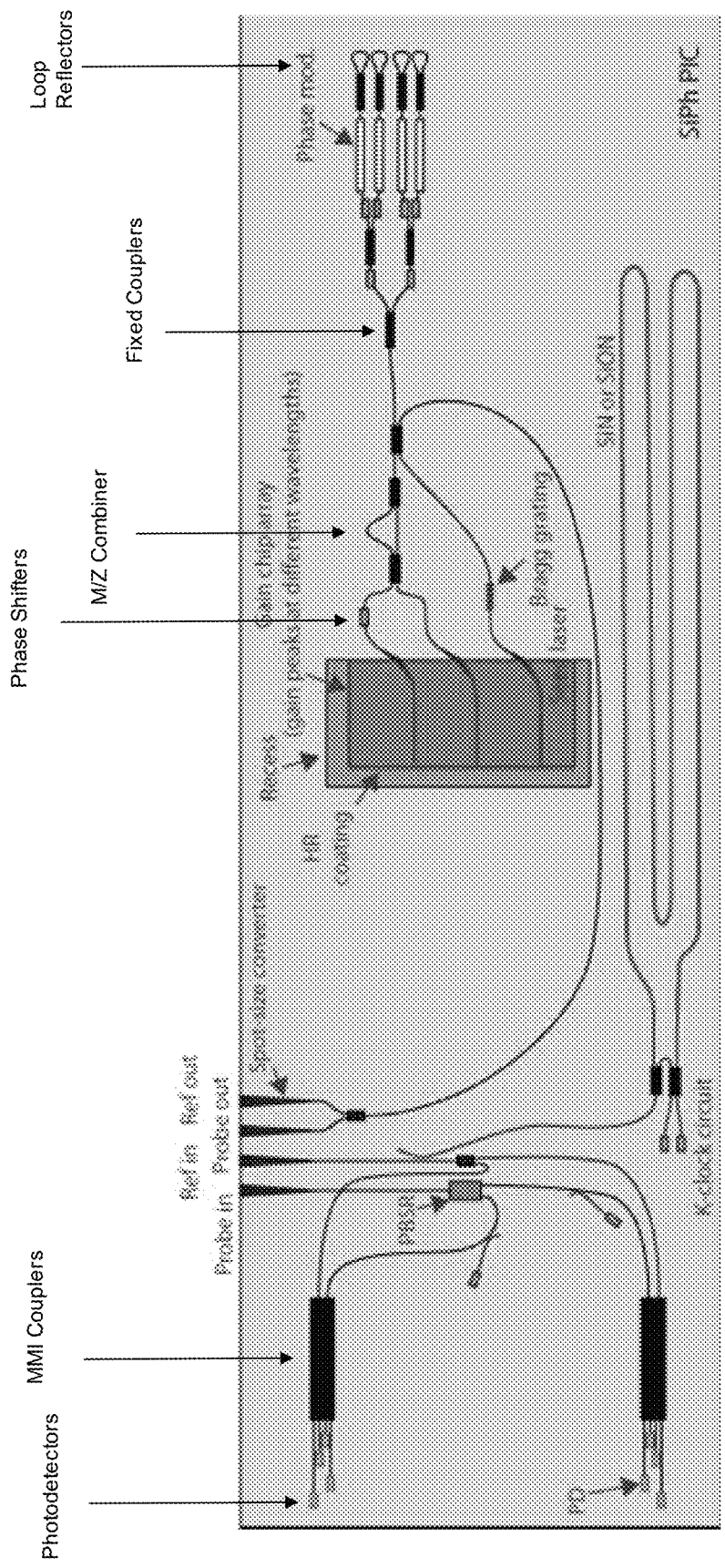
FIG. 19 shows a schematic block diagram illustrating a silicon PIC with an embedded gain chip and end face coupling and a frequency shifter according to an aspect of the present disclosure.

With reference now to FIG. 19, there it shows another illustrative embodiment according to the present disclosure that uses facet couplers instead of the surface grating couplers shown in FIG. 18(a). One benefit of facet couplers is they can achieve both low loss and very broad coupling bandwidth at the expense of fabrication and alignment complexity and the requirement for a planar polarization splitter and rotator. To achieve polarization rotation and splitting then the facet couplers are followed by integrated polarization beam splitters and integrated polarization rotators (PBSR) in the probe arm input channel. To achieve a long delay with low loss in the long arm of the k-clock (e.g. 2-20 mm) SiN, SiON, or other waveguide structures can be used. Also shown in FIG. 19 is a seed laser that contains a fixed (or tunable) Bragg grating reflector. This seed laser and be turned on and off by applying electrical current to the gain medium. The seed laser can be used to start the initial conditions of the frequency sweep in the laser cavity. The seed laser is optional.

Figure 20:
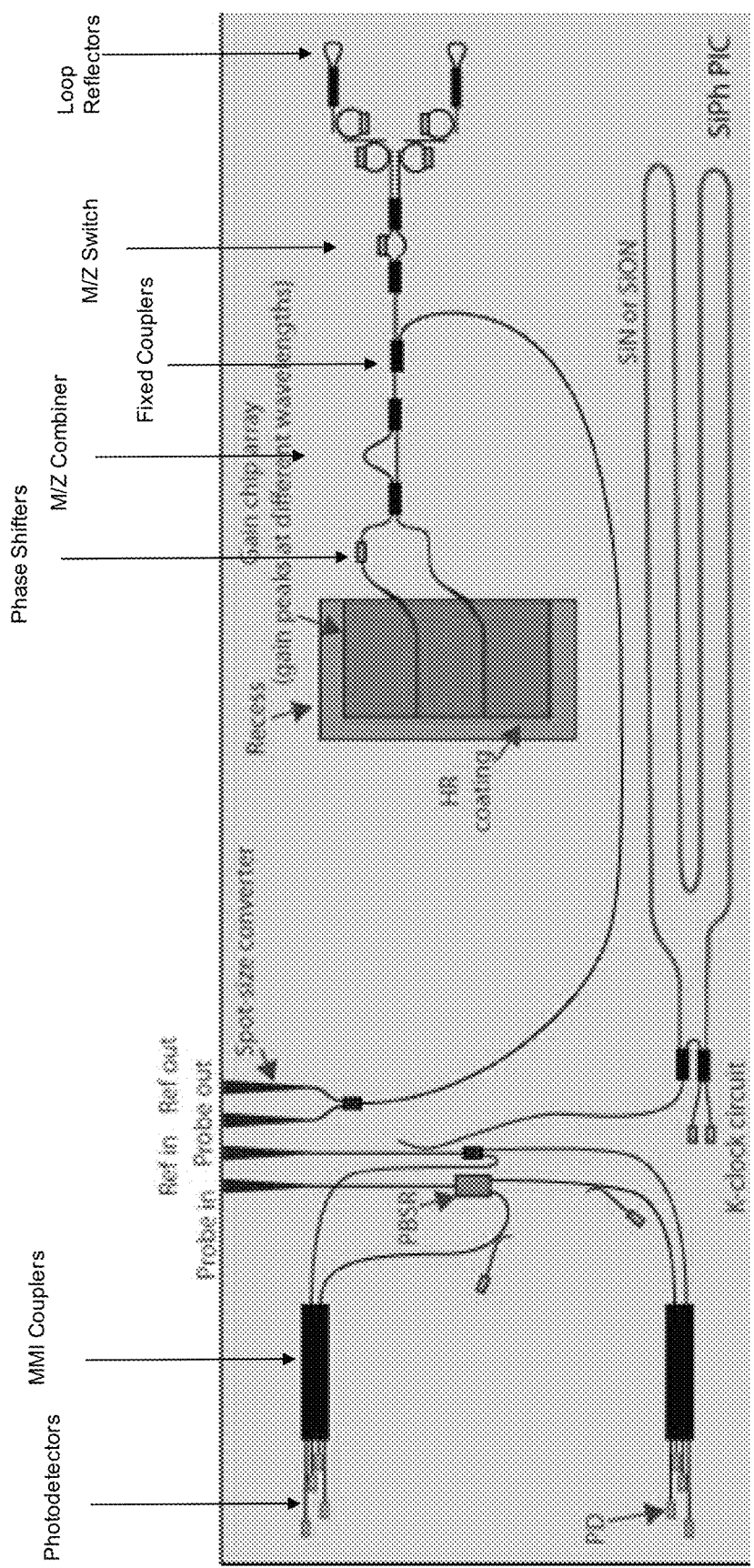
FIG. 20 shows a schematic block diagram illustrating a silicon PIC with an embedded gain chip employing end-face coupling and two sets of ring laser resonators according to an aspect of the present disclosure.
Figure 21:
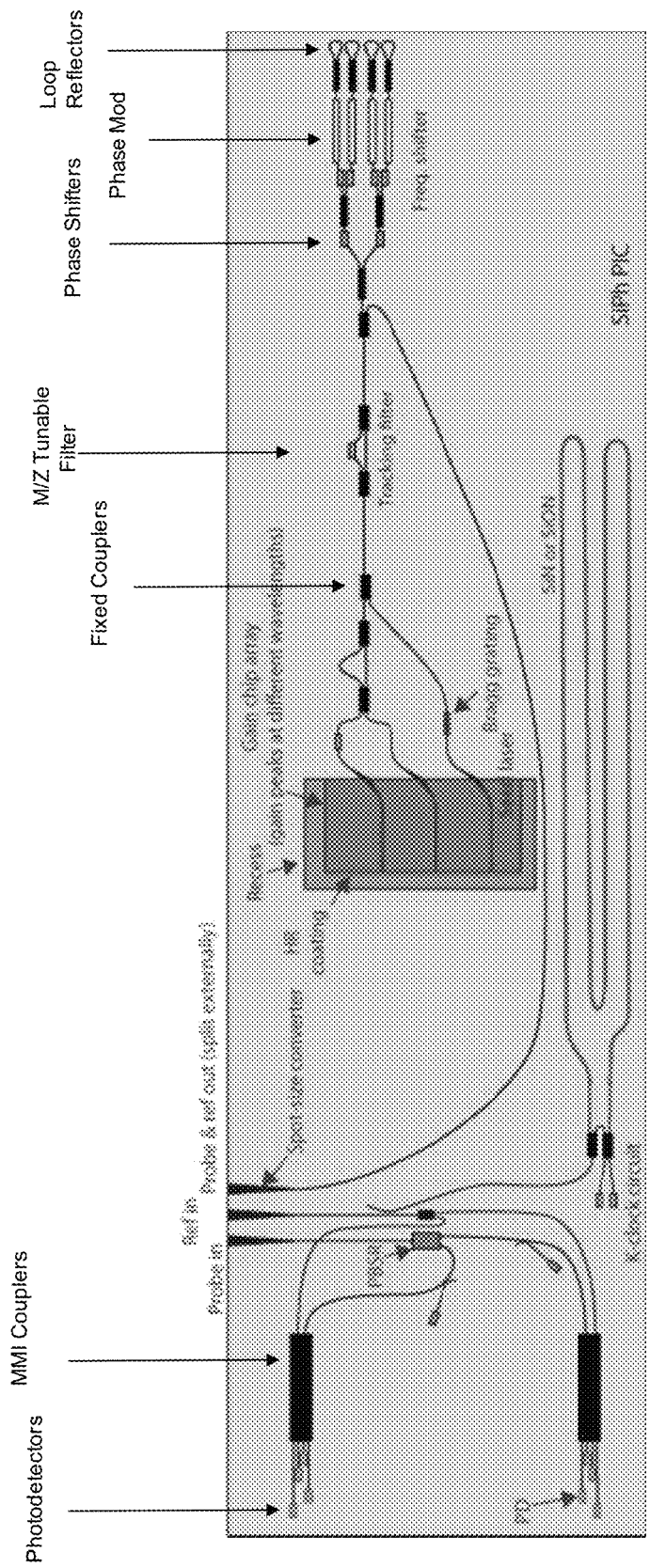
FIG. 21 shows a schematic block diagram illustrating a silicon PIC with an embedded gain chip employing end-face coupling and wherein the laser has a tunable tracking filter and an arbitrary modulator that can impart phase, frequency, or amplitude modulation on light within the laser cavity according to an aspect of the present disclosure.

For very broad coupling bandwidth, one can use facet couplers with spot-size converters as shown in FIGS. 19, 20, and 21. If these facet couplers are used instead of the 2D grating couplers, then the facet couplers must be followed by integrated polarization beam splitters and integrated polarization rotators in one output of the polarization beam splitters (PBSR).

An integrated polarization beam splitter can be, for example, a direction coupler in silicon wire waveguides that is 100/0 coupling for TM and nearly 0/100 for TE. A polarization rotator can be, for example, an adiabatic transformation that uses asymmetric waveguide structures/placements to achieve significant mode splitting when the waveguide modes are hybrid TE/TM modes.

Note in both FIGS. 18(a)-18(b) and 19 it is possible to configure using another embodiment that only has one frequency shifter in series with a tunable optical filter, or no frequency shifter at all and just tunable optical filters. It is also possible to add in PIC optical isolators using couplers and phase modulators.

FIG. 20 shows another illustrative embodiment integrated onto a SiPh PIC including with a widely tunable laser using tunable filters. As may be observed, a Mach-Zehnder interferometer (MZI) switch switches between two ring-resonator-based tunable filters. The ring resonators are Vernier tuned.

The tuning works as follows. The MZI sends the light to the upper tunable filter. The upper filter begins to tune from one end of the gain spectrum to the other. When the phase tuners in the rings run out of adjustment range, the second filter is adjusted to be at the same wavelength as the upper filter and same phase but using phase tuners set at the beginning of their ranges. The switch then switches and the lower filter tunes and the phase tuners in the upper filter reset.

When the lower filter exceeds its adjustment range, the switch switches back to the upper filter and the overall process continues. As may be appreciated, this type of swept laser may experience mode hops as the wavelength is tuned. However, phase tuners may be positioned in each ring resonator section such that they remain in a cavity mode and the switch operates every time one of these phase shifters exceeds its normal range. In this way the frequency sweeping could be mode-hop free or with reduced mode-hops. In order to be near mode-hop free, as the switch switches, the relative phase between the two paths is adjusted be zero, so that during the switching, which necessarily takes a finite amount of time, the laser does not mode hop. Also, other tunable filters could be substituted for these double-ring resonator structures.

Alternatively, if one does not care about the presence of mode hopping during tuning, then one could eliminate the switch and just one Vernier-tuned ring resonator set. In this case, one possibility is to drive the two ring resonators with programmed voltages via digital-to-analog converters so that the wavelength sweep is monotonic across the band. There would likely be mode hopping because the ring voltages would have to be non-monotonic and would have to reset at times. An alternative possibility is to drive one ring with a monotonic voltage waveform, leaving the other one substantially constant. This would cause the wavelength to tune in discrete steps. After this sweep of one ring, then the second ring could be adjusted a small amount and then the first ring swept again. This would allow one to eventually cover all the wavelengths in the band, but in a non-monotonic, moving-comb fashion. Post detection reordering of the frequency samples in a DSP unit could be used to perform the FFT.

In yet another illustrative embodiment of the structures depicted in FIG. 20 it is possible to use just one gain element in the gain chip thereby eliminating the M/Z combiner and reducing fabrication complexity at the expense of tuning range. It is also possible to reduce fabrication complexity and cost to use just one set of tunable filters and thus eliminate the M/Z switch in applications that require less tuning speed and tuning range.

Yet another illustrative embodiment according to the present disclosure is shown schematically in FIG. 21. In this illustrative embodiment shown in FIG. 21 there is a single frequency shifter and a tunable tracking filter constructed using a length-imbalanced Mach Zehnder interferometer having a large free-spectral range. As may be readily appreciated, a large free-spectral range makes tracking easier. A narrower band tunable tracking filter can be used but requires a more complicated filter structure if it is desirable to tune the whole frequency band without any resets. Also there is one output fact coupler/spot-size converter for the probe and reference outputs which are then split using an external splitter.

Figure 22:
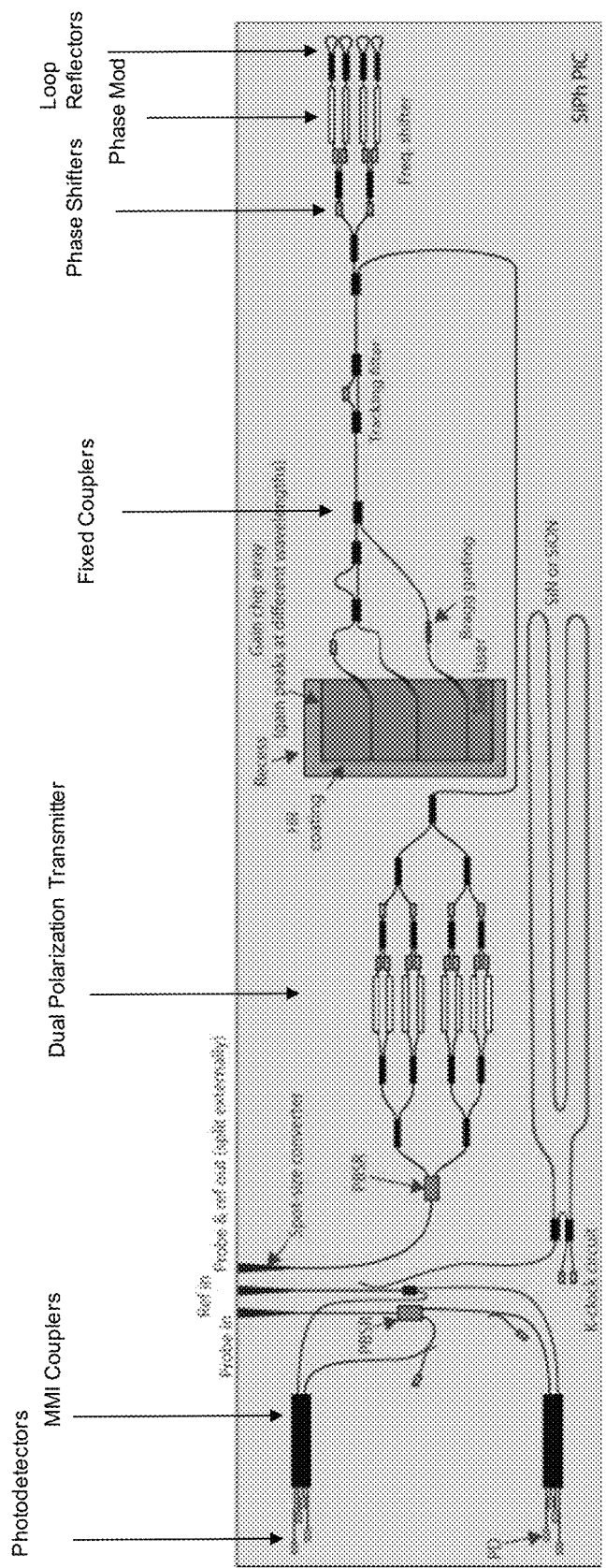
FIG. 22 shows a schematic block diagram illustrating a silicon PIC similar to that shown in FIG. 21 wherein the PIC includes a dual polarization I/Q modulator such as that shown in FIG. 7.

Yet another illustrative embodiment according to the present disclosure is shown schematically in FIG. 22. It contrast to the structures depicted in FIG. 21, the structure(s) of FIG. 22 includes a dual-polarization arbitrary I/Q modulator comprising out of phase shifters, splitters, combiners, and a Mach-Zehnder modulator. The various phase shifters are for adjusting optical path lengths and may be carrier depletion, or other types of modulators and may be thermal or electro-optically activated. The outputs of the two modulators are combined in a PBSR and it is also possible to use simpler absorptive types of modulators at the expense of higher loss. Other types of modulators are possible such as fast VOAs.

Figure 23A:
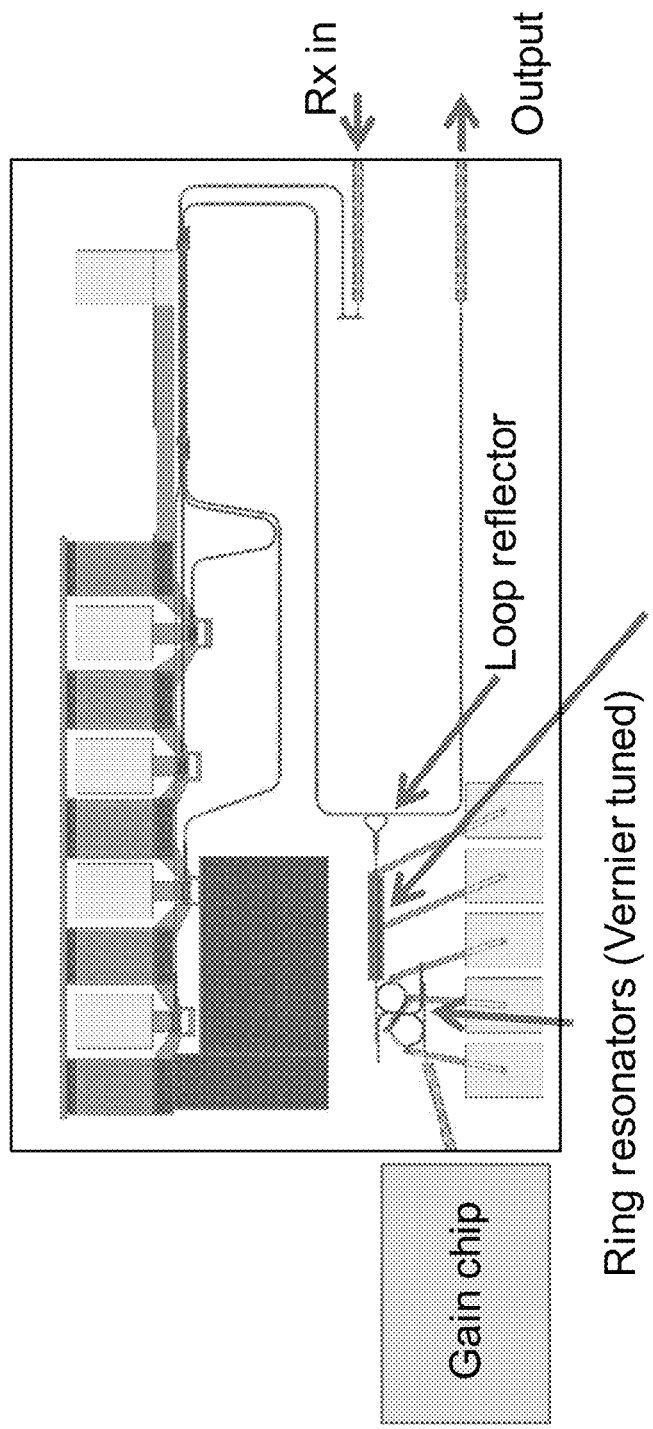
FIG. 23A shows a schematic block diagram illustrating a tunable laser transmitter and single polarization I/Q coherent receiver constructed on a single PIC.
Figure 23B:
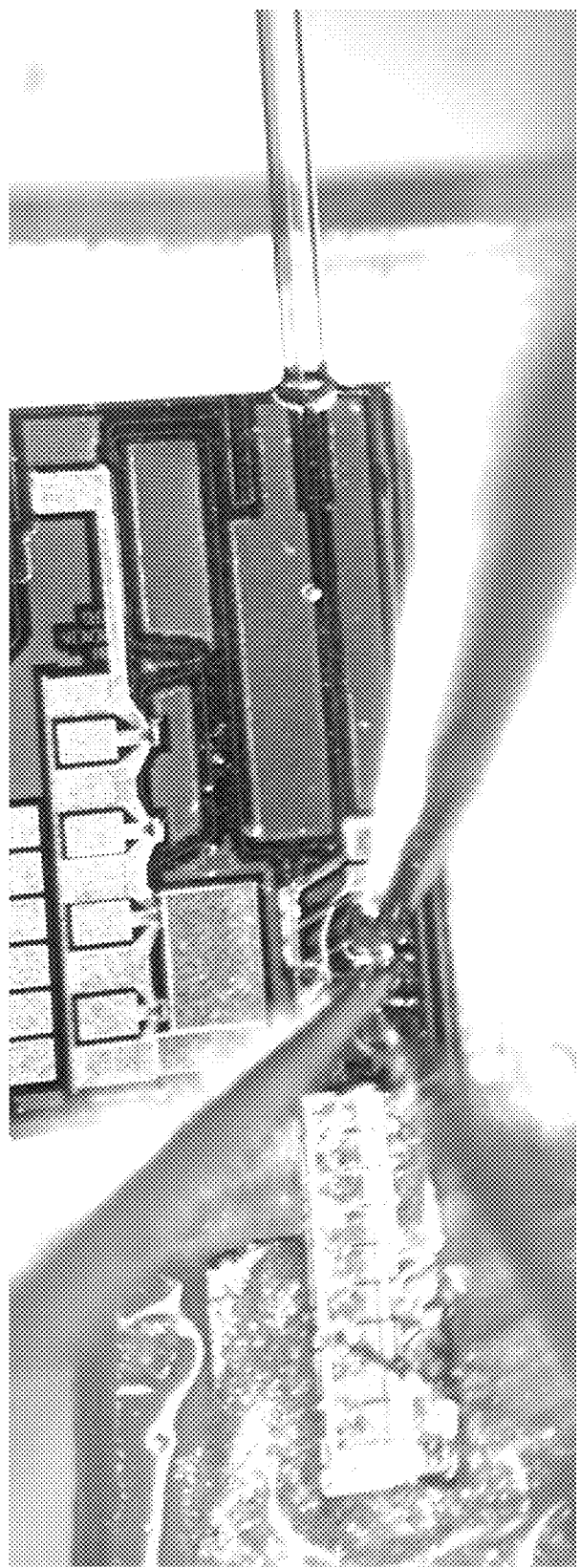
FIG. 23B shows a photograph illustrating a tunable laser transmitter and single polarization I/Q coherent receiver constructed on a single PIC of FIG. 23A.
Figure 23C:
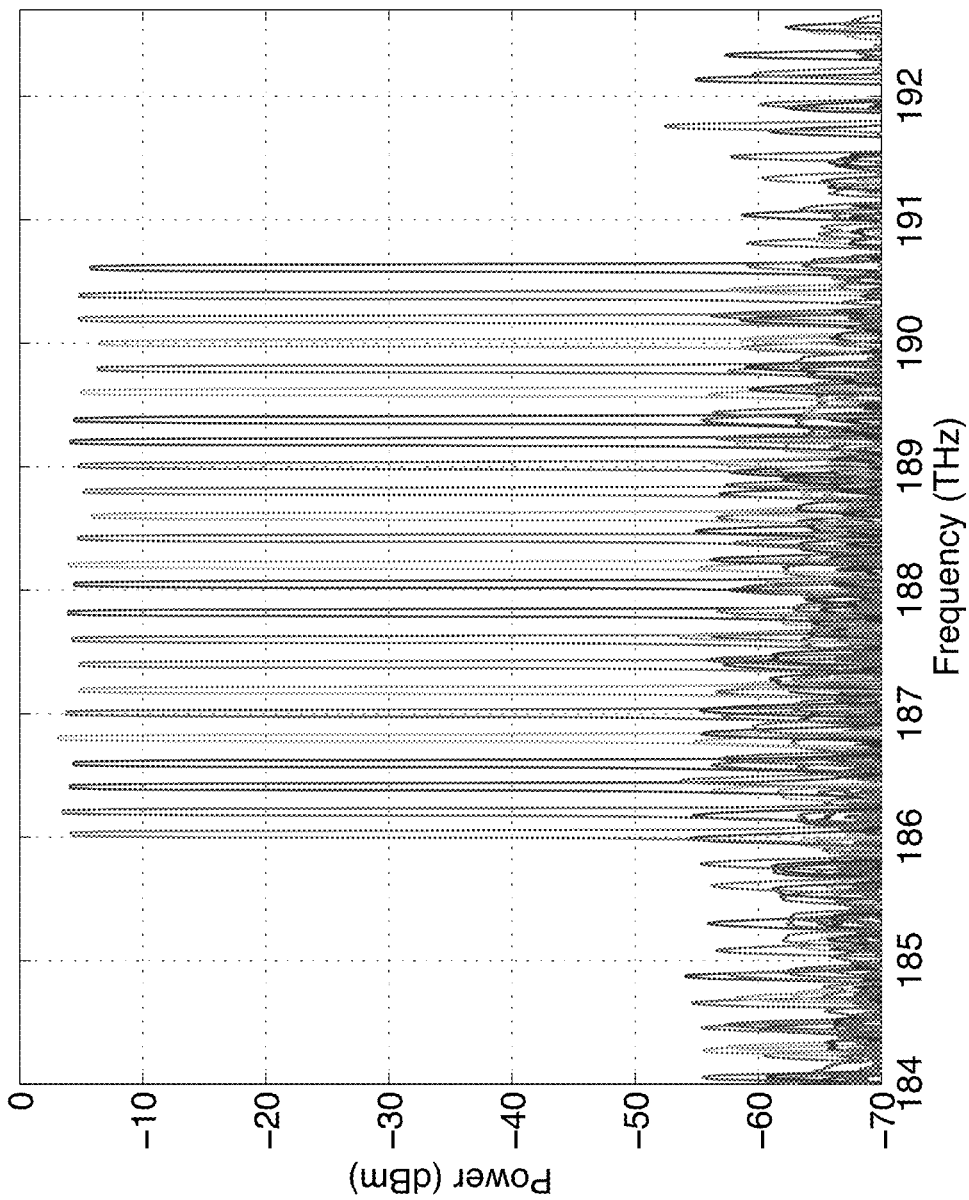
FIG. 23C shows a sample output of tunable laser spectrum of the tunable laser transmitter and single polarization I/Q coherent receiver constructed on a single PIC including schematic of FIG. 23A according to an aspect of the present disclosure.

FIG. 23(a) shows an illustrative example schematic of silicon PIC according to an aspect of the present disclosure. A receiver portion comprises a single-polarization dual-balanced I/Q receiver similar to that shown previously in FIG. 3. The PIC delay is included within the PIC. A laser contains InP gain chip butt coupled to a silicon photonic integrated circuit similar to that shown in FIGS. 18-22. The laser cavity includes of two Vernier tuned ring resonators, a fast phase tuner element, and a single loop reflector. The output waveguides are coupled to a facet coupler labeled "output" which further coupled to a single mode optical fiber. FIG. 23(b) shows a photograph of the device. FIG. 23(c) shows the output laser tuning characteristic over ~4.8 THz. Wider wavelength tuning is possible.

Note that the structures depicted in FIGS. 18-23 show an optical gain chip set into a silicon photonics PIC. There are a variety of other methods to add an optical gain compatibility with a silicon substrate such as using wafer bonding, regrowth, or directly doping the silicon PIC with germanium or rare earth dopants to provide gain. Furthermore it is possible to build the entire PIC out of another optically compatible medium such as InP, InAs, GaAs, GaAlAs, InGaAs, or many other optically compatible semiconductor materials. For example, it has been demonstrated that InAs quantum dot (QD) lasers can be applied directly to silicon to produce optical gain in the 1.3 um region. Some of these cited approaches can have the benefit of providing gain in one medium but the disadvantage of being less compatible with the silicon processes commonly used in semiconductor foundries.

To couple from a PIC to either a fiber or free space optics, a broadband low-loss coupling is needed. As discussed earlier, two common methods to achieve this are surface grating couplers and fact coupling (also referred to as end-coupling or butt-coupling). Such coupling is needed at the interfaces from the integrated components (dotted lines in FIGS. 2-7 and in the Probe out, Ref Out, Probe In, and Ref In of FIGS. 18-23) or wherever there are input/output locations where light travels on or off the PIC.

Figure 24:
FIG. 24 shows a schematic block diagram illustrating a fiber assembly including three single mode optical fibers coupled to three surface grating couplers on a silicon PIC according to an aspect of the present disclosure.

Coupling may also be needed—as discussed earlier—if the swept source laser contains optical path lengths in fiber, and/or if the increased delay is needed between the 9/10 coupler and the k-clock input. As discussed earlier in some particular embodiments PIC surface grating couplers are used and in other embodiments facet/end/butt coupling is used. To achieve a robust and manufacturable system, it is convenient to place multiple fibers (2, 3, 4, or more depending on the system requirements) in a single glass block that is precisely manufactured to have the same dimensional separation between fibers as the separation of the PIC inputs and outputs. The fibers can be housed and secured in the glass block using epoxy and polished as a unit to ensure low-loss coupling. A manual or automatic multi-axis machine can be used to align the glass block to the fiber waveguide interfaces on the PIC. FIG. 24 shows and example of a low loss fiber assembly housing three single mode optical fibers coupled to a silicon photonic circuit containing modulators and receiver that we have constructed.

Figure 25A:
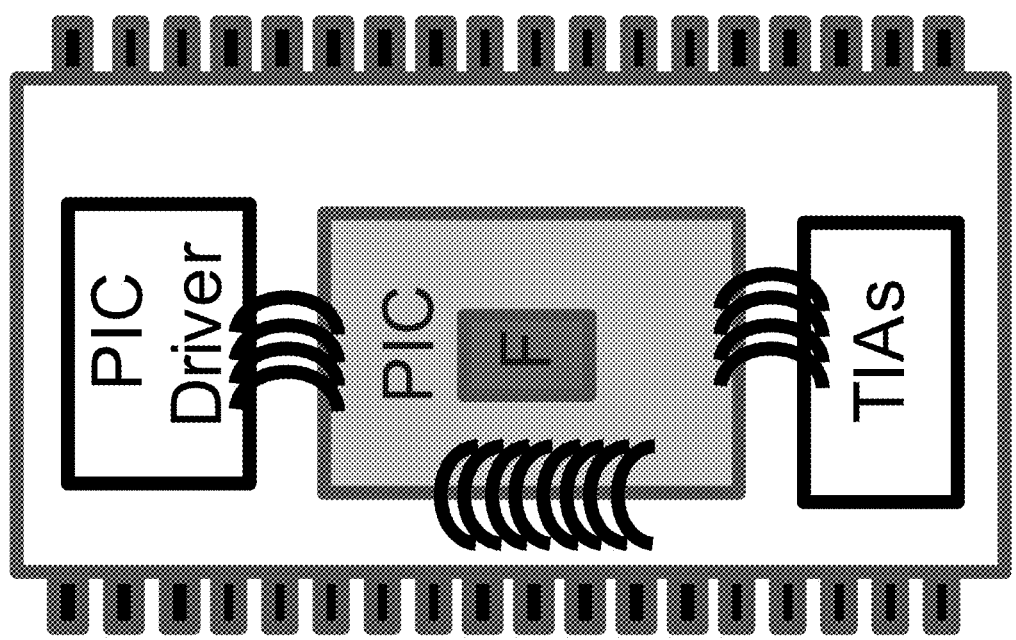
FIG. 25A shows a schematic block diagram illustrating a PIC packaged with various electronic components.
Figure 25B:
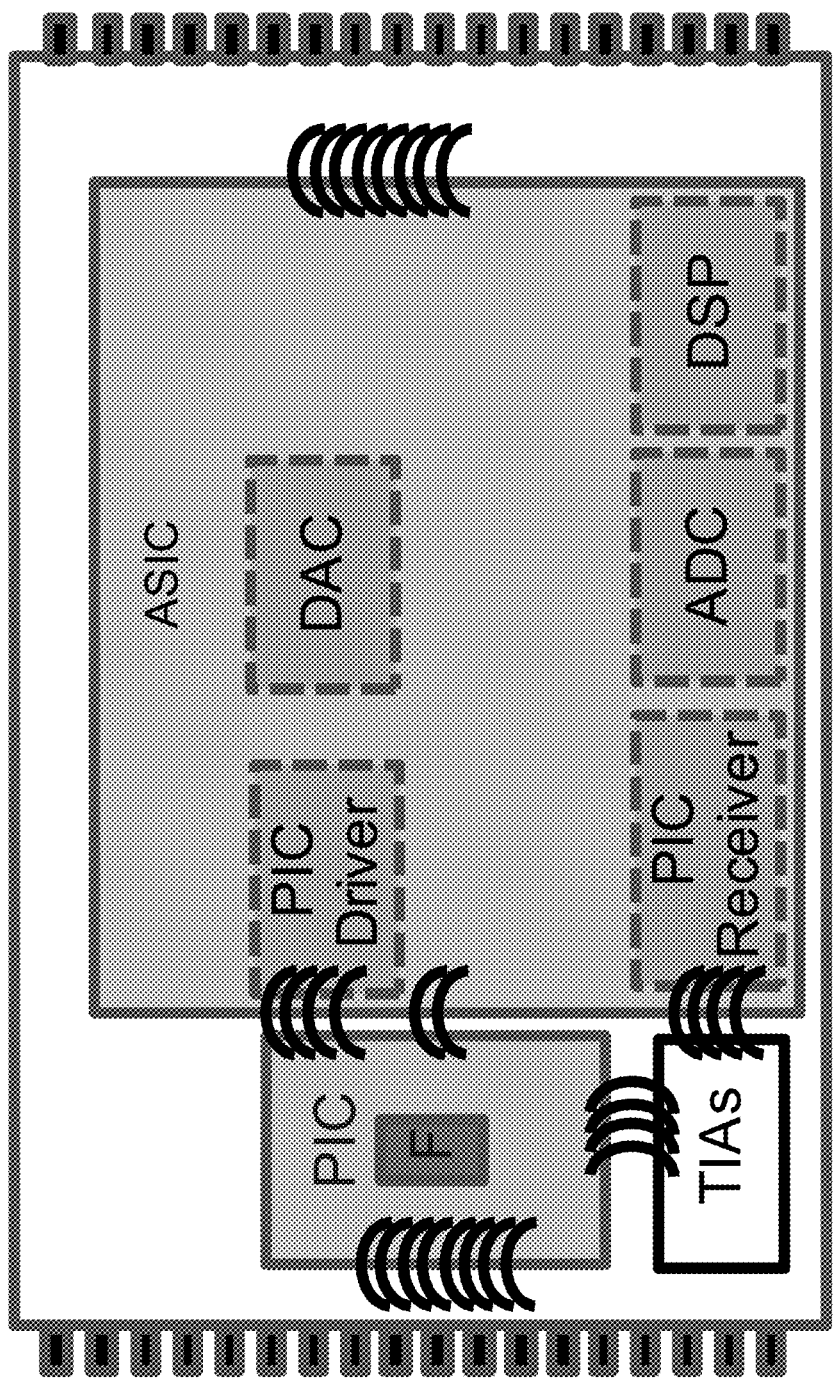
FIG. 25B shows a schematic block diagram illustrating a PIC packaged with various electronic components.
Figure 25C:
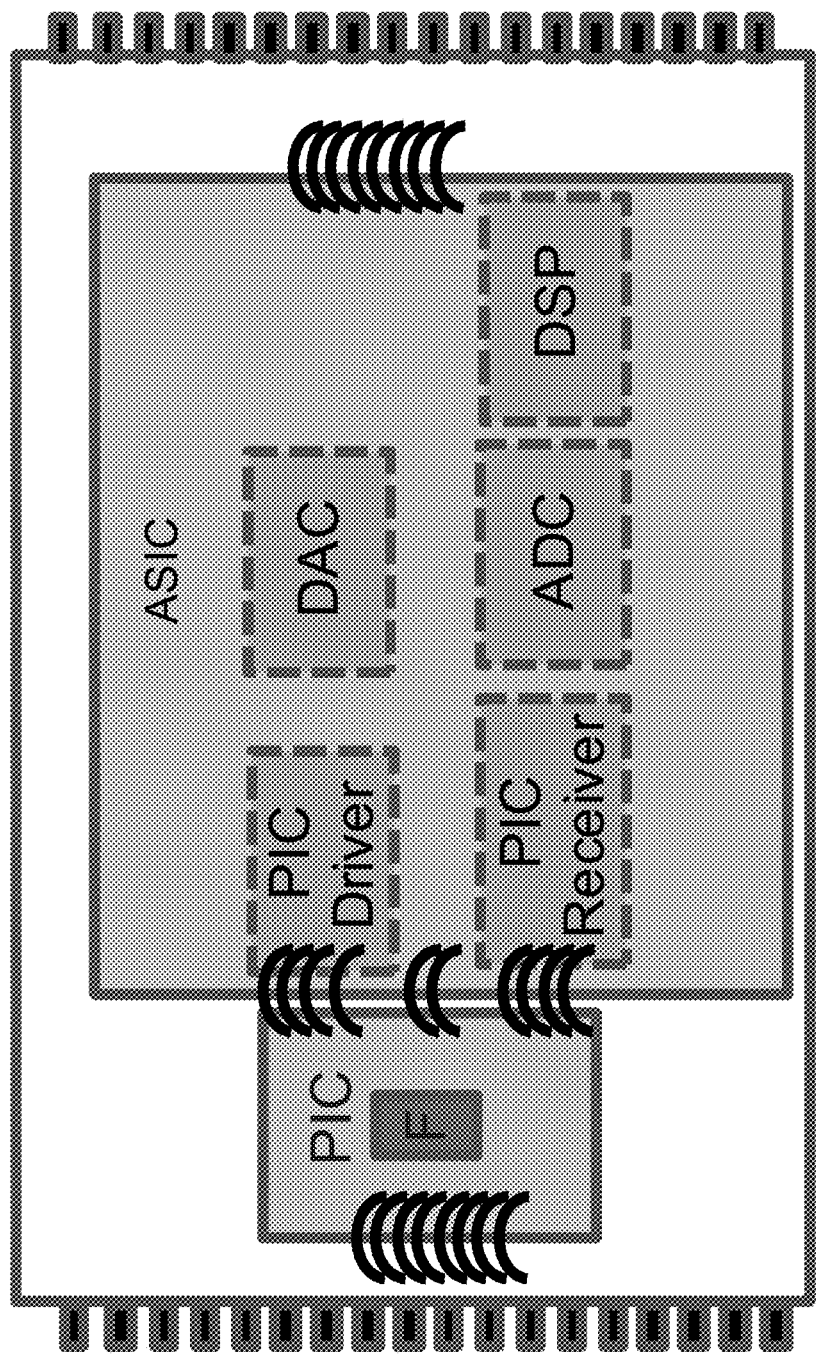
FIG. 25C shows a schematic block diagram illustrating a PIC packaged with various electronic components.

A PIC may be housed our otherwise contained in any of a number of optical mechanical packages known in the art. However it is highly beneficial if the PIC is closely integrated with the transimpedance amplifiers (TIA) and that both are contained in one package. There are several methods for achieving this proximity as shown in FIGS. 25(a)-25(c) which depict co-packaging of the PIC and electronics. FIG. 25(a) shows the PIC mounted in a ceramic or metal package, wirebonded with TIAs and driver circuits. The driver circuit may contain modulator drivers, phase shifter drivers, thermal drivers, and DACs, among other components.

Alternatively those active electrical components may be located external to the package. FIG. 25(b) shows an example where the PIC is co-packaged with the TIAs and a digital circuit such as an ASIC, FPGA, or other mixed signal electronics.

FIG. 25(c) shows an example embodiment in which the TIAs are further integrated with an application specific integrated circuit (ASIC). Wire bonds, die bonds, wafer stacking, and other approaches can be used to optically, mechanically, and electrically interface with the PIC.

Figure 26:
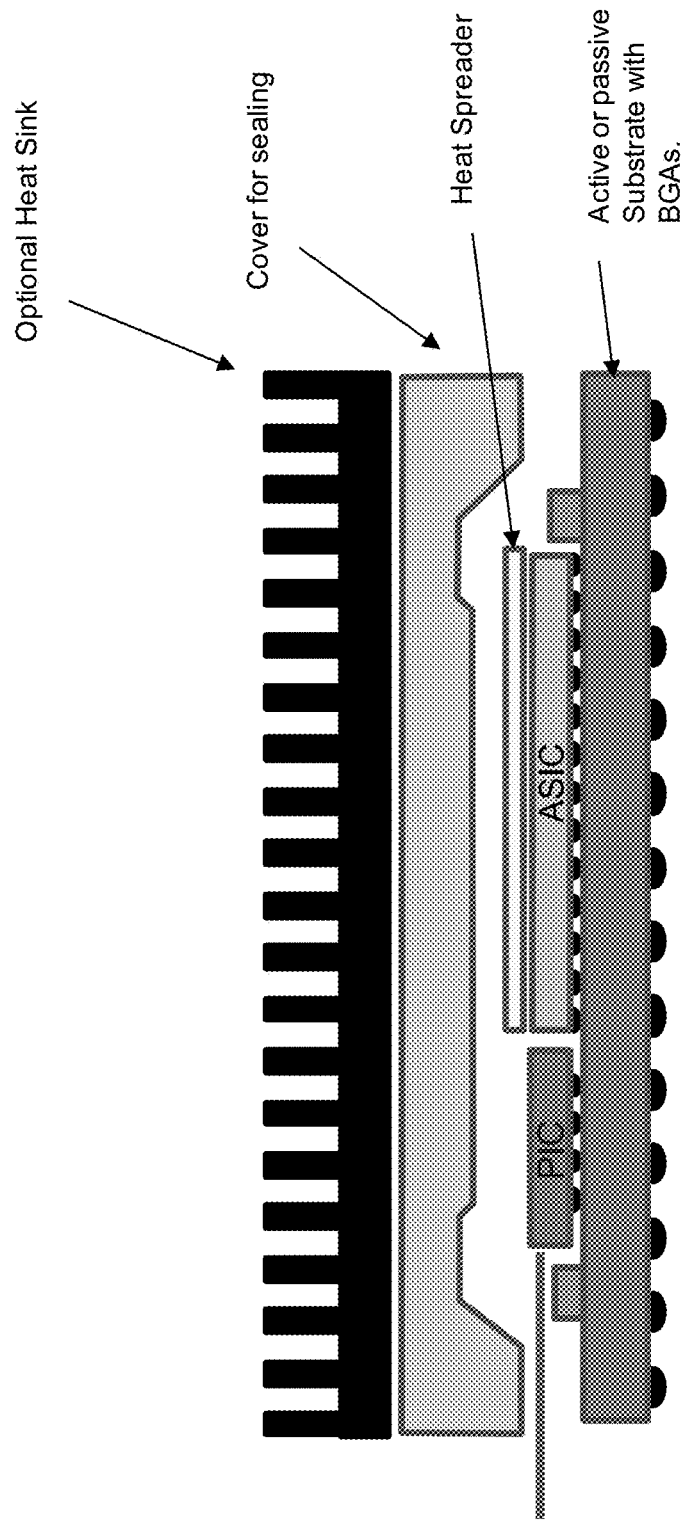
FIG. 26 shows a schematic block diagram illustrating an exemplary PIC and electronic circuit on a carrier substrate according to an aspect of the present disclosure.

FIG. 26 shows an illustrative example where the PIC and ASIC are die bonded to a substrate that may comprise silicon, FR4, or another suitable substrate carrier that also contains ball bonds. It is possible to replace the substrate ball bonds with leads or pins in alternate embodiments. The substrate carrier could be active or passive device. Also shown is a metal cover and heat sink and thermal coupler to connect the top of the ASIC to the cover and heat sink.

As may now be readily apparent to those skilled in the art, interferometric ranging, sensing, imaging and communication systems such as swept source optical coherence tomography (SS-OCT) systems or free-space optical communication systems can greatly benefit from increases in photonic integration. Significantly, photonic integration offers the potential of reduced size, lower costs, and improved performance.

As may be further appreciated, many such systems require lateral scanning to produce a 2D or 3D image of a sample's optical properties. Free space optical communication systems require active pointing and/or tracking of narrow beams. And while such scanning may be accomplished through the effect of electro-mechanical scanning such as galvanometric beam scanners, MEMs scanners, PZTs, or rotating fibers—among others. These electro-mechanical approaches oftentimes characterized by high cost, large size, and relatively poor performance. In sharp contrast—and according to an aspect of the present disclosure—photonic phased arrays offer the potential to implement electronic scanning of the light and can be compact, low-cost, fast, and can enable a wide variety of other important optical functions such as compensation of aberrations, extended depth of focus, and focus adjustment.

Figure 27:
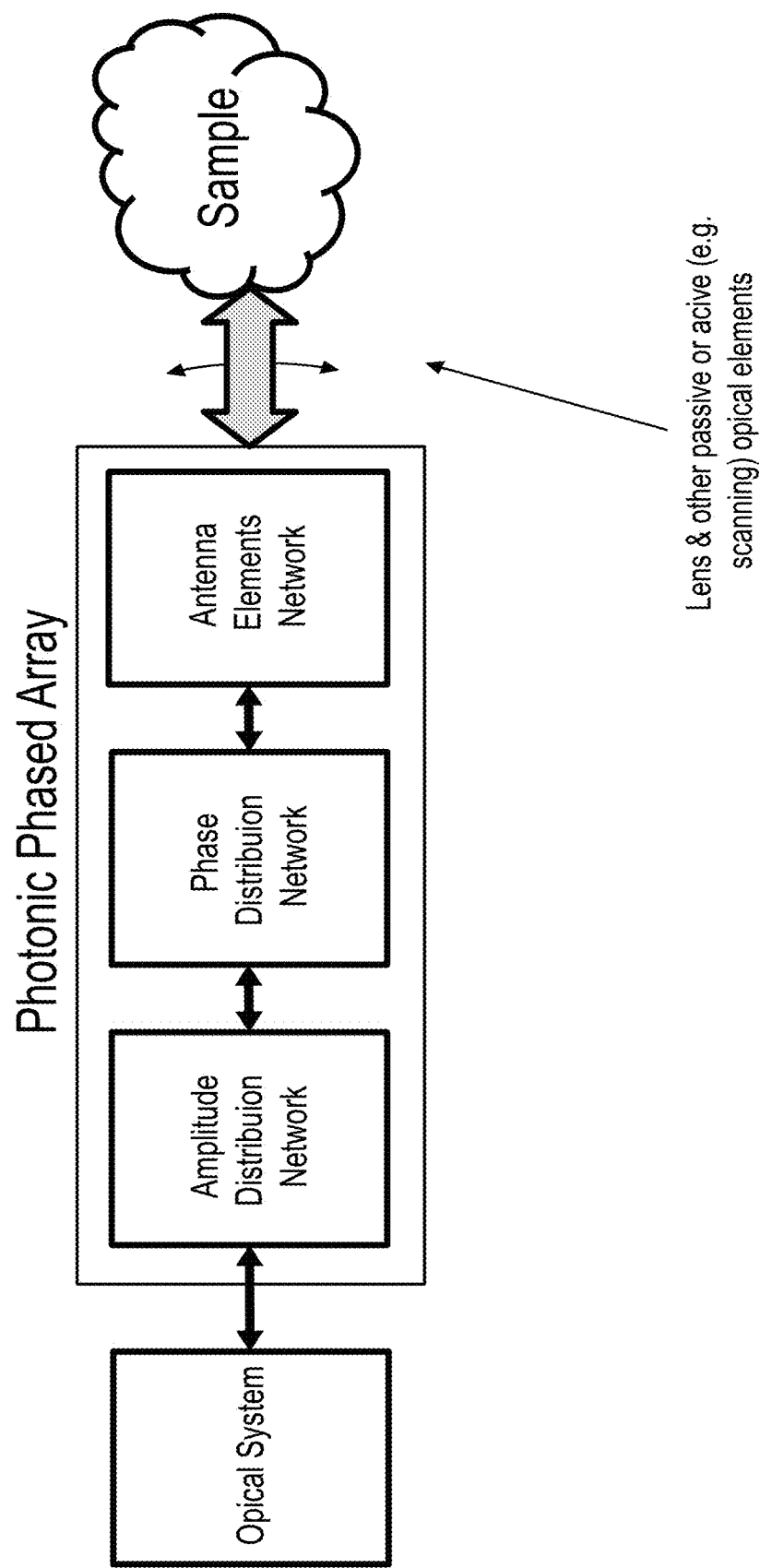
FIG. 27 shows a schematic diagram illustrating a photonic phased array concept according to an aspect of the present disclosure wherein elements of the phased array include an amplitude distribution network, a phase distribution network, and the antenna elements network (note that while the diagram shows three sequential boxes, the order of the boxes can be different and the actual implementation can be such that the amplitude and phase are implemented in a distributed fashion)

Turning now to FIG. 27 there it shows a schematic showing an illustrative example a photonic phased array according to an aspect of the present disclosure. As may be understood by reference to FIG. 27, light from an optical system—for example an SS-OCT system or an optical communication transceiver—is coupled into a photonic phased array including one or more networks that control the amplitude and phase of the light hitting each antenna network element. As depicted therein, a sequential flow of an amplitude distribution network, phase distribution network, and antenna elements network are shown. Notably—and as may be appreciated—that there are different topologies that can be used. For example, in an illustrative embodiment gain and phase elements may be distributed as opposed to being arranged as distinctly cascaded blocks. In addition, amplitude and phase elements may be fixed in time (static) or one or more of them may be adjustable. Finally, the antenna array may be a linear 1D array or 2D array.

As may now be appreciated, there exist applications of fixed amplitude and phase including the implementation of complex optical fields that can compensate for aberrations between the photonic phased array and the sample, or implement extended depth of focus (e.g. extending the Rayleigh range) over which the light remains tightly focused within the sample. Another example of an application for a fixed amplitude and phase phased array is an SECM like application where angular tuning is accomplished by tuning the wavelength of the source.

In one exemplary embodiment the amplitude distribution to each antenna element is fixed and phase elements are adjustable in response to electronic commands (electronic system not specifically shown in FIG. 27). By adjusting the phase distribution to the antenna element network the beam may advantageously be scanned in one or two dimensions. One may also simultaneously incorporate the above mentioned aberration correction and extended depth of focus with 1D or 2D scanning. It is also possible to actively adjust the focus.

As noted in FIG. 27 there could be, and often are, additional passive optical elements such as lenses, windows, sheathing, fold mirrors, and other active optical and electrooptical elements between the photonic phased array and the sample.

Notably, there are a wide variety of antenna elements that may be employed including surface grating couplers, small apertures over coupled waveguides, and end-facet coupling to name just a few. It is well known that the output field from a phased array is the product of the antenna element pattern and the array pattern and that by controlling the intensity of the elements near the edges, the side-lobes in the far field are reduced.

Figure 28:
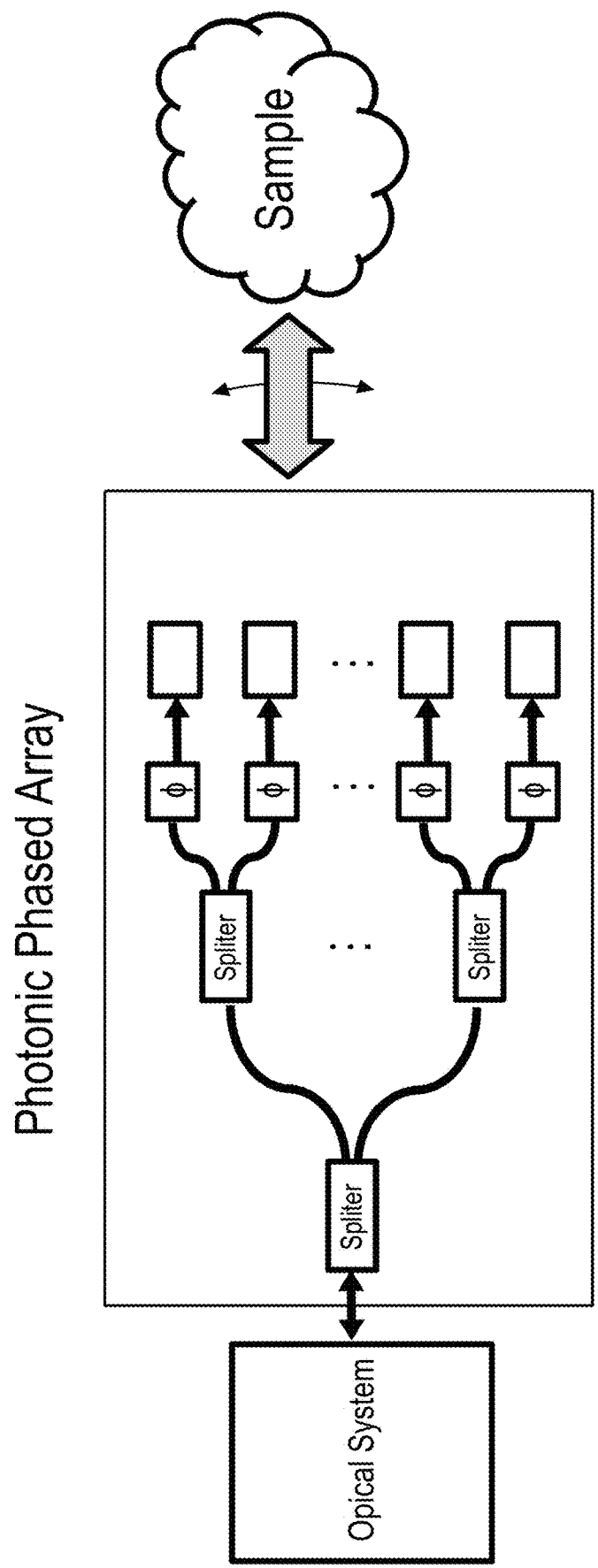
FIG. 28 shows a schematic illustrating a series of waveguide splitters followed by phase adjusters followed by surface grating couplers according to an aspect of the present disclosure.

An illustrative embodiment of the concepts introduced in FIG. 27 is shown schematically in FIG. 28. As depicted therein, light from the optical system is coupled to a series of one or more splitters. The splitters can be direction couplers, MIMI devices, or other suitable power splitting devices. Even active adjustable splitting ratios are possible using approaches such as tunable Mach-Zehnder splitters The split ratios can be equal but in alternative embodiment(s) they are not equal to advantageously provide minimal side lobes in the far field.

Coupling of the optical system to the photonic phased array can be via an optical fiber or lenses or alternatively may be accomplished by integrating some or all of the optical system on the same substrate as the photonic phased array. It is also possible to have two photonic integrated circuits in close proximity with facet coupling between substrates.

Note that as shown in FIG. 28, the elements of the array can be a 1D array (as shown) or the antenna elements can be arranged in a 2D array. A 1D phased array may exhibit an advantage over a 2D phased array in that the antenna elements can be located very close together to minimize side-lobes or higher-order interference. In a 1D embodiment if the antenna elements have wavelength dependent emission angle, as is the case with many types of surface grating emitters, then the angular pattern can be tuned in one dimension by wavelength tuning of the source (or receiver) and tuned in the other dimension by phase tuning of the antenna elements. In another illustrative embodiment the elements can be located in an arbitrary N×M rectangular pattern or a circularly symmetric pattern or any other 2D pattern and 2D scanning can be implemented.

Note that some photonic antenna element designs, depending on how they are fed, operate mainly on one polarization mode. It is possible to design into the antenna element, or its optical feeding structure, polarizers to reduce or eliminate unwanted polarization propagation. Conversely it is possible to design a photonic phased array that can receive two nearly orthogonal polarizations. This is possible, for example, by using surface grating couplers, and coupling the first polarization mode of the antenna element to a first amplitude and phase distribution network and coupling the second polarization mode to a separate second amplitude and phase distribution network. Another approach is to have two antenna element networks, one for a first polarization mode and one for a second polarization mode that are sent to separate receivers.

Figure 29:
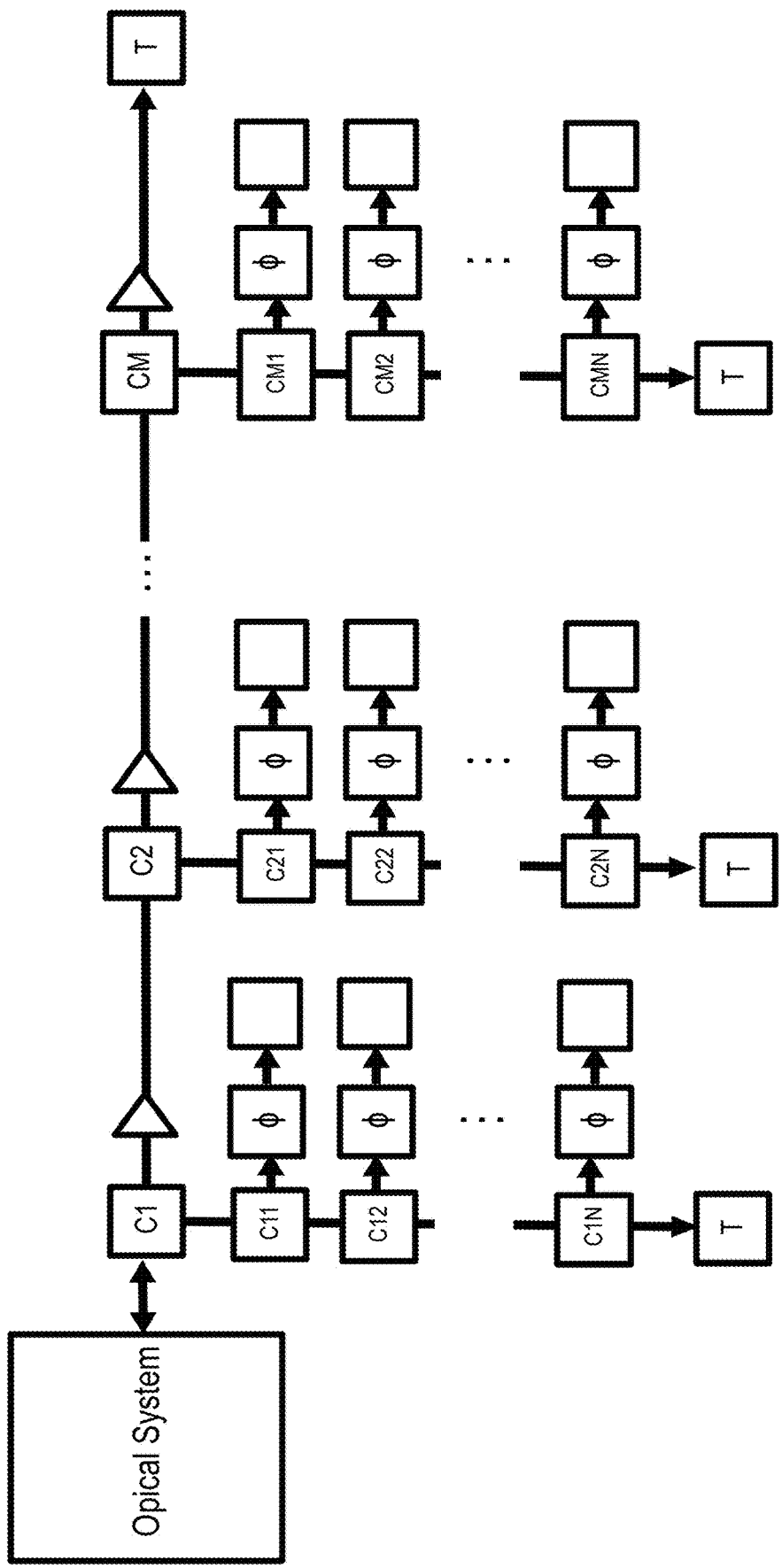
FIG. 29 shows a schematic illustrating a two dimensional phased array of size N×M according to an aspect of the present disclosure.

Turning now to FIG. 29 there is shown a schematic of an illustrative N×M rectangular embodiment of a photonic phased array that exhibits a different feed structure than that depicted in FIG. 28. Light from the optical system is coupled via optical fiber, waveguide, or lenses or other suitable methods to a network of optical busses. Along the top of the diagram depicted in FIG. 29 is a column bus including directional couplers (or other types of couplers) that tap off light into a series of columns busses. The coefficients C1 through CM can be designed to set the amount of light power delivered to each row to be equal or in alternative embodiments may be anodized to minimize far field side lobes. Each column has further directional couplers Ci1 through CiN that couples light into a phase shifter and then to an antenna element.

Note that the column coupling can be passive or active and optical gain elements can be used to boost the signal at the expense of design and fabrication and control complexity. In one exemplary embodiment the coupling coefficients are static and no optical gain elements are used in the photonic array.

As mentioned above, the column and row coupling coefficients can be tailored to minimize side lobes or a uniform antenna power profile can be achieved. It is possible to integrate VOAs (variable optical attenuators) into the waveguide row or columns or antenna elements at the expense of fabrication and operation complexity. It is useful to minimize reflections and termination of unused light (see elements in FIG. 29 marked by "T"). Similarly, all the other structures in the photonic phased array may be designed to minimize unwanted reflections including the antenna elements themselves.

As may be readily appreciated by those skilled in the art, a variety of phase control elements can be implemented in structures/systems according to the present disclosure. For example, in one illustrative embodiment a phase shifter includes thermal heaters positioned on top of optical waveguides. A series of electrically isolated column and row metal traces or wires are overlaid on top of the N×M photonic array. Alternatively, carrier injection, carrier depletion, or other electro-optical techniques may be employed.

Figure 30A:
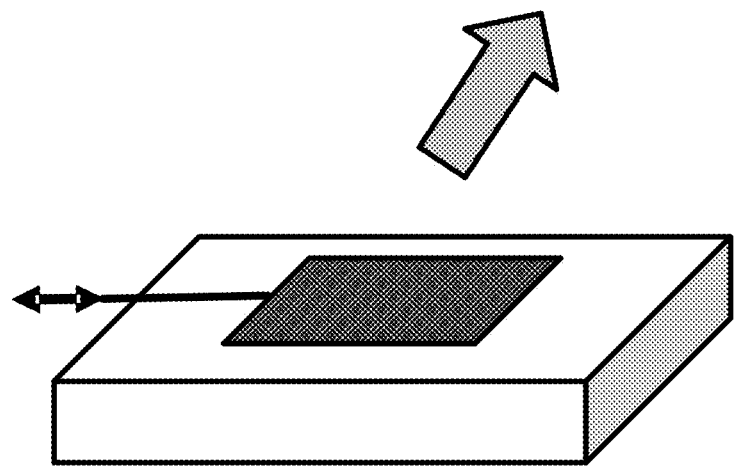
FIG. 30A shows schematic examples of an input coupling via end-facet coupling and a 2D phased array emitting substantially out-of-plane of the photonic chip.

With reference now to FIG. 30(a), there is shown in schematic form an illustrative example wherein light is coupled into a photonic phased array using end-facet coupling from, for example, an optical fiber and the photonic phased array emits light substantially out of the plane of the photonic chip. As may be readily appreciated, the phased array may be a 1D or a 2D (as shown) array.

Figure 30B:
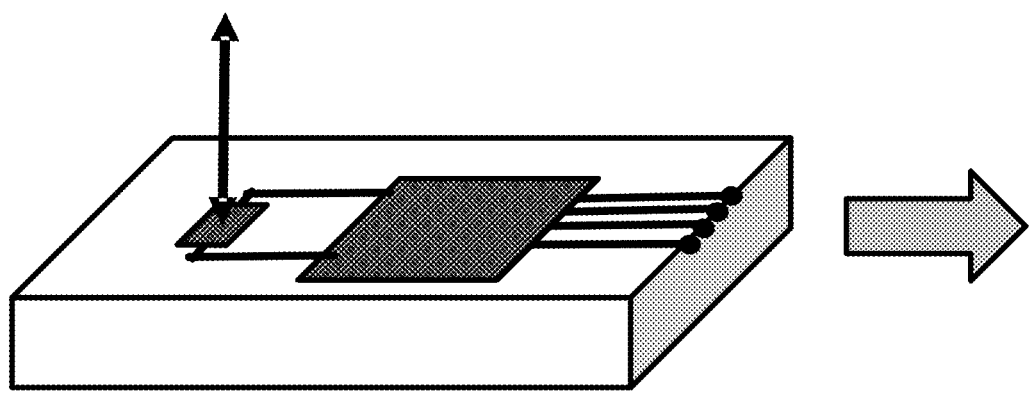
FIG. 30B shows an input coupling via a surface grating coupler and a 1D phased array emitting along one output facet via end-facet coupling according to an aspect of the present disclosure.

FIG. 30(b) shows an illustrative example wherein input light from the optical system is coupled via a surface grating coupler and the photonic phased array is a 1D array that uses facet output coupling. An alternative arrangement to couple input light to that shown in FIG. 30(b) is instead of coupling from the top of the chip, couple the input light via the back side of the photonic chip by etching and thinning the wafer near the vicinity of the input surface grating coupler. This approach can be used for any of the embodiments shown in FIGS. 30(a), (b), or (c). Such an approach may be particularly attractive when used for forward scanning in an endoscope configuration such as discussed later with respect to FIG. 33(b).

Figure 30C:
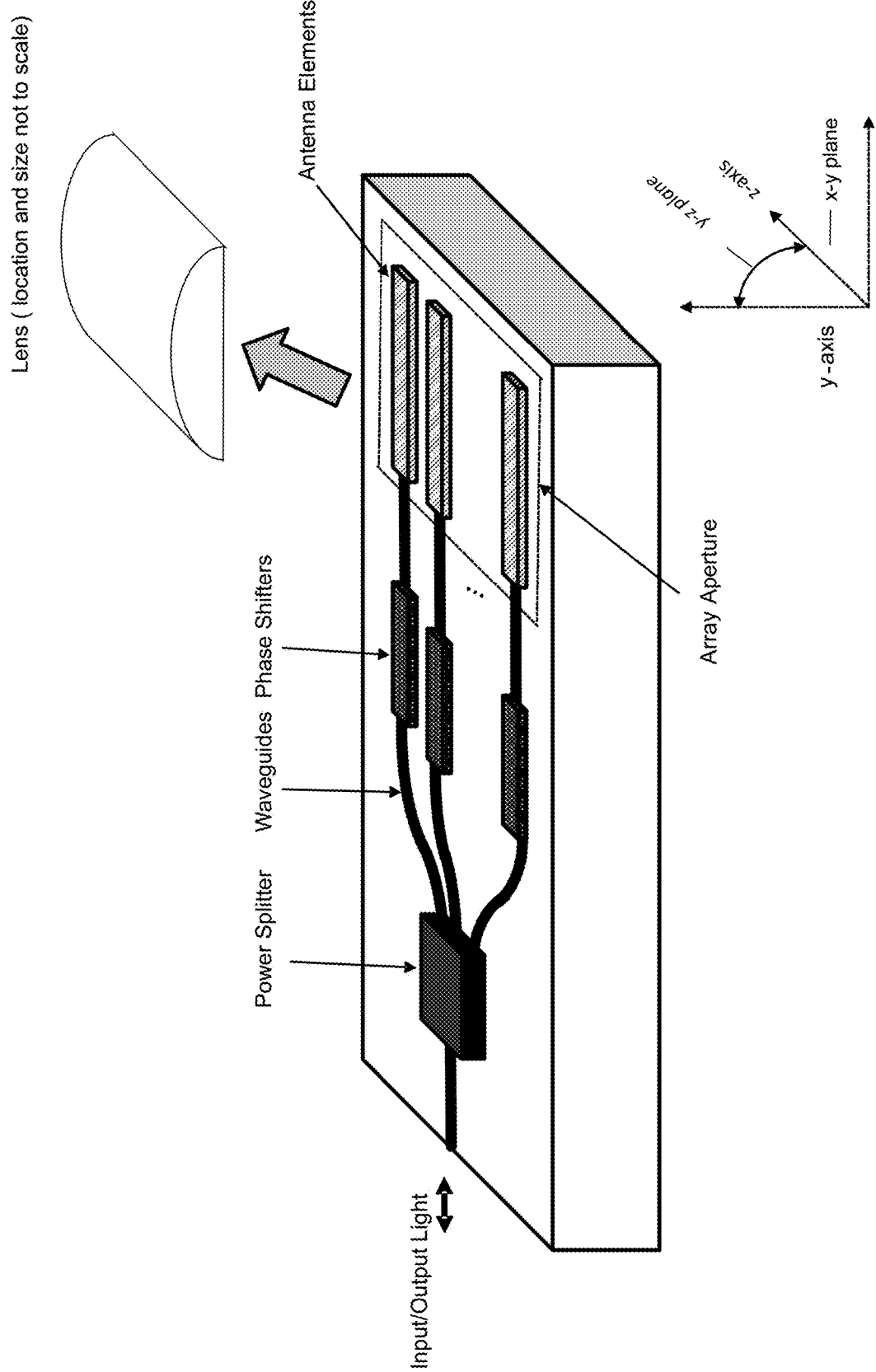
FIG. 30C shows a 1D phased array emitting substantially out-of-plane of the photonic chip using end-facet input coupling according to an aspect of the present disclosure.

FIG. 30(c) depicts an illustrative embodiment of an integrated photonic 1D phased array. Light from an optical system (not specifically shown) is coupled into an input optical waveguide, for example, using end facet coupling (as shown) or a surface grating coupler. The input light is coupled to a power splitter. The split ratio of the power splitter may be uniform or may be tailored to minimize side-lobes as is known in the art of antenna array theory. As may be further observed from that FIG. 39(c), the inset shows with curved double arrow X Y plane and the Y Z plane.

The power splitter directs light via optical waveguides to phase shifters. The phase shifters may be thermally driven or carrier injection, carrier depletion, or employ other electro-optical effects. Phase shifters are connected to electrical signal control lines (not shown). The output of the phase shifters is coupled to antenna elements.

In one illustrative embodiment the antenna elements are closely spaced in the z-dimension to minimize side-lobes. By increasing the number of antenna elements (z-dimension), the beam divergence in the y-z plane can be reduced. If the array aperture in the x-dimension is much smaller than the array aperture in the z-dimension, the beam divergence in the x-y plane will be larger than the divergence in the y-z plane. To allow light from the phase array to be effectively focused into a sample, it is sometimes desirable to have roughly a symmetric focal spot.

To accomplish this, an optional cylindrical lens can be located where the beam waists are substantially the same (alternatively anamorphic prism-pairs can be used). Using this lens, in combination with additional lenses and/or proper phasing of the phase shifters, allows the light to focus into a sample of interest and to collect light from a sample. If the antenna elements are elongated such that the emission is over an effective area such that the array aperture is closer to equal in the x-z plan, a cylindrical lens is not needed.

Phase scanning is accomplished by adjusting the phase shifters as is known in the art of antenna array theory. In one preferred embodiment, angular scanning of the peak of the emission is accomplished in the y-z plane in response to changes in the phase shifters. As mentioned above, by proper phasing a curved phase front emitted from the array can also be achieved simultaneously with angular scanning.

Those skilled in the art will appreciate that it is possible that the antenna elements have an emission angle in the x-y plane that is wavelength dependent. This can be achieved by a variety of methods including the use of some types of surface grating couplers. In such an embodiment it is possible to steer the emission from the photonic phased array shown in FIG. 30(c) in the x-y plane by tuning the wavelength of the input light and have additional angular tuning in the y-z plane by tuning the phase shifters. Thus 2D scanning can be achieved. If a wavelength tunable optical source, similar in characteristic to that used in an SS-OCT system, is used then the sample can be scanned in the x-y plane via wavelength tuning and in the y-z plane via phase tuning. Light backscattered from the sample (not specifically shown) is collected via reciprocity and directed into the input optical waveguide back to the optical system (not specifically shown). Advantageously, the optical system may be a coherent optical receiver or an incoherent optical receiver. Note that it is also possible to have a combination of phased array scanning in one dimension (e.g., Y-Z plane) and additionally have more traditional scanning in either the same plane or in another plane (e.g., X-Y plane).

Figure 31:
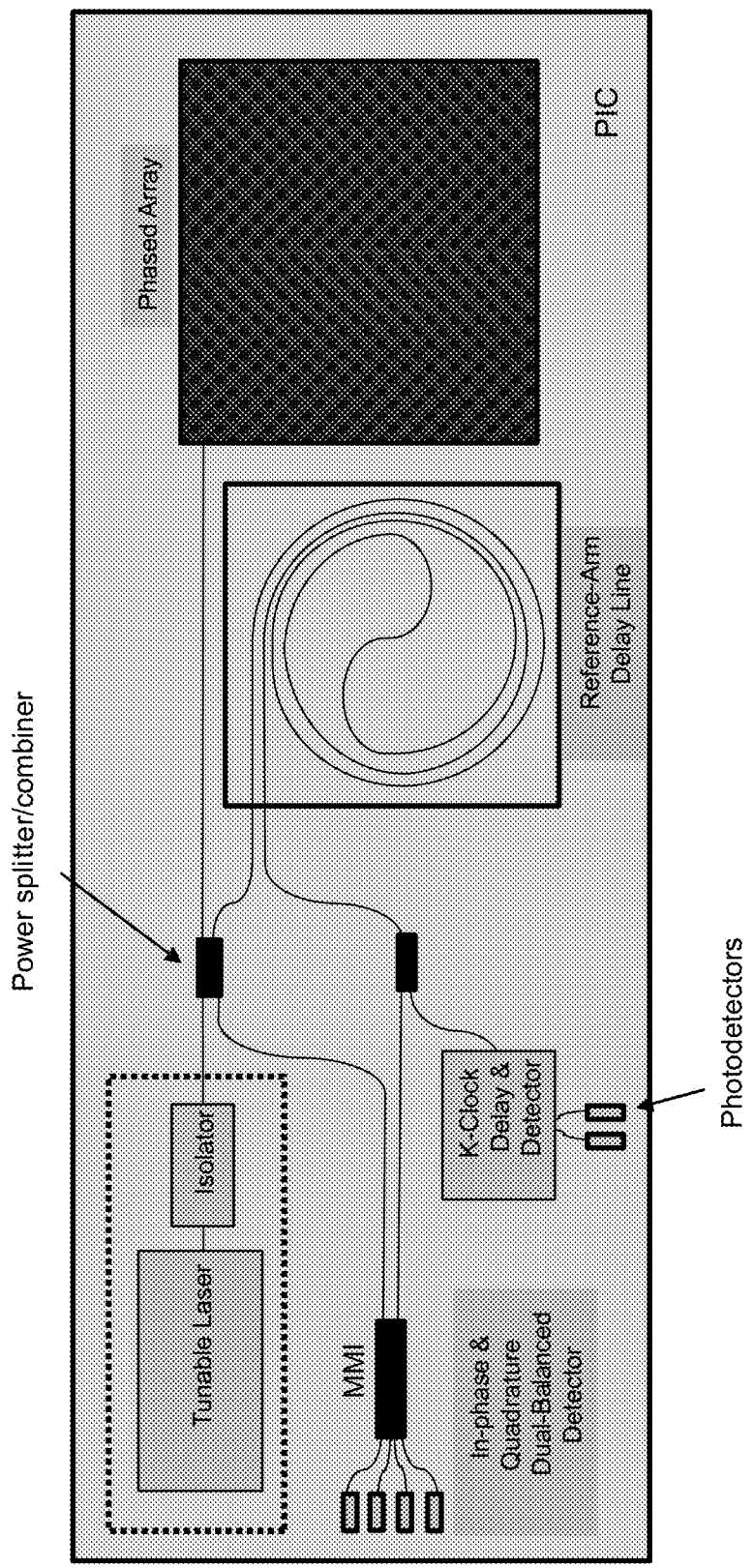
FIG. 31 shows an illustrative example of a coherent interferometric optical ranging, sensor, or imaging system that includes a tunable source, reference arm delay line, phase array, k-clock circuitry, and an in-phase and quadrature dual balanced receiver according to an aspect of the present disclosure.

With reference now to FIG. 31, there is shown in schematic form an illustrative embodiment wherein the entire interferometric optical system (e.g. SS-OCT system) is integrated in a photonic chip along with a phase array. Advantageously, similar topologies may exist for free-space optical communication systems.

Show in the FIG. 31 is a tunable laser and isolator, coupled to a spiral reference-arm delay line and a phase array. The delay line approximately matches the propagation distance from the laser to the sample and back to the receivers with the propagation distance from the laser through the reference arm back to the receivers. If this laser has a very long coherence length then there is less need to match these distances.

Light coupled back into the phased array is combined with an MMI coupler (or other type of coupler) with light passing through the reference arm delay into an in-phase and quadrature dual balanced integrated detector. There is also shown an optional k-clock delay and associated photodetectors.

In another illustrative embodiment the tunable laser and isolator may be located off the photonic chip and just the phased array and in-phase quadrature dual-balanced receivers located on chip. Advantageously, the phased array may be static or may be tunable to scan in 1D or 2D or even adjust its focus to scan in 3D. Although a spiral reference arm-delay is shown there are a variety of other types of delays that may be used and, in addition, it is possible to add heaters to the reference arm to allow for some tunability in the total reference arm delay. Note that in alternative illustrative embodiments, the reference arm may be located "off chip".

In one illustrative embodiment the photonic circuit may be a silicon photonic integrated circuit (PIC) although other types of material and group III-V elements can be used such as InP. Advantageously, silicon photonic integrated circuits are known to have high yields and other attractive manufacturing properties. Notably, normal silicon exhibits a loss of about 0.5 dB/cm so the length of the reference arm is limited. To aid in low loss of the long on-chip reference arm delay, SiN could be used. Note that due to the difference in the optical paths between the sample and reference arm (e.g.

the reference arm is entirely in the photonic integrated circuit and the sample arm light is propagated outside the photonic integrated circuit) the combined light at the photodetector will contain different amounts of chromatic dispersion and other optical path differences. To achieve Fourier transform limited resolution the chromatic dispersion can be compensated for via electronic processing as is known in the art.

As discussed previously, it is possible to design the phase array to scan in one dimension via wavelength tuning of the source and scan in the other dimension via adjustment of the phase tuning elements. Using this approach it is possible to make a 2D imaging system. In this case the phased array can be a 1D phased array or it is still possible to use a 2D array. The advantage of a 1D array is that the antenna elements can be located in very close proximity to minimize side-lobes or higher order interference patterns.

Although FIG. 31 shows an example of a single-polarization receiver, as mentioned above, those skilled in the art will readily realize that it is possible to have a dual polarization system by designing nearly orthogonal feeds to the antenna elements and having two sets of antenna amplitude and phase feed networks and a second in-phase and quadrature dual-balanced receiver.

Figure 32:
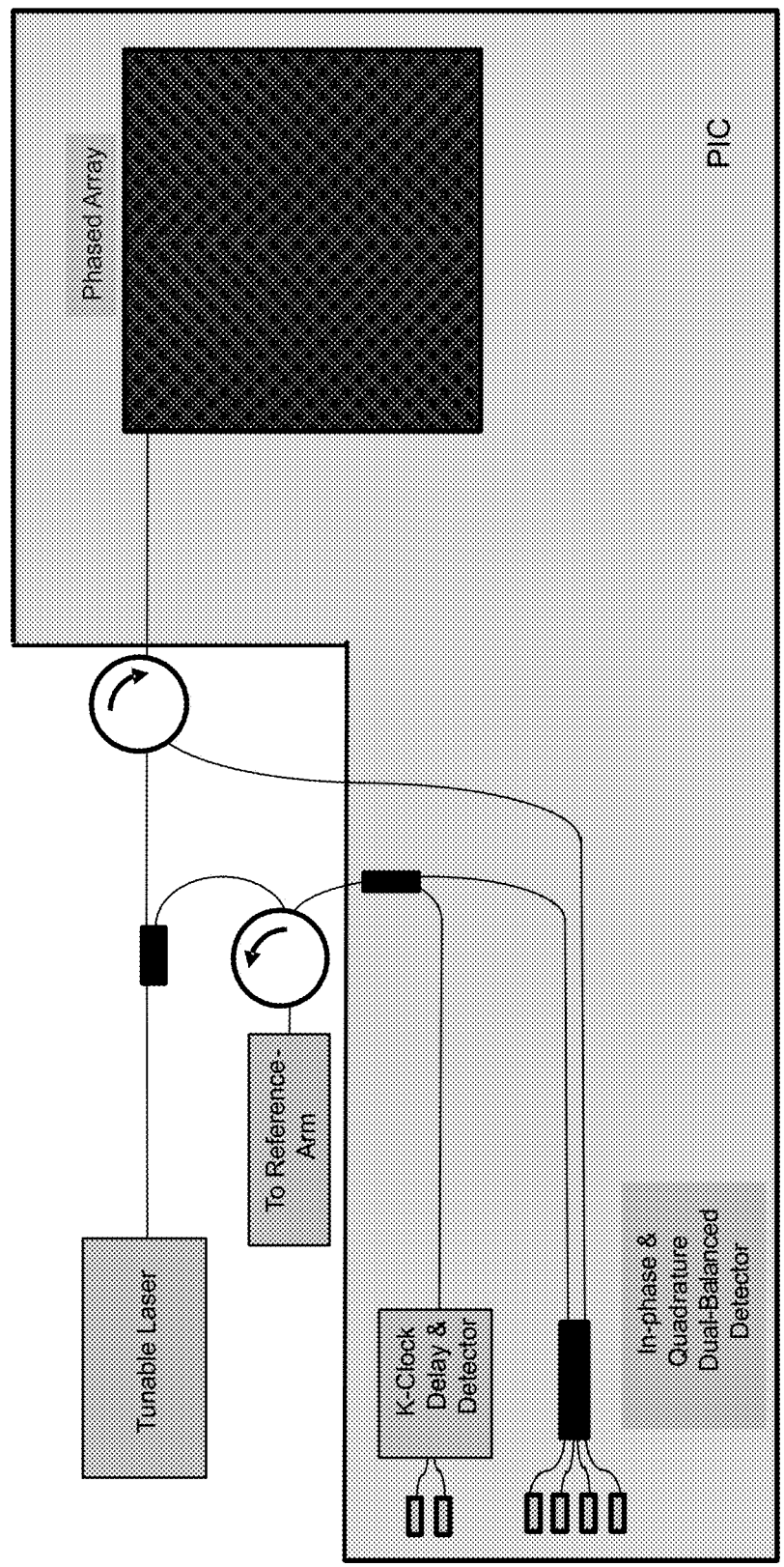
FIG. 32 shows an illustrative example of a coherent interferometric optical ranging system that includes a tunable source, phase array, k-clock circuitry, and an in-phase and quadrature dual balanced receiver according to an aspect of the present disclosure wherein the tunable laser and reference arm is located off chip.

FIG. 32 depicts an illustrative example of a system wherein a laser, circulators, and reference arm are located off a photonic chip and the photonic chip includes a phased array, optional k-clock, and in-phase and quadrature dual-balanced detectors. Notably, one advantage of using circulators instead of splitters is increased optical efficiency and optical isolation.

With reference now to FIG. 33, there is shown an illustrative example(s) according to the present disclosure of a photonic phased array used inside an optical probe such as a guidewire, catheter, endoscope, laparoscope, needle, handheld probe or other medical or non-medical device. More specifically, FIG. 33(a) a side imaging probe, FIG. 33(b) shows a forward imaging probe, and FIG. 33(c) shows a forward-imaging hand-held imaging probe. As may be appreciated these illustrations are not to scale and are only intended to illustrate certain aspects to enable one skilled in the art to incorporate a photonic phased array into medical or non-medical probes. Those skilled in the art will readily appreciate that a variety of other configurations and/or components are compatible with and potentially useful for the other configurations.

As may be further appreciated, these several illustrative embodiments are shown to illustrate how a compact and low-cost integrated photonic phased array can be used according to particular aspects of the present disclosure. Other embodiments are also possible such as integrating a photonic phased array into microscope, a surgical intervention device, a tethered capsule or free swallow-able capsule similar to those sold by Given Imaging (PillCam), etc.

With reference to FIG. 33(a), a side imaging probe includes an optical fiber that is end facet coupled to a PIC containing a phased array that is inside an elongated housing that further includes optional sheathing, support, and structural elements such as a torque cable or polymer jacket or other structural support material. An optional optical lens may be included to aid the transfer of light to and from a sample and the phased array.

Advantageously, in particular exemplary embodiments no lens is needed for some applications and the phased array implements required focusing into the sample (sample not specifically shown) although a lens may be used for other applications. The elongated housing may contain an optical window or the entire sheeting may be optically transparent. Note further with respect to FIG. 33 that electrical connections required to drive an actively scanned photonic phased array are not specifically shown in detail but may be contained within the optical housing or located alternatively.

As previously noted, the photonic phased array depicted in FIG. 33(a), (b), and (c) may be a 1D or 2D array. Advantageously, it may be an active or passive array and may be actively steered in one dimension and wavelength steered in the second dimension and thus implement SECM like scanning in the wavelength steered direction and active phase scanning in the other angular mode. The lens may be a simple symmetric lens or in the case of a 1D array, may contain a cylindrical lens collimating the fast angular divergent axis and the phase array collimating in the other slower divergent axis. Finally, the phased array may be a 2D scanned phased array as well where the emission angle does not vary dramatically over the tuning of any associated light source.

Figure 34:
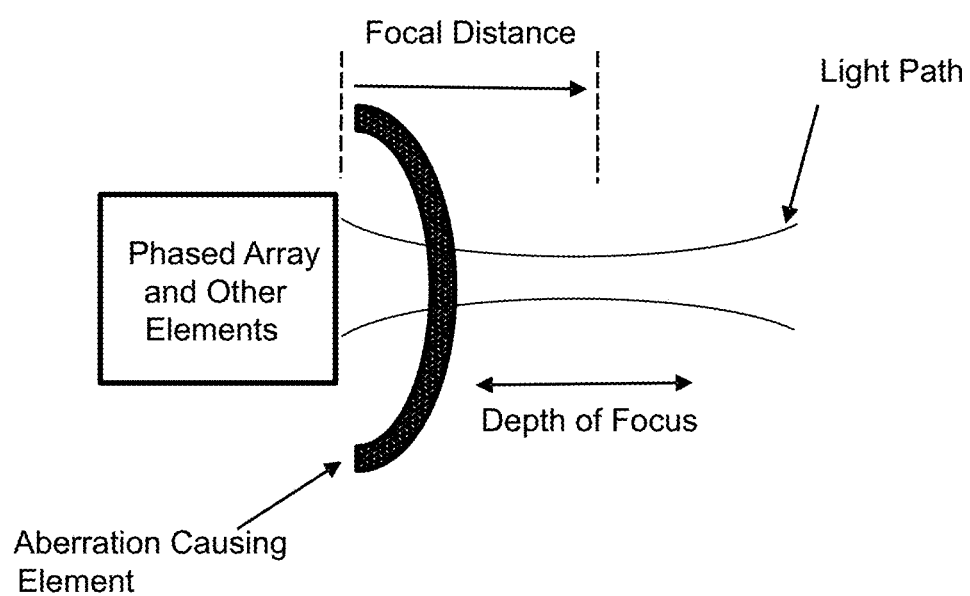
FIG. 34 shows illustrative example according to the present disclosure in which an integrated phased array system focuses light through an optical element that can cause aberrations, in addition to showing the focal distance, and depth of focus from the composite optical systems.

FIG. 34 shows a diagram according to the present disclosure conceptually illustrating focal distance, depth of focus, and an example of an aberration causing element. An example of an aberration causing element could be the cylindrical aberration that can be introduced from the circular sheathing in a guidewire, catheter, or endoscopic probe such as those shown and described previously with respect to FIG. 33.

One advantage of using the integrated optical phase array is that it is possible to compensate for the cylindrical aberration or many other aberrations of the housing or anywhere along the optical path by adjusting the phase and amplitude within the photonic phased array. This can be done in a static fashion or simultaneously with 1D or 2D active lateral scanning.

Additionally, Bessel beam profiles may be implemented to extend the depth of focus and it is possible to adjust the focal distance. All these factors: aberrations along the optical path between the phase array and the sample, extended depth of focus, and changing the focal distance are possible in a static or active phased array in addition to 1D or 2D scanning.

FIG. 33(b) shows an illustrative example of forward imaging according to yet another aspect of the present disclosure. Advantageously a raster scan, spiral scan, or other types of scans known in the art may be employed with such forward imaging arrangements—including multiple simultaneous beams emitting from the phased array. As may be observed from that FIG. 33(b), input coupling is from a surface coupler that is coupled from the back side of the PIC which is preferably thinned during manufacturing.

With reference now to FIG. 33(c), there is shown an illustrative example according to the present disclosure wherein an input fiber is facet coupled and an output photonic phased array comprises a 1D array and is output facet coupled. In such an embodiment it is advantageously possible to utilize a cylindrical lens placed at a location where beam waists are the same such that a roughly symmetric beam is focused into the sample. Of particular note with reference to the illustrative examples depicted in FIG. 33(a), (b), and (c), one may design and configure a probe such that the phased array assembly may be mechanically scanned in one dimension (e.g. rotation) while electronically scanning in another dimension.

FIG. 35 shows illustrative examples according to the present disclosure wherein a PIC containing a phased array is connected with an electronic control circuitry either by having through silicon vias (TSVs) and wafer bonding or using die bonds. As may be understood, it is possible to integrate a complete electronic wafer with an optical wafer. The advantage of close coupling of the photonic PIC and the control circuit is it affords a more compact and reliable system and minimizes complex processing that would otherwise be required in the PIC.

Figure 35A:
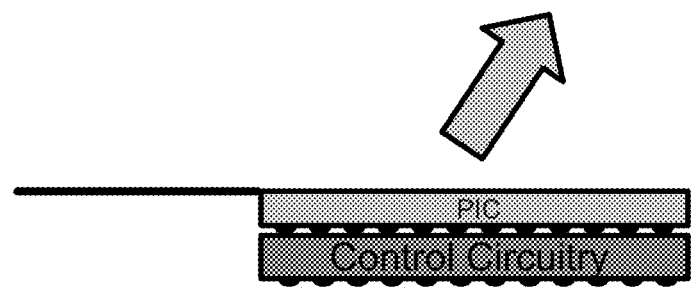
FIG. 35A shows an illustrative example according to the present disclosure of a photonic phased array coupled to control circuitry using wafer bonding or die bonding and stacking of the PIC and control circuitry wafer.
Figure 35B:
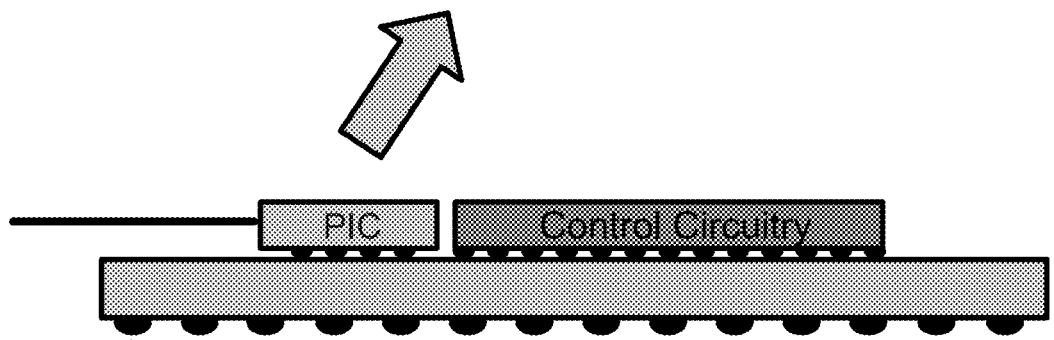
FIG. 35B shows an illustrative example according to the present disclosure of a photonic phased array coupled to control circuitry using wafer bonding or die bonding to a carrier substrate that is connected to an adjacent control wafer.

Continuing, FIG. 35(a) shows an illustrative example according to the present disclosure wherein a phased array PIC is mounted above and in electrical contact with a control circuitry below it. FIG. 35(b) shows an illustrative example according to yet another aspect of the present disclosure wherein a PIC is mounted alongside a control circuit and an intermediate substrate is used to connect the two. Advantageously, such a substrate can have die or ball bonds or more traditional electrical leads along its edge.

Figure 36:
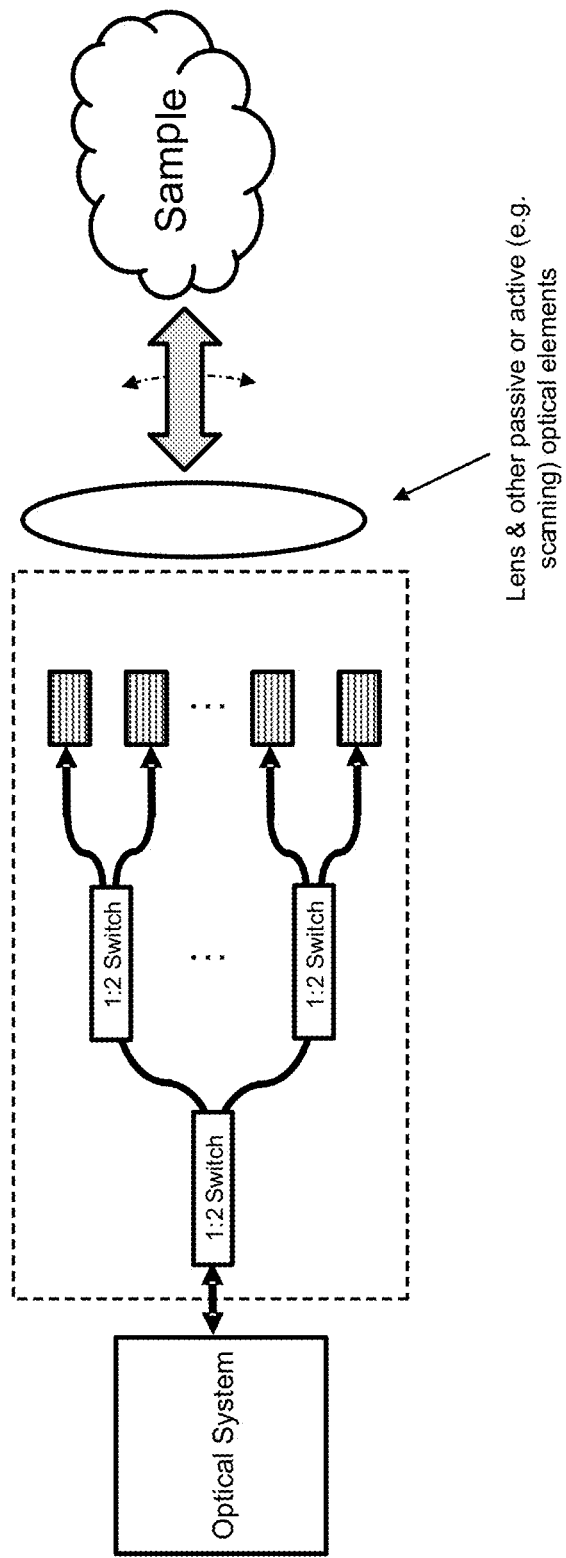
FIG. 36 shows an illustrative example of the present disclosure of a group of integrated optical antennas fed from a spatially switched network to perform spatial scanning.

Turning now to FIG. 36, there it shows an illustrative example of an alternative configuration that produces the scanning of an optical beam from an integrated photonic circuit. As shown, it is possible to connect an optical system such as an SS-OCT system to a set of spatial waveguide switches that are connected to individual integrated photonic emitters/antennas. If the antenna elements are located near the focal plane of the optical system (shown by a simple lens) then, as the light is switched from one element to the next, the angle of the light emanating from the lens will steer in angle as will the focal spot within the sample.

Figure 37A:
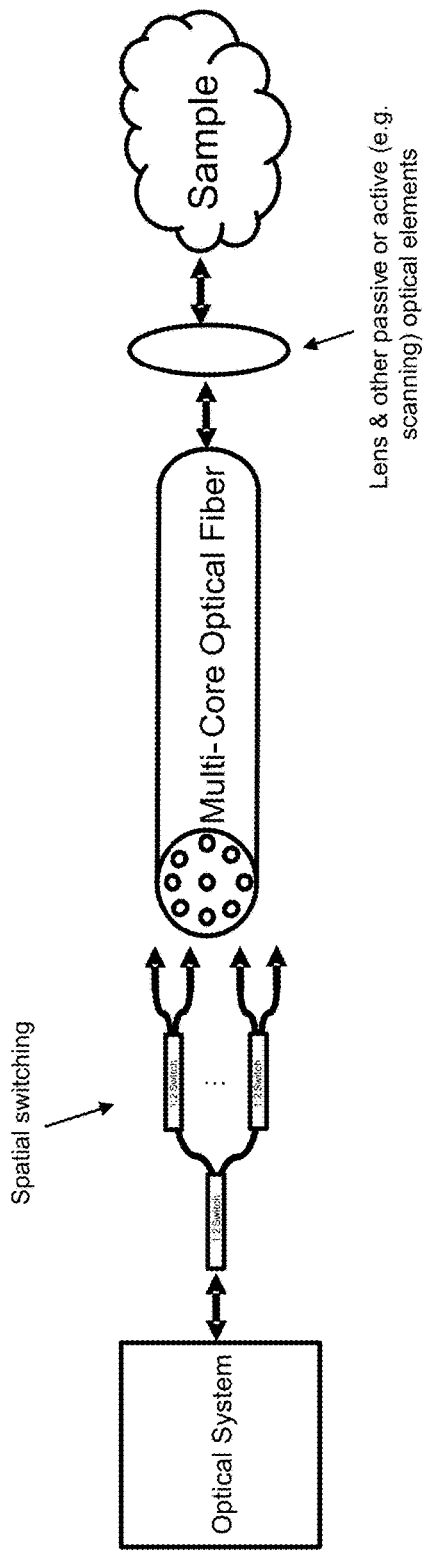
FIG. 37A shows an illustrative example according to the present disclosure of an optical system coupled via a spatially switched optical network into a multicore optical fiber to perform spatial scanning wherein an optical system is connected to a multicore optical fiber via a spatial switching network.

FIG. 37(a) shows in schematic form an illustrative example according to an aspect of the present disclosure of an optical system such as an SS-OCT system coupled into a spatial switched network that couples into individual fibers within a multi-core optical fiber. The multicore optical fiber has distal optics, schematically shown as a simple lens, which couples light to and from a sample of interest. In one embodiment this may be a photonic integrated circuit implementation of an SS-OCT system with multiple sample arms.

Those skilled in the art will readily appreciate that there exist a a variety of types of multi-core optical fibers. Multi-core fiber can qualitatively be described as multiple optical fibers in one. As its name implies there is usually a common cladding material and multiple core materials. Multicore fibers can have as little as two cores or fibers with cores in excess of 10 have been demonstrated. Multicore optical fibers are becoming of increased interest in fiber optic telecom applications, particularly in the data center, where multicore fibers promise to significantly increase the bandwidth capacity of fiber by providing more light-carrying cores than the single core typical of conventional fiber. Multicore fibers can be designed as a non-coupled (or weakly coupled) multi-core fiber and a coupled multi-core fiber are known. In a non-coupled multi-core fiber, respective cores work as transmission passes mostly independent of each other and the cores are coupled as weakly as possible. In a coupled multi-core fiber, respective cores are coupled to each other so that the plurality of cores can be substantially regarded as one multimode transmission path. In the non-coupled case the cores are usually single spatial mode in their guiding of light. As it relates to this disclosure, one illustrative embodiment for SS-OCT is that it is preferable that there be minimal optical coupling between the cores and the cores are near single mode operation Advantageously, the photonic integrated circuit may include of all or part of the optical system including optical switches and may contain surface grating couplers arranged to allow easy coupling of the multicore optical fiber to the photonic integrated circuit. In one illustrative embodiment according to the present disclosure, surface grating couplers are arranged in a same or substantially similar pattern as the multicore optical fiber cores to allow direct butt coupling of the fiber and the photonic integrated circuit.

Figure 37B:
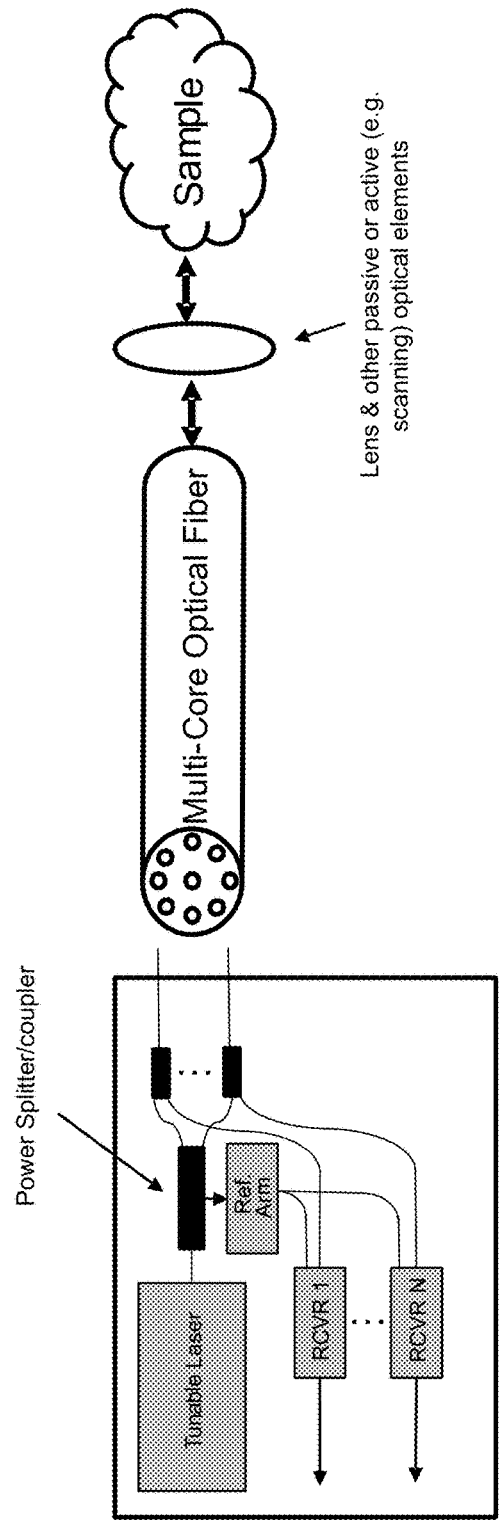
FIG. 37B shows an illustrative example according to the present disclosure of an optical system coupled via a spatially switched optical network into a multicore optical fiber to perform spatial scanning wherein a tunable laser is connected in parallel to a multicore optical fiber and reflections from the multicore optical fiber are connected to an array of coherent optical receivers.

FIG. 37(b) shows another illustrative embodiment wherein a tunable laser is optically coupled to a multicore optical fiber to transmit light to a distant sample. As may be appreciated, light may also be incoming into the optical system. In contrast to that described previously, multiple receivers may be mounted on a single photonic integrated circuit. Consequently, light received from a multicore optical fiber may be detected in a direct detection method or light from a same tunable laser (or a different coherent source) may be coherently combined with light received from the multicore optical fibers and sent to individual coherent receivers. One advantage to this approach is that the detection operates in parallel and eliminates the spatial switching network in favor of separate coherent receivers (one for each core in the multicore fiber).

Note that in the configurations shown in both FIG. 37(a) and FIG. 37(b) connectors may be placed along the optical fiber to allow for—among other things—ease of use (not specifically shown). The connector may be positioned where the multicore fiber connects to the PIC/Optical System or—in other illustrative embodiments—the connector may be positioned along the length of the multicore fiber which may be easier to use.

Note further that in the configurations shown in FIG. 37(a) and FIG. 37(b), a simple single lens is shown at the distal end of the multicore optical fiber to focus the light from the multiple fiber cores into the sample and collect light reflected back from the sample, but as is known in the art more complex fixed optical elements such as fold mirrors, complex spherical or aspherical lens structures, lens arrays, ball lenses, as well as complex active optical elements such as scanning mirrors for circumferential, axial, spiral or forward scanning can be utilized to facilitate 1D, 2D, or 3D imaging.

Returning now to FIG. 31, as noted previously that figure shows an aspect of this disclosure wherein a phased array is located in close proximity to a transmitter and receiver. In the embodiment illustratively shown in that FIG. 31, the phased array is on the same photonic substrate. In many applications it is very important to be able to locate the spatial scanning module (also called a probe module) a long distance from the transmitter and receiver. This includes in medical applications where the scanning can be at the end of a long guidewire, catheter, or endoscope or in other non-medical sensor applications.

Figure 38A:
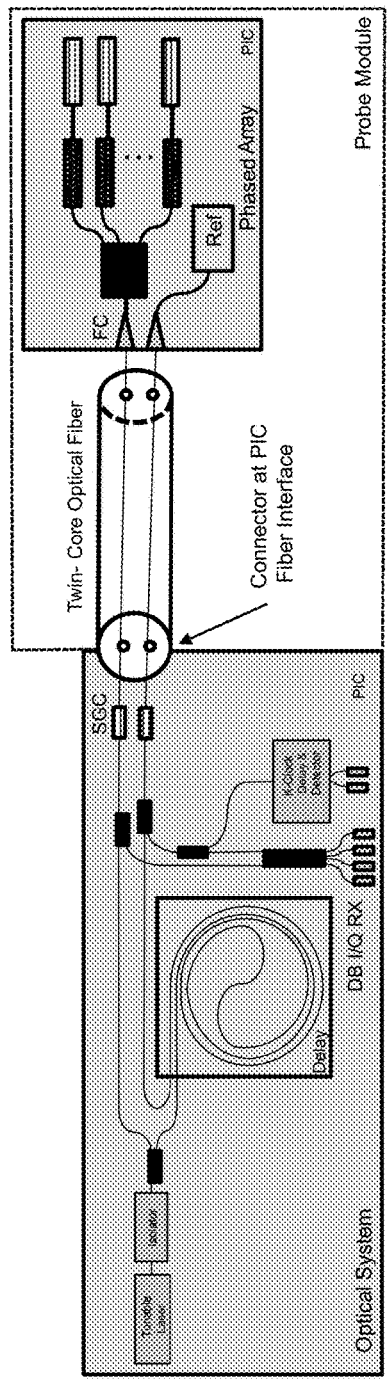
FIG. 38A shows an illustrative example according to the present disclosure wherein a photonic integrated optical system with a transmitter and receiver is connected to a distant photonic phased array via twin-core optical fiber.

Turning now to FIG. 38(a), there it shows an illustrative example according to the present disclosure wherein an optical system is constructed on a photonic integrated circuit including a TX and RX features that use two surface grating couplers (SGC) to couple light into a twin-core optical fiber that is part of a probe module. As shown, the connector is located at the interface between the PIC and the twin-core fiber. It is also possible to use facet coupling and/or have the connector located along the twin-core fiber. This can be a fixed or removable connector. Also it is possible to use two separate fibers instead of a twin-core optical fiber.

As may be appreciated, one advantage of using twin-core optical fiber, preferably single mode twin-core fiber in a common cladding, is that the effects of the environmental disturbances (e.g. bending, acoustic pick up, temperature effects, vibrations, etc) on creating noise in measuring the samples optical properties are dramatically reduced. As may be further appreciated, disturbances cause optical fluctuations in the form of phase, amplitude, and/or polarization alternations that can result in system measurement noise. By having the two cores in close proximity within one cladding, those differential disturbances are dramatically reduced as both fibers are in very close proximity to one another along the entire path and experience mostly the same disturbance and when interferometrically detected much of that common disturbance can cancel out.

Another advantage of such a configuration is that it dramatically reduces the tolerances in manufacturing that normally accompany precisely cutting a reference arm fiber and then cutting a sample arm fiber. Not only does it reduce fiber length cutting tolerances it reduces the need, or at least the longitudinal range requirement, for an adjustable sample arm delay. Because both fibers cores are contained in one cladding they are automatically nearly the exact same length when the fiber is cleaved. Thus the use of multi-core optical fiber can significantly improve performance over many of today's interferometric sensor, ranging, and imaging systems by reducing effects of one or more of the following: environmental disturbances on image quality, reducing the difficulty of precisely cutting fiber lengths in a probe module, and reducing the range requirement of an adjustable sample arm delay unit. In addition as discussed with respect to the configurations shown in FIG. 37, it offers the possibility of multiple sample arm measurements either sequentially or in parallel.

Figure 38B:
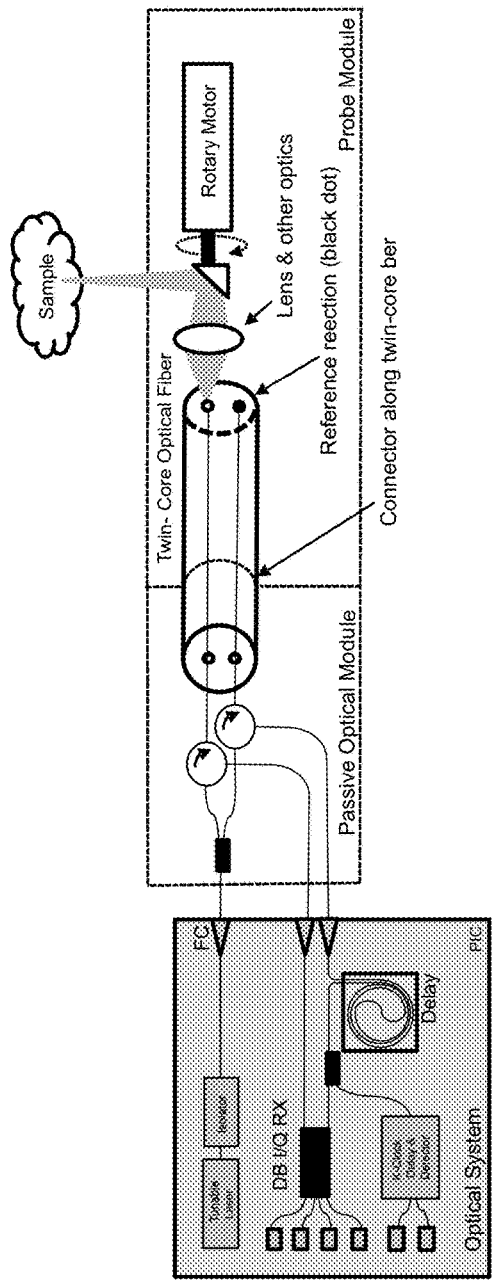
FIG. 38B shows an illustrative example according to the present disclosure wherein the phased array is replaced by a distal rotary motor and the optical connection to and from the distal motor is via multicore optical fiber.

Returning to our discussion of the configuration depicted in FIG. 38(*a*), the distal end of the twin core fiber is connected to a remote phased array containing power splitters, phase shifters, and antenna elements as described previously. The phased array transmits light to and from a sample of interest (not specifically shown) and is controlled by electronics and electrical wires (not specifically shown). Within the probe module, additional optical elements such as fold mirrors, aspheric lenses, cylindrical lens, etc may be contained to facilitate guiding of light to and from the phased array to the sample. Advantageously, the entire probe module could be located a long distance from the optical system. It (the probe module) may be contained within an elongated housing similar to that described in FIG. 33 that contains jackets, torque cables, and other structural and functional items that make up a guidewire, catheter, or endoscope.

As depicted in that FIG. 38(*a*), an integrated phased array is coupled to twin core fiber using surface grating couplers (SGC) however, facet coupling could also be used. One arm of the twin core fiber is coupled to the phased array and the other arm of the twin core fiber is coupled to a reference reflection. The reference reflected light channel within the phased array PIC could contain other active (e.g. a variable optical attenuator) or passive optical elements. A reference arm facet coupler is connected to a waveguide that has a fixed optical reflection is shown but an alternative embodiment is simply to have the fiber to PIC interface serve as a reflection in which case no careful alignment is needed to a waveguide and manufacturing is simplified. Light reflected from the probe modules, phase array channel and reference channels is coupled back into the optical system PIC that contains optional k-clock delay and detector, and a dual balanced in-phase and quadrature receiver (DB I/Q RX). Also shown in the optical system in FIG. 38(*a*) is a Delay in the reference arm that is used to approximately match the reference arm and sample arm distances or delays. This delay can be active or passive but in one preferred embodiment it is passive for simplicity.

Finally, FIG. 38(*b*) shows yet another illustrative embodiment according to the present disclosure wherein a similar optical system is used but to improve broadband coupling efficiency, facet couplers (FC) are used on the PIC. Along the transmitter path there is a passive optical module containing a splitter and two Faraday circulators that are coupled to a twin-core optical fiber along one path and back to the receiver in the optical system. Shown in this FIG. 38(*b*) is mid-span twin-core optical connector which is used to allow the different probe modules to be easily connected as could be the case in a disposable guidewire, catheter or endoscope medical application. The reference arm of the twin core fiber contains a fixed reflection at the output side of the twin core fiber (indicated by the black dot in the figure). Light from the sample arm of the twin core fiber output is collected and focused and otherwise optically manipulated to optimize focusing of light into, and reflected from, the sample using known micro lens techniques such as ball lenses, grin lenses, small injection molded aspheric lenses etc. Shown further in FIG. 38(*b*) is a distal rotary motor that circumferentially spins a small fold mirror to perform circumferential scanning. It should be clear that other types of scanning mechanisms could be contained in the probe module including a phased array, longitudinal pull back scanning, MEMs scanners, PZT scanning in a forward, side, axial, or rotational scanning mode.

At this point it is noted that is it also possible to use more cores than the two that are used in twin-core optical fiber. For example a three core optical fiber could be used where the distal light along the light path from the transmitter laser to the distal end of the probe module is then coupled into a separate fiber as it travels back toward the optical system. The advantage of this approach is that it is more efficient and eliminates one of the couplers in the reference arm path of FIG. 38(*a*) or one of the circulators in FIG. 38(*b*). In general, there are many embodiments of having the probe module located distally from the optical system and interconnecting them with multi-core optical fiber to allow for ease of fabrication, minimizing effects of differential environmental disturbances.

Finally, although FIG. 38(*a*) shows a single polarization dual-balanced, in-phase and quadrature receiver there are other types of receivers that can be implemented as discussed earlier.

Figure 39:
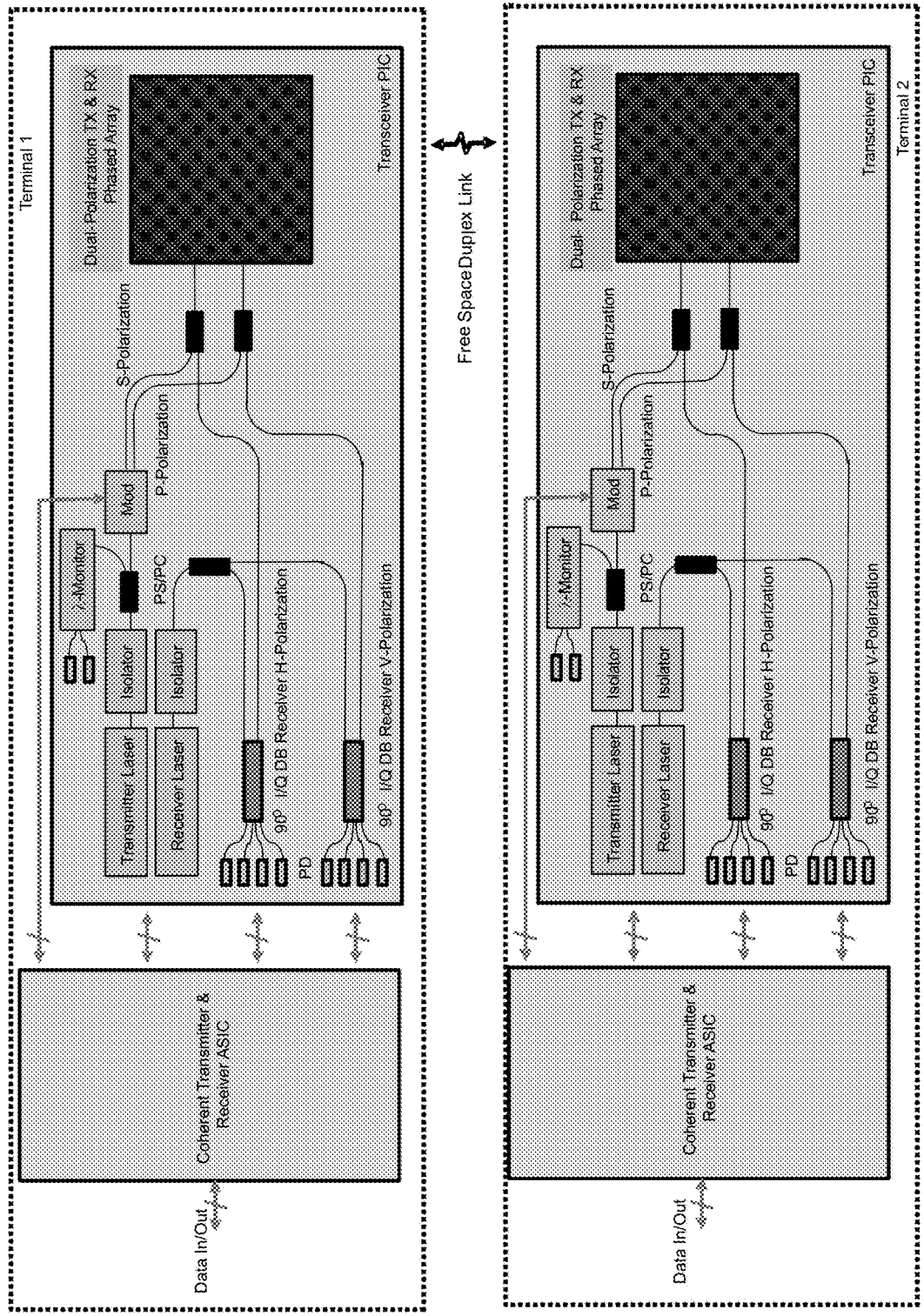
FIG. 39 shows an illustrative example according to the present disclosure of a photonic integrated optical system having a transmitter and receiver and an integrated photonic phased array as illustratively used in a free-space optical communication link.

Turning now to FIG. 39 there it shows another illustrative example of a system according to the present disclosure wherein a photonic integrated optical system includes a transmitter and receiver and an integrated photonic phased array used in a free-space optical communication link between a Terminal 1 and a Terminal 2. As is known in the art, free space laser communication systems, often called LASECOM, are used in a wide variety of applications including: interior building point-to-point communication, exterior building to building communication, tower-to-tower communication, air-to-air communication, air-to-ground communication, and intersatellite communications to name just a few examples. Among the drivers of the design of such systems are: costs, performance, size, data rate, and weight.

As may be appreciated, coherent fiber communication offers great benefit for high-speed fiber optical systems. Recently a duplex silicon 100 Gb/s coherent transceiver without a transmitter or receiver laser, isolator, or phased array was demonstrated. Notably, FIG. 39 shows a coherent ASIC that interfaces with a transceiver PIC. The coherent ASIC may advantageously perform all the forward error correction coding, interleaving, polarization rotation control, PMD, chromatic dispersion, and atmospheric fading compensation as is known in the art. This ASIC has multiple high speed and low speed electrical interfaces to the PIC and is preferably mounted in close proximity to the PIC for signal integrity and design simplicity. The transceiver PIC shown includes separate transmit and receive lasers although in some applications (where there is no Doppler frequency shift due to motion as in satellite to satellite communications or where there is sufficient TX to RX optical isolation) it is possible to use one laser for both applications. The transmitter laser is sent to an optical isolator and to an optional wavelength monitor to enable precise control of the transmitter wavelength. The output is then sent to a modulator which in a preferred embodiment is a dual polarization modulator that implements a form of quadrature amplitude and/or phase modulation (QPSK, QAM, OOK, etc) on each polarization. In alternate embodiments a single polarization transmitter, phased array, and/or receiver is possible. It is also suitable for many applications to have a single polarization transmitter modulator but receive dual polarization. For the diagram illustrated in FIG. 39, the dual polarization modulated output is send into a dual polarization transmitter/receiver phased array. There are a variety of methods to implement a dual polarization phased array including the use of surface grating coupler antenna elements that are well known to accept separate nearly orthogonal polarizations on distinct waveguides. Using these separate polarization inputs it is possible to have two separate feeding networks similar to those shown previously in FIG. 28 and FIG. 29. As may be observed, transmitted light is sent into separate and nearly orthogonal S and P polarization inputs. The received light is coupled and combined with the receiver laser into separate dual balanced, in-phase and quadrature single polarization receivers. Note that the transmitter S or P polarization is not necessarily aligned with the receiver H and V polarization and it is the job of the coherent ASIC to compensate for any misalignment as would continually occur in LASERCOM applications such as air-to-air optical communications where the relative attitudes of Terminal 1 and Terminal 2 are constantly changing.

Note that in FIG. 39 the transceiver PIC and coherent ASIC is shown but it is well known by those skilled in the art that these components are housed in a larger system that includes other devices such as: telescopes, pointing and tracking systems and devices, gimbals, steering mirrors, mounting hardware, thermal management systems, power supplies, etc. While FIG. 39 shows a dual polarization system it is also possible to implement a single polarization system specially when the two terminals are located in a fixed attitude and location and the need for polarization tracking is minimized.

At this point those skilled in the art will readily appreciate that while the methods, techniques and structures according to the present disclosure have been described with respect to particular implementations and/or embodiments, those skilled in the art will recognize that the disclosure is not so limited. In particular, where multiple integrated chips are employed, those chips may advantageously be closely coupled by positioning them on a common carrier or within a common packaging. As may be appreciated, in this manner the chips may be physically close to one another of close in time to one another as appropriate. Accordingly, the scope of the disclosure should only be limited by the claims appended hereto.

The invention claimed is:
1. An optical-fiber measurement system comprising:
 a) a tunable laser that generates light with a tunable wavelength at an output;
 b) an optical coupler having an optical input coupled to the output of the tunable laser, the optical coupler spatially processing the light generated by the tunable laser and providing light at a plurality of optical ports;
 c) a multicore optical fiber comprising a plurality of optical cores, a respective one of the plurality of optical cores at a first end of the multicore optical fiber being positioned to receive the light provided at a respective one of the plurality of optical ports of the optical coupler, the light propagating through the multicore optical fiber;
 d) distal optics positioned proximate to a second end of the multicore optical fiber so to receive the light propagated through the multicore optical fiber and positioned to collect light from a sample of interest so that the collected light from the sample of interest is coupled to one or more of the plurality of optical cores at the second end of the multicore optical fiber; and
 e) a plurality of optical receivers, a respective first input of each of the plurality of optical receivers being coupled to a respective optical core of the multicore optical fiber through the optical coupler and a respective second input of each of the plurality of optical receivers being coupled to at least some of the plurality of optical ports of the optical coupler.

2. The optical-fiber measurement system of claim 1 wherein the tunable laser comprises a frequency-swept light source.

3. The optical-fiber measurement system of claim 1 wherein the multicore optical fiber comprises a plurality of non-coupled optical cores.

4. The optical-fiber measurement system of claim 1 wherein the multicore optical fiber comprises a plurality of coupled optical cores.

5. The optical-fiber measurement system of claim 1 wherein the multicore optical fiber comprises a plurality of single mode optical cores.

6. The optical-fiber measurement system of claim 1 wherein the distal optics comprises a distal optical module.

7. The optical-fiber measurement system of claim 1 wherein the distal optics comprises a single-element lens.

8. The optical-fiber measurement system of claim 1 wherein the distal optics comprises a multi-element lens.

9. The optical-fiber measurement system of claim 1 wherein the distal optics comprises a lens selected from the group consisting of complex spherical lenses, aspherical lens structures, lens arrays, and ball lenses.

10. The optical-fiber measurement system of claim 1 wherein the distal optics comprises a plurality of lenses, wherein a respective one of the plurality of lenses is aligned to a respective one of the plurality of optical cores of the multicore optical fiber at the second end.

11. The optical-fiber measurement system of claim 1 wherein the plurality of optical receivers comprises a photonic integrated circuit.

12. The optical-fiber measurement system of claim 1 wherein the distal optics comprises at least one scanning mirror positioned proximate to the second end of the multicore optical fiber.

13. The optical-fiber measurement system of claim 12 wherein the at least one scanning mirror performs circumferential scanning.

14. The optical-fiber measurement system of claim 12 wherein the at least one scanning mirror performs forward scanning.

15. The optical-fiber measurement system of claim 12 wherein the at least one scanning mirror performs spiral scanning.

16. The optical-fiber measurement system of claim 12 wherein the at least one scanning mirror performs one dimensional scanning.

17. The optical-fiber measurement system of claim 12 wherein the at least one scanning mirror performs two dimensional scanning.

18. The optical-fiber measurement system of claim 12 wherein the at least one scanning mirror performs three dimensional scanning.

19. The optical-fiber measurement system of claim 1 wherein each of the plurality of optical receivers comprises a coherent optical receiver.

20. The optical-fiber measurement system of claim 1 wherein each of the plurality of optical receivers processes light from a plurality of sample paths to produce a plurality of parallel measurements.

21. The optical-fiber measurement system of claim 1 further comprising at least one optical connector that couples the optical coupler to the multicore optical fiber.

22. The optical-fiber measurement system of claim 1 further comprising at least one optical connector that couples a first and second portion of the multicore optical fiber.

23. The optical-fiber measurement system of claim 1 wherein the collected light from the sample is backscattered light from the sample.

24. The optical-fiber measurement system of claim 1 wherein the collected light from the sample is reflected light from the sample.

* * * * *